(12) United States Patent
Karras et al.

(10) Patent No.: US 7,507,810 B2
(45) Date of Patent: Mar. 24, 2009

(54) COMPOSITIONS AND THEIR USES DIRECTED TO IL-4R ALPHA

(75) Inventors: James G. Karras, San Marcos, CA (US); Susan Gregory, San Diego, CA (US); Susan M. Freier, San Diego, CA (US); William A. Gaarde, Carlsbad, CA (US); Mausumee Guha, Carlsbad, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 11/548,650

(22) Filed: Oct. 11, 2006

(65) Prior Publication Data

US 2007/0161593 A1  Jul. 12, 2007

Related U.S. Application Data

(63) Continuation of application No. PCT/US2006/006645, filed on Feb. 24, 2006.

(60) Provisional application No. 60/656,760, filed on Feb. 25, 2005, provisional application No. 60/688,897, filed on Jun. 9, 2005, provisional application No. 60/700,656, filed on Jul. 19, 2005, provisional application No. 60/709,404, filed on Aug. 18, 2005.

(51) Int. Cl.
  *C07H 21/04*  (2006.01)
  *C07H 21/02*  (2006.01)
  *A61K 48/00*  (2006.01)

(52) U.S. Cl. ............... 536/24.5; 536/23.1; 536/24.3; 514/44

(58) Field of Classification Search ............... None
See application file for complete search history.

(56) References Cited

U.S. PATENT DOCUMENTS

| | | |
|---|---|---|
| 5,489,677 A | 2/1996 | Sanghvi et al. |
| 5,602,240 A | 2/1997 | De Mesmaeker et al. |
| 5,625,050 A | 4/1997 | Beaton et al. |
| 5,677,439 A | 10/1997 | Weis et al. |
| 5,688,941 A | 11/1997 | Cook et al. |
| 5,700,922 A | 12/1997 | Cook |
| 5,719,262 A | 2/1998 | Buchardt et al. |
| 5,750,692 A | 5/1998 | Cook et al. |
| 5,789,573 A | 8/1998 | Baker et al. |
| 5,898,031 A | 4/1999 | Crooke |
| 6,007,992 A | 12/1999 | Lin et al. |
| 6,028,183 A | 2/2000 | Lin et al. |
| 6,107,094 A | 8/2000 | Crooke |
| 6,147,200 A | 11/2000 | Manoharan et al. |
| 6,210,892 B1 | 4/2001 | Bennett et al. |
| 6,379,890 B1 | 4/2002 | Hershey |
| 6,656,695 B2 | 12/2003 | Berg et al. |
| 6,656,730 B1 | 12/2003 | Manoharan |
| 6,762,169 B1 | 7/2004 | Manoharan |
| 6,822,087 B1 | 11/2004 | Renzi |
| 6,878,751 B1 | 4/2005 | Donnelly et al. |
| 2002/0049173 A1 | 4/2002 | Bennett et al. |
| 2003/0078220 A1 | 4/2003 | Chew et al. |
| 2003/0104410 A1 | 6/2003 | Mittmann |
| 2003/0158403 A1 | 8/2003 | Manoharan et al. |
| 2003/0175906 A1 | 9/2003 | Manoharan et al. |
| 2003/0207804 A1 | 11/2003 | Manoharan et al. |
| 2004/0040052 A1 | 2/2004 | Radcliffe et al. |
| 2004/0049022 A1 | 3/2004 | Nyce et al. |
| 2004/0171566 A1 | 9/2004 | Monia et al. |
| 2004/0235164 A1 | 11/2004 | Bennett et al. |
| 2005/0143333 A1* | 6/2005 | Richards et al. ............... 514/44 |
| 2005/0261219 A1 | 11/2005 | Richards et al. |

FOREIGN PATENT DOCUMENTS

| | | | |
|---|---|---|---|
| WO | WO 94/26764 A1 | 11/1994 | |
| WO | WO 96/40162 | 12/1996 | |
| WO | WO 99/66037 A2 | 12/1999 | |
| WO | WO 00/34789 * | 6/2000 | ............... 536/24.5 |
| WO | WO 00/34789 A2 | 6/2000 | |
| WO | WO 02/085308 A2 | 10/2002 | |
| WO | WO 02/085309 A2 * | 10/2002 | ............... 514/44 |
| WO | WO 02/085309 A2 | 10/2002 | |
| WO | WO 2003/004602 A2 | 1/2003 | |
| WO | WO 2004/011613 A2 | 2/2004 | |
| WO | WO 2004/031237 | 5/2004 | |
| WO | WO 2004/045543 A2 | 6/2004 | |
| WO | WO 2004/108945 A2 | 12/2004 | |

(Continued)

OTHER PUBLICATIONS

Only pp. 1-27 and 693 are included for document WO 02/085309 A2.*

(Continued)

*Primary Examiner*—Amy Bowman
(74) *Attorney, Agent, or Firm*—Swanson & Bratschun, L.L.C.

(57) ABSTRACT

Disclosed herein are compounds, compositions and methods for modulating the expression of IL-4R alpha in a cell, tissue or animal. Also provided are methods of target validation. Also provided are uses of disclosed compounds and compositions in the manufacture of a medicament for treatment of diseases and disorders related to expression of IL 4R-α, airway hyperresponsiveness, and/or pulmonary inflammation.

11 Claims, No Drawings

FOREIGN PATENT DOCUMENTS

Figure 1:
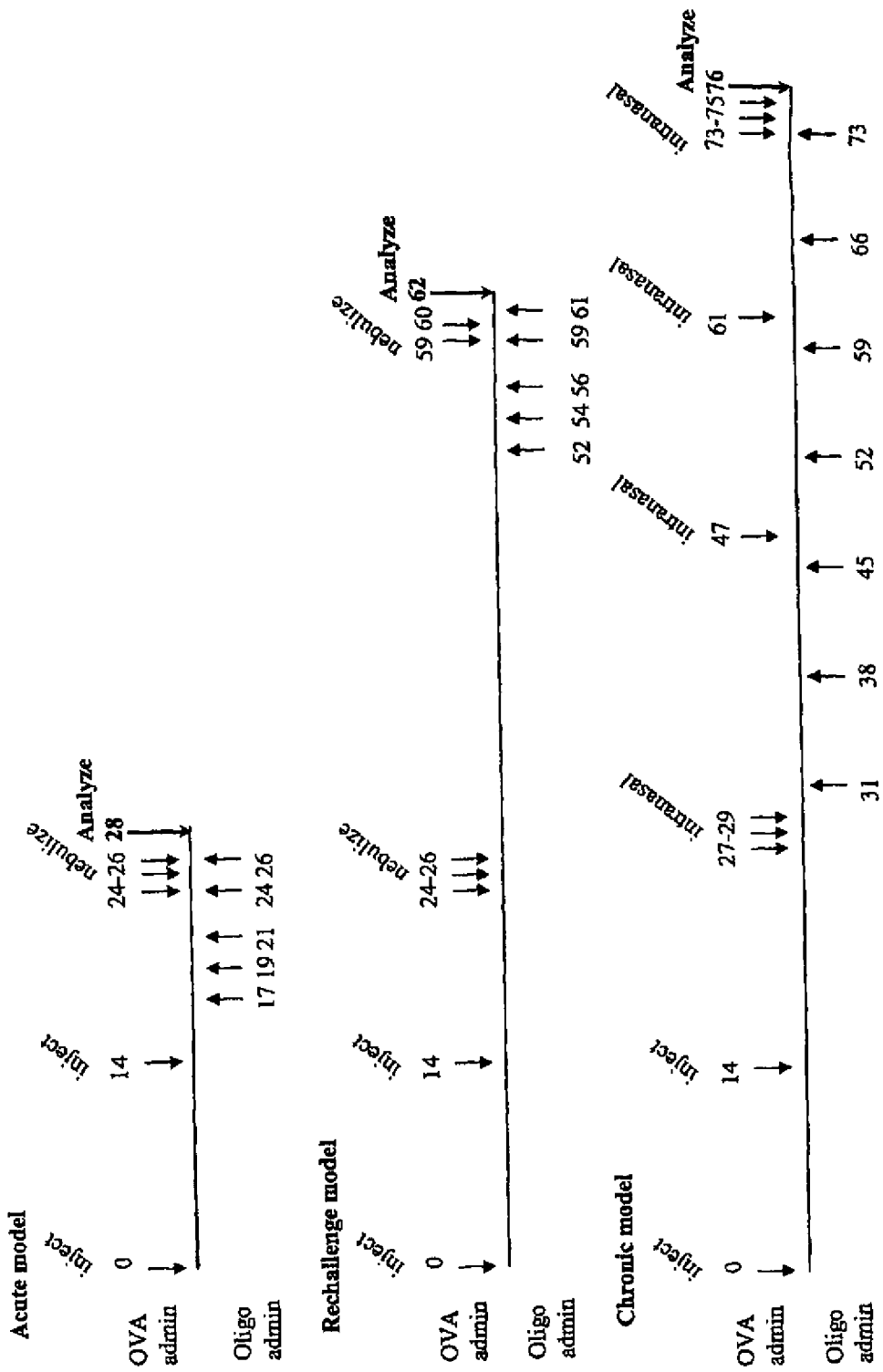

| WO | WO 2006/091841 A2 | 8/2006 |
|---|---|---|
| WO | WO 2007/041719 A2 | 4/2007 |

OTHER PUBLICATIONS

Olie et al., Analysis of ribosyl-modified, mixed backbone analogs of a bcl-2/bcl-xL antisense oligonucleotide, 2002, Biochimica et Biophysica Acta, 1576, pp. 101-109.*

PCT International Search Report for PCT/US2006/006645, dated Jan. 8, 2006.

PCT International Search Report for PCT/US2006/039168, dated Apr. 3, 2007.

Borish, L. C. et al., "Interleukin-4 Receptor in Moderate Atopic Asthma," *Am J. Respir. Crit. Care Med.* (1999) 160:1816-1823.

Churg, A. et al., "Acute Cigarette Smoke-Induced Connective Tissue Breakdown Requires both Neutrophils and Macrophage Metalloelastase in Mice," *Am. J. Respir. Cell Mol. Biol.* (2002) 27:368-374.

Churg, A. et al., "Tumor Necrosis Factor-α Drives 70% of Cigarette Smoke-induced Emphysema in the Mouse," *Am. J. Respir. Crit. Care Med.* (2004) 170:492-498.

Dellinger, D. J. et al., "Solid-Phase Chemical Synthesis of Phosphonoacetate and Thiophosphonoacetate Oligodeoxyribonucleotides," *J. Am. Chem. Soc.* (2003) 125(4):940-950.

Dreyfus, D. H. et al., "An RNA external guide sequence ribozyme targeting human interleukin-4 receptor α mRNA," *Int. Immunopharm.* (2004) 4:1015-1027.

Galizzi, J.-P. et al., "Molecular cloning of a cDNA encoding the human interleukin 4 receptor," *International Immunology* (1990) 2(7):669-675.

Grünig, G. et al., "Requirement for IL-13 Independently of IL-4 in Experimental Asthma," *Science* (1998) 282:2261-2263.

Gryaznov, S. et al., "Oligodeoxynribonucleotide N3'→P5' Phosphoramidates: Synthesis and Hybridization Properties," *J. Am. Chem. Soc.* (1994) 116(7):3143-3144.

Hershey, G. K. K. et al., "The Associatio of Atopy with a Gain-of-Function Mutation in the α Subunit of the Interleukin-4 Receptor," *N. Engl. J. Med.* (1997) 337:1720-1725.

Idzerda, R. L. et al., "Human Interleukin 4 Receptor Confers Biological Responsiveness and Defines a Novel Receptor Superfamily," *J. Exp. Med.* (1990) 171:861-873.

Ikizawa, K. et al., "Inhibition of IL-4 receptor up-regulation on B cells by antisense oligodeoxynucleotide suppresses IL-4-induced human IgE production," *Clin. Exp. Immunol.* (1995) 100:383-389.

Kruse, S. et al., "The polymorphism S503P and Q576R in the interleukin-4 receptor α gene are associated with atopy and influence the signal transduction," *Immunol.* (1999) 96:365-371.

Kumar, R. K. et al., "Effects of Anticytokine Therapy in a Mouse Model of Chronic Asthma," *Am J. Respir. Crit. Care Med.* (2004) 170:1043-1048.

Metzger, W. J. et al., "Respirable Antisense Oligonucleotide (RASON) Therapy for Allergic Asthma," *BioDrugs* (1999) 12(4):237-243.

Nyce, J. W., "Respirable antisense oligonucleotides as novel therapeutic agents for asthma and other pulmonary diseases," *Exp. Opin. Invest. Drugs* (1997) 6(9):1149-1156.

Nyce, J. W. et al., "DNA antisense therapy for asthma in an animal model," *Nature* (1997) 385:721-725.

Pritchard, M. A. et al., "The Interleukin-4 Receptor Gene (*IL4R*) Maps to 16p11.2-16p12.1 in Human and to the Distal Region of Mouse Chromosome 7," *Genomics* (1991) 10:801-806.

Rosa-Rosa, L. et al., "The R576 IL-4 receptor α allele correlates with asthma severity," *J. Allergy Clin. Immunol.* (1999) 104:1008-1014.

Sheehan, D. et al., "Biochemical properties of phosphonoacetate and thiophosphonoacetate oligodeoxyribonucleotides," *Nucleic Acids Res.* (2003) 31(14):4109-4118.

Tijesterman, M. et al., "RNA Helicase MUT-14-Dependent Gene Silencing Triggered in *C. elegans* by Short Antisense RNAs," *Science* (2002) 295:694-697.

Vickers, T. A. et al., "Efficient Reduction of Target RNAs by Small Interfering RNA and RNase H-dependent Antisense Agents," *J. Biol. Chem.* (2003) 278(9):7108-7118.

Wahlestedt, C. et al., "Potent and nontoxic antisense oligonucleotides containing locked nucleic acids," *PNAS* (2000) 97(10):5633-5638.

Wills-Karp, M. et al., "Interleukin-13: Central Mediator of Allergic Asthma," *Science* (1998) 282:2258-2261.

Yanagihara, Y. et al., "Functional significance of IL-4 receptor on B cells in IL-4-induced human IgE production," *J. Allergy Clin. Immunol.*(1995) 96:1145-1151.

Yang, G. et al., "Anti-IL-13 monoclonal antibody inhibits airway hyperresponiveness, inflammation and airway remodeling," *Cytokine* (2004) 28:224-232.

Elbashir et al., "Functional anatomy of siRNAs for mediating efficient RNAi in *Drosophila melanogaster* embryo lysate," The EMBO Journal (2001) 20(23):6877-6888.

Holen et al., "Positional effects of short interfering RNAs targeting the human coagulation trigger Tissue Factor", (2002) Nucleic Acids Research, 30(8):1757-1766.

Mahato et al., "Modulation of gene expression by antisense and antigene oligodeoxynucleotides and small interfering RNA," (Jan. 2005) Expert Opinion on Drug Delivery, 2(1):3-28.

Scherer et al., "Approaches for the sequence-specific knockdown of mRNA," (2003) Nature Biotechnology, 21(12):1457-1465.

Tuschl et al., "The siRNA user guide" Aug. 26, 2001 (on-line) Max Planck Institute for Biophysical Chemistry, pp. 1, 3 and 5.

Bertrand et al., (2002) Biochemical and Biophysical Research Communications 269:1000-1004 "Comparison of antisense oligonucleotides and siRNAs in cell culture and in vivo".

Chatila (2004) Trends in Molecular Medicine 10:493-499 "Interleukin-4 receptor signaling pathways in asthma pathogenesis".

* cited by examiner

SEQUENCE LISTING

<160> NUMBER OF SEQ ID NOS: 306

<210> SEQ ID NO 1
<211> LENGTH: 3597
<212> TYPE: DNA
<213> ORGANISM: Homo sapiens

<400> SEQUENCE: 1
ggcgaatgga gcagggcgc gcagataatt aaagatttac acacagctgg aagaaatcat    60
agagaagccg ggcgtggtgg ctcatgccta taatcccagc acttttggag gctgaggcgg   120
gcagatcact tgagatcagg agttcgagac cagcctggtg ccttggcatc tcccaatggg   180

```
gtggctttgc tctgggctcc tgttccctgt gagctgcctg gtcctgctgc aggtggcaag      240
ctctgggaac atgaaggtct tgcaggagcc cacctgcgtc tccgactaca tgagcatctc      300
tacttgcgag tggaagatga atggtcccac caattgcagc accgagctcc gcctgttgta      360
ccagctggtt tttctgctct ccgaagccca cacgtgtatc cctgagaaca cggaggcgc       420 ggggtgcgtg tgccacctgc tcatggatga cgtggtcagt gcggataact atacactgga     480
cctgtgggct gggcagcagc tgctgtggaa gggctccttc aagcccagcg agcatgtgaa      540
acccagggcc ccaggaaacc tgacagttca ccaatgtc tccgacactc tgctgctgac       600
ctggagcaac ccgtatcccc tgacaatta cctgtataat catctcacct atgcagtcaa      660
catttggagt gaaaacgacc cggcagattt cagaatctat aacgtgacct acctagaacc      720
ctccctccgc atcgcagcca gcaccctgaa gtctgggatt cctacaggg cacgggtgag      780 ggcctgggct cagtgctata acaccacctg gagtgagtgg agcccagca ccaagtggca      840 caactcctac agggagccct cgagcagca cctcctgctg ggcgtcagcg tttcctgcat      900
tgtcatcctg gccgtctgcc tgttgtgcta tgtcagcatc accaagatta gaaagaatg      960 gtgggatcag attcccaacc cagcccgcag ccgcctcgtg gctataataa tccaggatgc     1020
tcaggggtca cagtgggaga gcggtcccg aggccaggaa ccagccaagt gcccacactg     1080
gaagaattgt cttaccaagc tcttgccctg ttttctggag cacaacatga aaagggatga     1140
agatcctcac aaggctgcca agagatgcc tttccagggc tctggaaaat cagcatggtg     1200
cccagtggag atcagcaaga cagtcctctg gccagagagc atcagcgtgg tgcgatgtgt     1260
ggagttgttt gaggcccggg tggagtgtga ggaggaggag gaggtagagg aagaaaaagg     1320
gagcttctgt gcatcgcctg agagcagcag ggatgacttc caggagggaa gggagggcat     1380
tgtggcccgg ctaacagaga gcctgttcct ggacctgctc ggagaggaga atggggctt     1440 ttgccagcag gacatggggg agtcatgcct tcttccacct tcgggaagta cgagtgctca     1500
catgccctgg gatgagttcc caagtgcagg gcccaaggag gcacctccct ggggcaagga     1560
gcagcctctc cacctggagc caagtcctcc tgccagcccg acccagagtc cagacaacct     1620
gacttgcaca gagacgcccc tcgtcatcgc aggcaaccct gcttaccgca gcttcagcaa     1680
ctccctgagc cagtcaccgt gtcccagaga gctgggtcca gacccactgc tggcagaca      1740 cctggaggaa gtagaacccg agatgccctg tgtcccccag ctctctgagc caaccactgt     1800
gccccaacct gagccagaaa cctgggagca gatcctccgc cgaaatgtcc tccagcatgg     1860
ggcagctgca gcccccgtct cggcccccac cagtggctat caggagtttg tacatgcggt     1920
ggagcagggg ggcacccagg ccagtgcggt ggtgggcttg ggtcccccag agaggctgg     1980 ttacaaggcc ttctcaagcc tgcttgccag cagtgctgtg tccccagaga aatgtgggtt     2040
tggggctagc agtggggaag aggggtataa gcctttccaa gacctcattc ctggctgccc     2100 tgggaccct gccccagtcc ctgtcccctt gttcaccttt ggactggaca gggagccacc     2160
tcgcagtccg cagagctcac atctcccaag cagctcccca gagcacctgg gtctggagcc     2220
gggggaaaag gtagaggaca tgccaaagcc cccacttccc caggagcagg ccacagaccc     2280
ccttgtggac agcctgggca gtggcattgt ctactcagcc cttacctgcc acctgtgcgg     2340
ccacctgaaa cagtgtcatg ccaggagga tggtggccag acccctgtca tggccagtcc     2400
ttgctgtggc tgctgctgtg agacaggtc ctcgcccct acaacccccc tgagggcccc     2460 agaccctct ccaggtgggg ttccactgga ggccagtctg tgtccggcct ccctggcacc      2520
```

-continued

```
ctcgggcatc tcagagaaga gtaaatcctc atcatccttc catcctgccc ctggcaatgc      2580
tcagagctca agccagaccc ccaaaatcgt gaactttgtc tccgtgggac ccacatacat      2640
gagggtctct taggtgcatg tcctcttgtt gctgagtctg cagatgagga ctagggctta      2700
tccatgcctg ggaaatgcca cctcctggaa ggcagccagg ctggcagatt tccaaaagac      2760
ttgaagaacc atggtatgaa ggtgattggc cccactgacg ttggcctaac actgggctgc      2820
agagactgga ccccgcccag cattgggctg ggctcgccac atcccatgag agtagagggc      2880
actgggtcgc cgtgccccac ggcaggcccc tgcaggaaaa ctgaggccct tgggcacctc      2940
gacttgtgaa cgagttgttg gctgctccct ccacagcttc tgcagcagac tgtccctgtt      3000
gtaactgccc aaggcatgtt ttgcccacca gatcatggcc cacgtggagg cccacctgcc      3060
tctgtctcac tgaactagaa gccgagccta gaaactaaca cagccatcaa gggaatgact      3120
tgggcggcct tgggaaatcg atgagaaatt gaacttcagg gagggtggtc attgcctaga      3180
ggtgctcatt catttaacag agcttcctta ggttgatgct ggaggcagaa tcccggctgt      3240
caaggggtgt tcagttaagg ggagcaacag aggacatgaa aaattgctat gactaaagca      3300
gggacaattt gctgccaaac acccatgccc agctgtatgg ctggggctc ctcgtatgca       3360 tggaaccccc agaataaata tgctcagcca ccctgtgggc cggcaatcc agacagcagg       3420 cataaggcac cagttaccct gcatgttggc ccagacctca ggtgctaggg aaggcgggaa      3480
ccttgggttg agtaatgctc gtctgtgtgt tttagtttca tcacctgtta tctgtgtttg      3540
ctgaggagag tggaacagaa ggggtggagt tttgtataaa taaagtttct ttgtctc        3597
```

<210> SEQ ID NO 2
<211> LENGTH: 3697
<212> TYPE: DNA
<213> ORGANISM: Mus musculus

<400> SEQUENCE: 2

```
cgcaggaaag ccccgcgcgg cgcgtggagc ctgaactcgc aggttctggc tggacttctc       60
gaagctgagg agaagcagag ggacctggct tctgattttg gatctgcgtg cttgctggtt      120
ctggcgcctg ctggtcttgt tcctgtaacc taggactcgg ggcttgcaca tgcttttttt      180
ttgaagttgc tggagaggga gcccaggacc ttgtgcaggc accttttgtg tccccaatgg      240
ggcggctttg caccaagttc ctgacctctg tgggctgtct gattttgctg ttggtgactg      300
gatctgggag catcaaggtc ctgggtgagc ccacctgctt ctctgactac atccgcactt      360
ccacgtgtga gtggttcctg atagcgctg tggactgcag ttctcagctc tgcctacact       420
acaggctgat gttcttcgag ttctctgaaa acctcacatg catcccgagg aacagtgcca      480
gcactgtgtg tgtgtgccac atggaaatga ataggccggt ccaatcagac agataccaga      540
tggaactgtg ggctgagcac agacagctgt ggcagggctc cttcagcccc agtggtaatg      600
tgaagcccct agctccagac aacctcacac tccacaccaa tgtgtccgac gaatggctgc      660
tgacctggaa taacctgtac ccatcgaaca acttactgta caaagacctc atctccatgg      720
tcaacatctc cagagaggac aaccctgcag aattcatagt ctataatgtg acctacaagg      780
aacccaggct gagcttcccg atcaacatcc tgatgtcagg ggtctactat acggcgcgtg      840
tgagggtcag atcccagata ctcactggca cctggagtga gtggagtcct agcatcacgt      900
ggtacaaccc aagtaatgaa atctgtgac tgagtgacct tgggggctgc ggtggtgagg       960
agagctcacg ggaatcctgg agcagtgtag ctggcgtgtc aaaagcagaa acgcaggaga     1020
tggacttcca gctgcccctg atacagcgcc ttccactggg ggtcaccatc tcctgcctct     1080
```

```
gcatcccgtt gttttgcctg ttctgttact tcagcattac caagattaag aagatatggt   1140
gggaccagat tcccacccca gcacgcagtc ccttggtggc catcatcatt caggatgcac   1200
aggtgcccct ctgggataag cagacccgaa gccaggagtc aaccaagtac ccgcactgga   1260
aaacttgtct agacaagctg ctgccttgct tgctgaagca cagagtaaag aagaagacag   1320
acttcccgaa ggctgcccca accaagtctc tccagagtcc tggaaaggca ggctggtgtc   1380
ccatggaggt cagcaggacc gtcctctggc cagagaatgt tagtgtcagt gtggtgcgct   1440
gtatggagct gttttgaggcc ccagtacaga atgtggagga ggaagaagat gagatagtca   1500
aagaggacct gagcatgtca cctgagaaca gcggaggctg cggcttccag gagagccagg   1560
cagacatcat ggctcggctc actgagaacc tgttttccga cttgttggag gctgagaatg   1620
ggggccttgg ccagtcagcc ttggcagagt catgctcccc tctgccttca ggaagtgggc   1680
aggcttctgt atcctgggcc tgcctcccca tggggcccag tgaggaggcc acatgccagg   1740
tcacagagca gccttcacac ccaggccctc tttcaggcag cccagcccag agtgcaccta   1800
ctctggcttg cacgcaggtc ccacttgtcc ttgcagacaa tcctgcctac cggagtttta   1860
gtgactgctg tagcccggcc ccaaatcctg agagctggc tccagagcag cagcaggctg   1920
atcatctgga agaagaggag cctccaagcc cggctgaccc ccattcttca gggccaccaa   1980
tgcagccagt ggagagctgg gagcagatcc ttcacatgag tgtcctgcag catggggcag   2040
ctgctggctc cacccagcc cctgccggtg gctaccagga gtttgtgcag gcagtgaagc   2100
agggtgccgc ccaggatcct gggggtgcctg tgtcaggcc ttctggagac cccggttaca   2160
aggccttctc gagcctgctc agcagcaatg catccgcgg ggacacagca gcagcgggga   2220
ctgacgatgg gcatggaggc tacaagccct tccagaatcc tgttcctaac cagtccccta   2280
gctccgtgcc cttatttact ttcggactag acacggagct gtcacccagt cctctgaact   2340
cagacccacc caaaagcccc ccagaatgcc ttggtctgga gctggggctc aaaggaggtg   2400
actgggtgaa ggcccctcct cctgcagatc aggtgcccaa gccctttggg gatgacctgg   2460
gctttggtat tgtgtactcg tccctcactt gccacttgtg tggccacctg aagcaacacc   2520
acagccagga ggaaggtggc cagagcccca tcgttgctag ccctggctgt ggctgctgct   2580
acgatgacag atcaccatcc ctgggggagcc tctcggggggc cttggaaagc tgtcctgagg   2640
gaataccacc agaagccaac ctcatgtcag cacccaagac accctcaaac ttgtcagggg   2700
agggcaaggg ccctggtcac tctcctgttc ccagccagac gaccgaggtg cctgtgggcg   2760
ccctgggcat tgctgtttct taggtgagtg agtgtgctgt tgttgctgag gtctgtgctg   2820
aggccagggt tcctccaagc cagggaagta cttcctggga gacagcccag ctggcaggtt   2880
tcccagaaat ccagagaatg gtgaattgaa gatgtaaact tggcctgacc ctggacgctc   2940
ggagcctggc tgtctcctct tccactggcc tgggctctcc tccctcccaa gggatacagg   3000
gctcactgt gcttggtccc acagcagtgc tgacgttcct aagtcctggg ctttcctagc   3060
tgatgttgtc ctacctactc agtcccattt tgtccaccga atagacctgt cactcaaggc   3120
tctcagcggt cctgccatag ctgctggacg ctcccagctg gaagctgggc ctagaaactc   3180
acagatggcc tggcagtggc atgggaggcc ctaaaaatta gtggaaattt tgagagagga   3240
caggtattgc cccacagagg ccattcattg aacagccagg actgggacta gaggcagagc   3300
ctgctgtcct ccgctcagtt gtagaaagca acaaggacac aaacttgatt gcccaaagtc   3360
actgccagtt acccacatat gaccagaagc cagggctcct gggatgtgga agataaacaa   3420
```

```
acacagttgc cgggtggcag ggccccagcg ggcacgataa ctggcagtca aggcgatacc    3480
tcgagggaac tgtggggctg gtcctggttg gtggtcaggt ggtagggata gcagatggca    3540
gactttggtg agtgagtgag tctgactgtg ttctggaaga tgggaccggg ctcagcactg    3600
tctgctcacg tccccactgt tgcaacacct agtctgtttg caaggaggac aggacaggtc    3660
acatggagct ttatgtcaat aaagtcttta tcttgtc                            3697

<210> SEQ ID NO 3
<211> LENGTH: 19
<212> TYPE: DNA
<213> ORGANISM: Artificial Sequence
<220> FEATURE:
<223> OTHER INFORMATION: Antisense Compound

<400> SEQUENCE: 3
aatggtccca ccaattgca                                                  19

<210> SEQ ID NO 4
<211> LENGTH: 23
<212> TYPE: DNA
<213> ORGANISM: Artificial Sequence
<220> FEATURE:
<223> OTHER INFORMATION: Antisense Compound

<400> SEQUENCE: 4
ctccgttgtt ctcagggata cac                                             23

<210> SEQ ID NO 5
<211> LENGTH: 21
<212> TYPE: DNA
<213> ORGANISM: Artificial Sequence
<220> FEATURE:
<223> OTHER INFORMATION: Antisense Compound

<400> SEQUENCE: 5
tttttctgct ctccgaagcc c                                               21

<210> SEQ ID NO 6
<211> LENGTH: 21
<212> TYPE: DNA
<213> ORGANISM: Artificial Sequence
<220> FEATURE:
<223> OTHER INFORMATION: Antisense Compound

<400> SEQUENCE: 6
tcccattttg tccaccgaat a                                               21

<210> SEQ ID NO 7
<211> LENGTH: 20
<212> TYPE: DNA
<213> ORGANISM: Artificial Sequence
<220> FEATURE:
<223> OTHER INFORMATION: Antisense Compound

<400> SEQUENCE: 7
gtttctaggc ccagcttcca                                                 20

<210> SEQ ID NO 8
<211> LENGTH: 25
<212> TYPE: DNA
<213> ORGANISM: Artificial Sequence
<220> FEATURE:
<223> OTHER INFORMATION: Antisense Compound

<400> SEQUENCE: 8
```
tgtcactcaa ggctctcagc ggtcc                                      25

<210> SEQ ID NO 9
<211> LENGTH: 20
<212> TYPE: DNA
<213> ORGANISM: Artificial Sequence
<220> FEATURE:
<223> OTHER INFORMATION: Antisense Compound

<400> SEQUENCE: 9
acccgcacaa ggtcctgggc                                            20

<210> SEQ ID NO 10
<211> LENGTH: 20
<212> TYPE: DNA
<213> ORGANISM: Artificial Sequence
<220> FEATURE:
<223> OTHER INFORMATION: Antisense Compound

<400> SEQUENCE: 10
caggtcttac cattaccact                                            20

<210> SEQ ID NO 11
<211> LENGTH: 20
<212> TYPE: DNA
<213> ORGANISM: Artificial Sequence
<220> FEATURE:
<223> OTHER INFORMATION: Antisense Compound

<400> SEQUENCE: 11
gcccactcac ttctgcaggg                                            20

<210> SEQ ID NO 12
<211> LENGTH: 20
<212> TYPE: DNA
<213> ORGANISM: Artificial Sequence
<220> FEATURE:
<223> OTHER INFORMATION: Antisense Compound

<400> SEQUENCE: 12
cggttgtacc acgtgatgct                                            20

<210> SEQ ID NO 13
<211> LENGTH: 20
<212> TYPE: DNA
<213> ORGANISM: Artificial Sequence
<220> FEATURE:
<223> OTHER INFORMATION: Antisense Compound

<400> SEQUENCE: 13
tgatactcac ggttgtacca                                            20

<210> SEQ ID NO 14
<211> LENGTH: 20
<212> TYPE: DNA
<213> ORGANISM: Artificial Sequence
<220> FEATURE:
<223> OTHER INFORMATION: Antisense Compound

<400> SEQUENCE: 14
aggaactcac ttggtaatgc                                            20

<210> SEQ ID NO 15
<211> LENGTH: 20
<212> TYPE: DNA

```
<213> ORGANISM: Artificial Sequence
<220> FEATURE:
<223> OTHER INFORMATION: Antisense Compound

<400> SEQUENCE: 15
tgtaccctct tacctgtgca                                                     20

<210> SEQ ID NO 16
<211> LENGTH: 20
<212> TYPE: DNA
<213> ORGANISM: Artificial Sequence
<220> FEATURE:
<223> OTHER INFORMATION: Antisense Compound

<400> SEQUENCE: 16
caaaaggtgc ctgcgagttc                                                     20

<210> SEQ ID NO 17
<211> LENGTH: 20
<212> TYPE: DNA
<213> ORGANISM: Artificial Sequence
<220> FEATURE:
<223> OTHER INFORMATION: Antisense Compound

<400> SEQUENCE: 17
ggctgggtta caggaacaag                                                     20

<210> SEQ ID NO 18
<211> LENGTH: 20
<212> TYPE: DNA
<213> ORGANISM: Artificial Sequence
<220> FEATURE:
<223> OTHER INFORMATION: Antisense Compound

<400> SEQUENCE: 18
agctggaagt ggttgtacca                                                     20

<210> SEQ ID NO 19
<211> LENGTH: 20
<212> TYPE: DNA
<213> ORGANISM: Artificial Sequence
<220> FEATURE:
<223> OTHER INFORMATION: Antisense Compound

<400> SEQUENCE: 19
aatcagaagc caggtccctc                                                     20

<210> SEQ ID NO 20
<211> LENGTH: 20
<212> TYPE: DNA
<213> ORGANISM: Artificial Sequence
<220> FEATURE:
<223> OTHER INFORMATION: Antisense Compound

<400> SEQUENCE: 20
caaaaggtgc ctgcacaagg                                                     20

<210> SEQ ID NO 21
<211> LENGTH: 20
<212> TYPE: DNA
<213> ORGANISM: Artificial Sequence
<220> FEATURE:
<223> OTHER INFORMATION: Antisense Compound

<400> SEQUENCE: 21
tgcaaagccg ccccattggg                                                     20
```

```
<210> SEQ ID NO 22
<211> LENGTH: 20
<212> TYPE: DNA
<213> ORGANISM: Artificial Sequence
<220> FEATURE:
<223> OTHER INFORMATION: Antisense Compound

<400> SEQUENCE: 22
caggaacttg gtgcaaagcc                                                    20

<210> SEQ ID NO 23
<211> LENGTH: 20
<212> TYPE: DNA
<213> ORGANISM: Artificial Sequence
<220> FEATURE:
<223> OTHER INFORMATION: Antisense Compound

<400> SEQUENCE: 23
tagtcagaga agcaggtggg                                                    20

<210> SEQ ID NO 24
<211> LENGTH: 20
<212> TYPE: DNA
<213> ORGANISM: Artificial Sequence
<220> FEATURE:
<223> OTHER INFORMATION: Antisense Compound

<400> SEQUENCE: 24
agtgcggatg tagtcagaga                                                    20

<210> SEQ ID NO 25
<211> LENGTH: 20
<212> TYPE: DNA
<213> ORGANISM: Artificial Sequence
<220> FEATURE:
<223> OTHER INFORMATION: Antisense Compound

<400> SEQUENCE: 25
ctgagaactg cagtccacag                                                    20

<210> SEQ ID NO 26
<211> LENGTH: 20
<212> TYPE: DNA
<213> ORGANISM: Artificial Sequence
<220> FEATURE:
<223> OTHER INFORMATION: Antisense Compound

<400> SEQUENCE: 26
gtgaggtttt cagagaactc                                                    20

<210> SEQ ID NO 27
<211> LENGTH: 20
<212> TYPE: DNA
<213> ORGANISM: Artificial Sequence
<220> FEATURE:
<223> OTHER INFORMATION: Antisense Compound

<400> SEQUENCE: 27
tgcatgtgag gttttcagag                                                    20

<210> SEQ ID NO 28
<211> LENGTH: 20
<212> TYPE: DNA
<213> ORGANISM: Artificial Sequence
<220> FEATURE:
```

-continued

<223> OTHER INFORMATION: Antisense Compound

<400> SEQUENCE: 28
gtgtgaggtt gtctggagct    20

<210> SEQ ID NO 29
<211> LENGTH: 20
<212> TYPE: DNA
<213> ORGANISM: Artificial Sequence
<220> FEATURE:
<223> OTHER INFORMATION: Antisense Compound

<400> SEQUENCE: 29
acattggtgt ggagtgtgag    20

<210> SEQ ID NO 30
<211> LENGTH: 20
<212> TYPE: DNA
<213> ORGANISM: Artificial Sequence
<220> FEATURE:
<223> OTHER INFORMATION: Antisense Compound

<400> SEQUENCE: 30
ctctggagat gttgaccatg    20

<210> SEQ ID NO 31
<211> LENGTH: 20
<212> TYPE: DNA
<213> ORGANISM: Artificial Sequence
<220> FEATURE:
<223> OTHER INFORMATION: Antisense Compound

<400> SEQUENCE: 31
gtcctctctg gagatgttga    20

<210> SEQ ID NO 32
<211> LENGTH: 20
<212> TYPE: DNA
<213> ORGANISM: Artificial Sequence
<220> FEATURE:
<223> OTHER INFORMATION: Antisense Compound

<400> SEQUENCE: 32
gggttgtcct ctctggagat    20

<210> SEQ ID NO 33
<211> LENGTH: 20
<212> TYPE: DNA
<213> ORGANISM: Artificial Sequence
<220> FEATURE:
<223> OTHER INFORMATION: Antisense Compound

<400> SEQUENCE: 33
tgtaggtcac attatagact    20

<210> SEQ ID NO 34
<211> LENGTH: 20
<212> TYPE: DNA
<213> ORGANISM: Artificial Sequence
<220> FEATURE:
<223> OTHER INFORMATION: Antisense Compound

<400> SEQUENCE: 34
gggttgtacc acgtgatgct    20

```
<210> SEQ ID NO 35
<211> LENGTH: 20
<212> TYPE: DNA
<213> ORGANISM: Artificial Sequence
<220> FEATURE:
<223> OTHER INFORMATION: Antisense Compound

<400> SEQUENCE: 35
tcactcagtc acagattttc                                              20

<210> SEQ ID NO 36
<211> LENGTH: 20
<212> TYPE: DNA
<213> ORGANISM: Artificial Sequence
<220> FEATURE:
<223> OTHER INFORMATION: Antisense Compound

<400> SEQUENCE: 36
agctggaagt ccatctcctg                                              20

<210> SEQ ID NO 37
<211> LENGTH: 20
<212> TYPE: DNA
<213> ORGANISM: Artificial Sequence
<220> FEATURE:
<223> OTHER INFORMATION: Antisense Compound

<400> SEQUENCE: 37
cttcttaatc ttggtaatgc                                              20

<210> SEQ ID NO 38
<211> LENGTH: 20
<212> TYPE: DNA
<213> ORGANISM: Artificial Sequence
<220> FEATURE:
<223> OTHER INFORMATION: Antisense Compound

<400> SEQUENCE: 38
accatatctt cttaatcttg                                              20

<210> SEQ ID NO 39
<211> LENGTH: 20
<212> TYPE: DNA
<213> ORGANISM: Artificial Sequence
<220> FEATURE:
<223> OTHER INFORMATION: Antisense Compound

<400> SEQUENCE: 39
gtcccaccat atcttcttaa                                              20

<210> SEQ ID NO 40
<211> LENGTH: 20
<212> TYPE: DNA
<213> ORGANISM: Artificial Sequence
<220> FEATURE:
<223> OTHER INFORMATION: Antisense Compound

<400> SEQUENCE: 40
atctggtccc accatatctt                                              20

<210> SEQ ID NO 41
<211> LENGTH: 20
<212> TYPE: DNA
<213> ORGANISM: Artificial Sequence
<220> FEATURE:
<223> OTHER INFORMATION: Antisense Compound
```

```
<400> SEQUENCE: 41
tgggaatctg gtcccaccat                                               20

<210> SEQ ID NO 42
<211> LENGTH: 20
<212> TYPE: DNA
<213> ORGANISM: Artificial Sequence
<220> FEATURE:
<223> OTHER INFORMATION: Antisense Compound

<400> SEQUENCE: 42
ggttgactcc tggcttcggg                                               20

<210> SEQ ID NO 43
<211> LENGTH: 20
<212> TYPE: DNA
<213> ORGANISM: Artificial Sequence
<220> FEATURE:
<223> OTHER INFORMATION: Antisense Compound

<400> SEQUENCE: 43
ggacggtcct gctgacctcc                                               20

<210> SEQ ID NO 44
<211> LENGTH: 20
<212> TYPE: DNA
<213> ORGANISM: Artificial Sequence
<220> FEATURE:
<223> OTHER INFORMATION: Antisense Compound

<400> SEQUENCE: 44
ccagaggacg gtcctgctga                                               20

<210> SEQ ID NO 45
<211> LENGTH: 20
<212> TYPE: DNA
<213> ORGANISM: Artificial Sequence
<220> FEATURE:
<223> OTHER INFORMATION: Antisense Compound

<400> SEQUENCE: 45
tctggccaga ggacggtcct                                               20

<210> SEQ ID NO 46
<211> LENGTH: 20
<212> TYPE: DNA
<213> ORGANISM: Artificial Sequence
<220> FEATURE:
<223> OTHER INFORMATION: Antisense Compound

<400> SEQUENCE: 46
tacagcgcac cacactgaca                                               20

<210> SEQ ID NO 47
<211> LENGTH: 20
<212> TYPE: DNA
<213> ORGANISM: Artificial Sequence
<220> FEATURE:
<223> OTHER INFORMATION: Antisense Compound

<400> SEQUENCE: 47
gctccataca gcgcaccaca                                               20

<210> SEQ ID NO 48
<211> LENGTH: 20
```

```
<212> TYPE: DNA
<213> ORGANISM: Artificial Sequence
<220> FEATURE:
<223> OTHER INFORMATION: Antisense Compound

<400> SEQUENCE: 48
aaacagctcc atacagcgca                                               20

<210> SEQ ID NO 49
<211> LENGTH: 20
<212> TYPE: DNA
<213> ORGANISM: Artificial Sequence
<220> FEATURE:
<223> OTHER INFORMATION: Antisense Compound

<400> SEQUENCE: 49
gcctcaaaca gctccataca                                               20

<210> SEQ ID NO 50
<211> LENGTH: 20
<212> TYPE: DNA
<213> ORGANISM: Artificial Sequence
<220> FEATURE:
<223> OTHER INFORMATION: Antisense Compound

<400> SEQUENCE: 50
cctccacatt ctgtactggg                                               20

<210> SEQ ID NO 51
<211> LENGTH: 20
<212> TYPE: DNA
<213> ORGANISM: Artificial Sequence
<220> FEATURE:
<223> OTHER INFORMATION: Antisense Compound

<400> SEQUENCE: 51
caggtgacat gctcaggtcc                                               20

<210> SEQ ID NO 52
<211> LENGTH: 20
<212> TYPE: DNA
<213> ORGANISM: Artificial Sequence
<220> FEATURE:
<223> OTHER INFORMATION: Antisense Compound

<400> SEQUENCE: 52
gttctcaggt gacatgctca                                               20

<210> SEQ ID NO 53
<211> LENGTH: 20
<212> TYPE: DNA
<213> ORGANISM: Artificial Sequence
<220> FEATURE:
<223> OTHER INFORMATION: Antisense Compound

<400> SEQUENCE: 53
ccgctgttct caggtgacat                                               20

<210> SEQ ID NO 54
<211> LENGTH: 20
<212> TYPE: DNA
<213> ORGANISM: Artificial Sequence
<220> FEATURE:
<223> OTHER INFORMATION: Antisense Compound

<400> SEQUENCE: 54
```

-continued aacaggttct cagtgagccg                                             20

<210> SEQ ID NO 55
<211> LENGTH: 20
<212> TYPE: DNA
<213> ORGANISM: Artificial Sequence
<220> FEATURE:
<223> OTHER INFORMATION: Antisense Compound

<400> SEQUENCE: 55
ccggtaggca ggattgtctg                                             20

<210> SEQ ID NO 56
<211> LENGTH: 20
<212> TYPE: DNA
<213> ORGANISM: Artificial Sequence
<220> FEATURE:
<223> OTHER INFORMATION: Antisense Compound

<400> SEQUENCE: 56
aaactccggt aggcaggatt                                             20

<210> SEQ ID NO 57
<211> LENGTH: 20
<212> TYPE: DNA
<213> ORGANISM: Artificial Sequence
<220> FEATURE:
<223> OTHER INFORMATION: Antisense Compound

<400> SEQUENCE: 57
cactaaaact ccggtaggca                                             20

<210> SEQ ID NO 58
<211> LENGTH: 20
<212> TYPE: DNA
<213> ORGANISM: Artificial Sequence
<220> FEATURE:
<223> OTHER INFORMATION: Antisense Compound

<400> SEQUENCE: 58
ccagctctcc aggatttggg                                             20

<210> SEQ ID NO 59
<211> LENGTH: 20
<212> TYPE: DNA
<213> ORGANISM: Artificial Sequence
<220> FEATURE:
<223> OTHER INFORMATION: Antisense Compound

<400> SEQUENCE: 59
tggtggccct gaagaatggg                                             20

<210> SEQ ID NO 60
<211> LENGTH: 20
<212> TYPE: DNA
<213> ORGANISM: Artificial Sequence
<220> FEATURE:
<223> OTHER INFORMATION: Antisense Compound

<400> SEQUENCE: 60
ggatctgctc ccagctctcc                                             20

<210> SEQ ID NO 61
<211> LENGTH: 20
<212> TYPE: DNA
<213> ORGANISM: Artificial Sequence

```
<220> FEATURE:
<223> OTHER INFORMATION: Antisense Compound

<400> SEQUENCE: 61
gtgaaggatc tgctcccagc                                               20

<210> SEQ ID NO 62
<211> LENGTH: 20
<212> TYPE: DNA
<213> ORGANISM: Artificial Sequence
<220> FEATURE:
<223> OTHER INFORMATION: Antisense Compound

<400> SEQUENCE: 62
ctcatgtgaa ggatctgctc                                               20

<210> SEQ ID NO 63
<211> LENGTH: 20
<212> TYPE: DNA
<213> ORGANISM: Artificial Sequence
<220> FEATURE:
<223> OTHER INFORMATION: Antisense Compound

<400> SEQUENCE: 63
ggacactcat gtgaaggatc                                               20

<210> SEQ ID NO 64
<211> LENGTH: 20
<212> TYPE: DNA
<213> ORGANISM: Artificial Sequence
<220> FEATURE:
<223> OTHER INFORMATION: Antisense Compound

<400> SEQUENCE: 64
ctgcaggaca ctcatgtgaa                                               20

<210> SEQ ID NO 65
<211> LENGTH: 20
<212> TYPE: DNA
<213> ORGANISM: Artificial Sequence
<220> FEATURE:
<223> OTHER INFORMATION: Antisense Compound

<400> SEQUENCE: 65
ttcactgcct gcacaaactc                                               20

<210> SEQ ID NO 66
<211> LENGTH: 20
<212> TYPE: DNA
<213> ORGANISM: Artificial Sequence
<220> FEATURE:
<223> OTHER INFORMATION: Antisense Compound

<400> SEQUENCE: 66
cctgcttcac tgcctgcaca                                               20

<210> SEQ ID NO 67
<211> LENGTH: 20
<212> TYPE: DNA
<213> ORGANISM: Artificial Sequence
<220> FEATURE:
<223> OTHER INFORMATION: Antisense Compound

<400> SEQUENCE: 67
ctgctgagca ggctcgagaa                                               20
```

-continued

<210> SEQ ID NO 68
<211> LENGTH: 20
<212> TYPE: DNA
<213> ORGANISM: Artificial Sequence
<220> FEATURE:
<223> OTHER INFORMATION: Antisense Compound

<400> SEQUENCE: 68
gtcatcccca aagggcttgg                                               20

<210> SEQ ID NO 69
<211> LENGTH: 20
<212> TYPE: DNA
<213> ORGANISM: Artificial Sequence
<220> FEATURE:
<223> OTHER INFORMATION: Antisense Compound

<400> SEQUENCE: 69
cccaggtcat ccccaaggg                                                20

<210> SEQ ID NO 70
<211> LENGTH: 20
<212> TYPE: DNA
<213> ORGANISM: Artificial Sequence
<220> FEATURE:
<223> OTHER INFORMATION: Antisense Compound

<400> SEQUENCE: 70
gtgagggacg agtacacaat                                               20

<210> SEQ ID NO 71
<211> LENGTH: 20
<212> TYPE: DNA
<213> ORGANISM: Artificial Sequence
<220> FEATURE:
<223> OTHER INFORMATION: Antisense Compound

<400> SEQUENCE: 71
ttgcttcagg tggccacaca                                               20

<210> SEQ ID NO 72
<211> LENGTH: 20
<212> TYPE: DNA
<213> ORGANISM: Artificial Sequence
<220> FEATURE:
<223> OTHER INFORMATION: Antisense Compound

<400> SEQUENCE: 72
tggtgttgct tcaggtggcc                                               20

<210> SEQ ID NO 73
<211> LENGTH: 20
<212> TYPE: DNA
<213> ORGANISM: Artificial Sequence
<220> FEATURE:
<223> OTHER INFORMATION: Antisense Compound

<400> SEQUENCE: 73
ggctgtggtg ttgcttcagg                                               20

<210> SEQ ID NO 74
<211> LENGTH: 20
<212> TYPE: DNA
<213> ORGANISM: Artificial Sequence
<220> FEATURE:
<223> OTHER INFORMATION: Antisense Compound

<400> SEQUENCE: 74
ctggctggga acaggagagt                                               20

<210> SEQ ID NO 75
<211> LENGTH: 20
<212> TYPE: DNA
<213> ORGANISM: Artificial Sequence
<220> FEATURE:
<223> OTHER INFORMATION: Antisense Compound

<400> SEQUENCE: 75
agcaacaaca gcacactcac                                               20

<210> SEQ ID NO 76
<211> LENGTH: 20
<212> TYPE: DNA
<213> ORGANISM: Artificial Sequence
<220> FEATURE:
<223> OTHER INFORMATION: Antisense Compound

<400> SEQUENCE: 76
acctcagcaa caacagcaca                                               20

<210> SEQ ID NO 77
<211> LENGTH: 20
<212> TYPE: DNA
<213> ORGANISM: Artificial Sequence
<220> FEATURE:
<223> OTHER INFORMATION: Antisense Compound

<400> SEQUENCE: 77
cacagacctc agcaacaaca                                               20

<210> SEQ ID NO 78
<211> LENGTH: 20
<212> TYPE: DNA
<213> ORGANISM: Artificial Sequence
<220> FEATURE:
<223> OTHER INFORMATION: Antisense Compound

<400> SEQUENCE: 78
tccctggctt ggaggaaccc                                               20

<210> SEQ ID NO 79
<211> LENGTH: 20
<212> TYPE: DNA
<213> ORGANISM: Artificial Sequence
<220> FEATURE:
<223> OTHER INFORMATION: Antisense Compound

<400> SEQUENCE: 79
cctgccagct gggctgtctc                                               20

<210> SEQ ID NO 80
<211> LENGTH: 20
<212> TYPE: DNA
<213> ORGANISM: Artificial Sequence
<220> FEATURE:
<223> OTHER INFORMATION: Antisense Compound

<400> SEQUENCE: 80
ttctgggaaa cctgccagct                                               20

<210> SEQ ID NO 81

```
<211> LENGTH: 20
<212> TYPE: DNA
<213> ORGANISM: Artificial Sequence
<220> FEATURE:
<223> OTHER INFORMATION: Antisense Compound

<400> SEQUENCE: 81
actttgggca atcaagtttg                                               20

<210> SEQ ID NO 82
<211> LENGTH: 20
<212> TYPE: DNA
<213> ORGANISM: Artificial Sequence
<220> FEATURE:
<223> OTHER INFORMATION: Antisense Compound

<400> SEQUENCE: 82
cagtgacttt gggcaatcaa                                               20

<210> SEQ ID NO 83
<211> LENGTH: 20
<212> TYPE: DNA
<213> ORGANISM: Artificial Sequence
<220> FEATURE:
<223> OTHER INFORMATION: Antisense Compound

<400> SEQUENCE: 83
actggcagtg actttgggca                                               20

<210> SEQ ID NO 84
<211> LENGTH: 20
<212> TYPE: DNA
<213> ORGANISM: Artificial Sequence
<220> FEATURE:
<223> OTHER INFORMATION: Antisense Compound

<400> SEQUENCE: 84
gggtaactgg cagtgacttt                                               20

<210> SEQ ID NO 85
<211> LENGTH: 20
<212> TYPE: DNA
<213> ORGANISM: Artificial Sequence
<220> FEATURE:
<223> OTHER INFORMATION: Antisense Compound

<400> SEQUENCE: 85
taaagacttt attgacataa                                               20

<210> SEQ ID NO 86
<211> LENGTH: 20
<212> TYPE: DNA
<213> ORGANISM: Artificial Sequence
<220> FEATURE:
<223> OTHER INFORMATION: Antisense Compound

<400> SEQUENCE: 86
gacaagataa agactttatt                                               20

<210> SEQ ID NO 87
<211> LENGTH: 20
<212> TYPE: DNA
<213> ORGANISM: Artificial Sequence
<220> FEATURE:
<223> OTHER INFORMATION: Antisense Compound

<400> SEQUENCE: 87
```

-continued

```
gtaaatcttt aattatctgc                                               20

<210> SEQ ID NO 88
<211> LENGTH: 20
<212> TYPE: DNA
<213> ORGANISM: Artificial Sequence
<220> FEATURE:
<223> OTHER INFORMATION: Antisense Compound

<400> SEQUENCE: 88
catgttccca gagcttgcca                                               20

<210> SEQ ID NO 89
<211> LENGTH: 20
<212> TYPE: DNA
<213> ORGANISM: Artificial Sequence
<220> FEATURE:
<223> OTHER INFORMATION: Antisense Compound

<400> SEQUENCE: 89
ctgcaagacc ttcatgttcc                                               20

<210> SEQ ID NO 90
<211> LENGTH: 20
<212> TYPE: DNA
<213> ORGANISM: Artificial Sequence
<220> FEATURE:
<223> OTHER INFORMATION: Antisense Compound

<400> SEQUENCE: 90
caagtagaga tgctcatgta                                               20

<210> SEQ ID NO 91
<211> LENGTH: 20
<212> TYPE: DNA
<213> ORGANISM: Artificial Sequence
<220> FEATURE:
<223> OTHER INFORMATION: Antisense Compound

<400> SEQUENCE: 91
caattggtgg gaccattcat                                               20

<210> SEQ ID NO 92
<211> LENGTH: 20
<212> TYPE: DNA
<213> ORGANISM: Artificial Sequence
<220> FEATURE:
<223> OTHER INFORMATION: Antisense Compound

<400> SEQUENCE: 92
acagcagctg ctgcccagcc                                               20

<210> SEQ ID NO 93
<211> LENGTH: 20
<212> TYPE: DNA
<213> ORGANISM: Artificial Sequence
<220> FEATURE:
<223> OTHER INFORMATION: Antisense Compound

<400> SEQUENCE: 93
aatcccagac ttcagggtgc                                               20

<210> SEQ ID NO 94
<211> LENGTH: 20
<212> TYPE: DNA
```

```
<213> ORGANISM: Artificial Sequence
<220> FEATURE:
<223> OTHER INFORMATION: Antisense Compound

<400> SEQUENCE: 94
gcactgagcc caggccctca                                                    20

<210> SEQ ID NO 95
<211> LENGTH: 20
<212> TYPE: DNA
<213> ORGANISM: Artificial Sequence
<220> FEATURE:
<223> OTHER INFORMATION: Antisense Compound

<400> SEQUENCE: 95
ctgacatagc acaacaggca                                                    20

<210> SEQ ID NO 96
<211> LENGTH: 20
<212> TYPE: DNA
<213> ORGANISM: Artificial Sequence
<220> FEATURE:
<223> OTHER INFORMATION: Antisense Compound

<400> SEQUENCE: 96
taatcttggt gatgctgaca                                                    20

<210> SEQ ID NO 97
<211> LENGTH: 20
<212> TYPE: DNA
<213> ORGANISM: Artificial Sequence
<220> FEATURE:
<223> OTHER INFORMATION: Antisense Compound

<400> SEQUENCE: 97
tttcttaatc ttggtgatgc                                                    20

<210> SEQ ID NO 98
<211> LENGTH: 20
<212> TYPE: DNA
<213> ORGANISM: Artificial Sequence
<220> FEATURE:
<223> OTHER INFORMATION: Antisense Compound

<400> SEQUENCE: 98
ccctggaaag gcatctcttt                                                    20

<210> SEQ ID NO 99
<211> LENGTH: 20
<212> TYPE: DNA
<213> ORGANISM: Artificial Sequence
<220> FEATURE:
<223> OTHER INFORMATION: Antisense Compound

<400> SEQUENCE: 99
gctgattttc cagagccctg                                                    20

<210> SEQ ID NO 100
<211> LENGTH: 20
<212> TYPE: DNA
<213> ORGANISM: Artificial Sequence
<220> FEATURE:
<223> OTHER INFORMATION: Antisense Compound

<400> SEQUENCE: 100
gcaccatgct gattttccag                                                    20
```

```
<210> SEQ ID NO 101
<211> LENGTH: 20
<212> TYPE: DNA
<213> ORGANISM: Artificial Sequence
<220> FEATURE:
<223> OTHER INFORMATION: Antisense Compound

<400> SEQUENCE: 101
cccagggcat gtgagcactc                                               20

<210> SEQ ID NO 102
<211> LENGTH: 20
<212> TYPE: DNA
<213> ORGANISM: Artificial Sequence
<220> FEATURE:
<223> OTHER INFORMATION: Antisense Compound

<400> SEQUENCE: 102
aactcatccc agggcatgtg                                               20

<210> SEQ ID NO 103
<211> LENGTH: 20
<212> TYPE: DNA
<213> ORGANISM: Artificial Sequence
<220> FEATURE:
<223> OTHER INFORMATION: Antisense Compound

<400> SEQUENCE: 103
tgcacttggg aactcatccc                                               20

<210> SEQ ID NO 104
<211> LENGTH: 20
<212> TYPE: DNA
<213> ORGANISM: Artificial Sequence
<220> FEATURE:
<223> OTHER INFORMATION: Antisense Compound

<400> SEQUENCE: 104
gcaagtcagg ttgtctggac                                               20

<210> SEQ ID NO 105
<211> LENGTH: 20
<212> TYPE: DNA
<213> ORGANISM: Artificial Sequence
<220> FEATURE:
<223> OTHER INFORMATION: Antisense Compound

<400> SEQUENCE: 105
gtgggtctgg acccagctct                                               20

<210> SEQ ID NO 106
<211> LENGTH: 20
<212> TYPE: DNA
<213> ORGANISM: Artificial Sequence
<220> FEATURE:
<223> OTHER INFORMATION: Antisense Compound

<400> SEQUENCE: 106
ggccagcagt gggtctggac                                               20

<210> SEQ ID NO 107
<211> LENGTH: 20
<212> TYPE: DNA
<213> ORGANISM: Artificial Sequence
<220> FEATURE:
```

<223> OTHER INFORMATION: Antisense Compound

<400> SEQUENCE: 107
tgccccatgc tggaggacat                                               20

<210> SEQ ID NO 108
<211> LENGTH: 20
<212> TYPE: DNA
<213> ORGANISM: Artificial Sequence
<220> FEATURE:
<223> OTHER INFORMATION: Antisense Compound

<400> SEQUENCE: 108
gagaaggcct tgtaaccagc                                               20

<210> SEQ ID NO 109
<211> LENGTH: 20
<212> TYPE: DNA
<213> ORGANISM: Artificial Sequence
<220> FEATURE:
<223> OTHER INFORMATION: Antisense Compound

<400> SEQUENCE: 109
acagcactgc tggcaagcag                                               20

<210> SEQ ID NO 110
<211> LENGTH: 20
<212> TYPE: DNA
<213> ORGANISM: Artificial Sequence
<220> FEATURE:
<223> OTHER INFORMATION: Antisense Compound

<400> SEQUENCE: 110
ccccactgct agccccaaac                                               20

<210> SEQ ID NO 111
<211> LENGTH: 20
<212> TYPE: DNA
<213> ORGANISM: Artificial Sequence
<220> FEATURE:
<223> OTHER INFORMATION: Antisense Compound

<400> SEQUENCE: 111
ctcttcccca ctgctagccc                                               20

<210> SEQ ID NO 112
<211> LENGTH: 20
<212> TYPE: DNA
<213> ORGANISM: Artificial Sequence
<220> FEATURE:
<223> OTHER INFORMATION: Antisense Compound

<400> SEQUENCE: 112
gaaaggctta taccctctt                                                20

<210> SEQ ID NO 113
<211> LENGTH: 20
<212> TYPE: DNA
<213> ORGANISM: Artificial Sequence
<220> FEATURE:
<223> OTHER INFORMATION: Antisense Compound

<400> SEQUENCE: 113
gaggtcttgg aaaggcttat                                               20

```
<210> SEQ ID NO 114
<211> LENGTH: 20
<212> TYPE: DNA
<213> ORGANISM: Artificial Sequence
<220> FEATURE:
<223> OTHER INFORMATION: Antisense Compound

<400> SEQUENCE: 114
agggcagcca ggaatgaggt                                               20

<210> SEQ ID NO 115
<211> LENGTH: 20
<212> TYPE: DNA
<213> ORGANISM: Artificial Sequence
<220> FEATURE:
<223> OTHER INFORMATION: Antisense Compound

<400> SEQUENCE: 115
tccccagggc agccaggaat                                               20

<210> SEQ ID NO 116
<211> LENGTH: 20
<212> TYPE: DNA
<213> ORGANISM: Artificial Sequence
<220> FEATURE:
<223> OTHER INFORMATION: Antisense Compound

<400> SEQUENCE: 116
gctttggcat gtcctctacc                                               20

<210> SEQ ID NO 117
<211> LENGTH: 20
<212> TYPE: DNA
<213> ORGANISM: Artificial Sequence
<220> FEATURE:
<223> OTHER INFORMATION: Antisense Compound

<400> SEQUENCE: 117
ggctgagtag acaatgccac                                               20

<210> SEQ ID NO 118
<211> LENGTH: 20
<212> TYPE: DNA
<213> ORGANISM: Artificial Sequence
<220> FEATURE:
<223> OTHER INFORMATION: Antisense Compound

<400> SEQUENCE: 118
aggtggcagg taagggctga                                               20

<210> SEQ ID NO 119
<211> LENGTH: 20
<212> TYPE: DNA
<213> ORGANISM: Artificial Sequence
<220> FEATURE:
<223> OTHER INFORMATION: Antisense Compound

<400> SEQUENCE: 119
ccacagcaag gactggccat                                               20

<210> SEQ ID NO 120
<211> LENGTH: 20
<212> TYPE: DNA
<213> ORGANISM: Artificial Sequence
<220> FEATURE:
<223> OTHER INFORMATION: Antisense Compound
```

```
<400> SEQUENCE: 120
cagtggaacc ccacctggag                                              20

<210> SEQ ID NO 121
<211> LENGTH: 20
<212> TYPE: DNA
<213> ORGANISM: Artificial Sequence
<220> FEATURE:
<223> OTHER INFORMATION: Antisense Compound

<400> SEQUENCE: 121
gaaggatgat gaggatttac                                              20

<210> SEQ ID NO 122
<211> LENGTH: 20
<212> TYPE: DNA
<213> ORGANISM: Artificial Sequence
<220> FEATURE:
<223> OTHER INFORMATION: Antisense Compound

<400> SEQUENCE: 122
caggatggaa ggatgatgag                                              20

<210> SEQ ID NO 123
<211> LENGTH: 20
<212> TYPE: DNA
<213> ORGANISM: Artificial Sequence
<220> FEATURE:
<223> OTHER INFORMATION: Antisense Compound

<400> SEQUENCE: 123
agctctgagc attgccaggg                                              20

<210> SEQ ID NO 124
<211> LENGTH: 20
<212> TYPE: DNA
<213> ORGANISM: Artificial Sequence
<220> FEATURE:
<223> OTHER INFORMATION: Antisense Compound

<400> SEQUENCE: 124
ccctcatgta tgtgggtccc                                              20

<210> SEQ ID NO 125
<211> LENGTH: 20
<212> TYPE: DNA
<213> ORGANISM: Artificial Sequence
<220> FEATURE:
<223> OTHER INFORMATION: Antisense Compound

<400> SEQUENCE: 125
gacatgcacc taagagaccc                                              20

<210> SEQ ID NO 126
<211> LENGTH: 20
<212> TYPE: DNA
<213> ORGANISM: Artificial Sequence
<220> FEATURE:
<223> OTHER INFORMATION: Antisense Compound

<400> SEQUENCE: 126
tagtcctcat ctgcagactc                                              20

<210> SEQ ID NO 127
<211> LENGTH: 20
```

```
<212> TYPE: DNA
<213> ORGANISM: Artificial Sequence
<220> FEATURE:
<223> OTHER INFORMATION: Antisense Compound

<400> SEQUENCE: 127
aatctgccag cctggctgcc                                              20

<210> SEQ ID NO 128
<211> LENGTH: 20
<212> TYPE: DNA
<213> ORGANISM: Artificial Sequence
<220> FEATURE:
<223> OTHER INFORMATION: Antisense Compound

<400> SEQUENCE: 128
ggttcttcaa gtcttttgga                                              20

<210> SEQ ID NO 129
<211> LENGTH: 20
<212> TYPE: DNA
<213> ORGANISM: Artificial Sequence
<220> FEATURE:
<223> OTHER INFORMATION: Antisense Compound

<400> SEQUENCE: 129
ggccaatcac cttcatacca                                              20

<210> SEQ ID NO 130
<211> LENGTH: 20
<212> TYPE: DNA
<213> ORGANISM: Artificial Sequence
<220> FEATURE:
<223> OTHER INFORMATION: Antisense Compound

<400> SEQUENCE: 130
gagcccagcc caatgctggg                                              20

<210> SEQ ID NO 131
<211> LENGTH: 20
<212> TYPE: DNA
<213> ORGANISM: Artificial Sequence
<220> FEATURE:
<223> OTHER INFORMATION: Antisense Compound

<400> SEQUENCE: 131
ctactctcat gggatgtggc                                              20

<210> SEQ ID NO 132
<211> LENGTH: 20
<212> TYPE: DNA
<213> ORGANISM: Artificial Sequence
<220> FEATURE:
<223> OTHER INFORMATION: Antisense Compound

<400> SEQUENCE: 132
gccctctact ctcatgggat                                              20

<210> SEQ ID NO 133
<211> LENGTH: 20
<212> TYPE: DNA
<213> ORGANISM: Artificial Sequence
<220> FEATURE:
<223> OTHER INFORMATION: Antisense Compound

<400> SEQUENCE: 133
```
ggcctcagtt ttcctgcagg    20

<210> SEQ ID NO 134
<211> LENGTH: 20
<212> TYPE: DNA
<213> ORGANISM: Artificial Sequence
<220> FEATURE:
<223> OTHER INFORMATION: Antisense Compound

<400> SEQUENCE: 134
cccaagggcc tcagttttcc    20

<210> SEQ ID NO 135
<211> LENGTH: 20
<212> TYPE: DNA
<213> ORGANISM: Artificial Sequence
<220> FEATURE:
<223> OTHER INFORMATION: Antisense Compound

<400> SEQUENCE: 135
gagggagcag ccaacaactc    20

<210> SEQ ID NO 136
<211> LENGTH: 20
<212> TYPE: DNA
<213> ORGANISM: Artificial Sequence
<220> FEATURE:
<223> OTHER INFORMATION: Antisense Compound

<400> SEQUENCE: 136
agacagaggc aggtgggcct    20

<210> SEQ ID NO 137
<211> LENGTH: 20
<212> TYPE: DNA
<213> ORGANISM: Artificial Sequence
<220> FEATURE:
<223> OTHER INFORMATION: Antisense Compound

<400> SEQUENCE: 137
cagtgagaca gaggcaggtg    20

<210> SEQ ID NO 138
<211> LENGTH: 20
<212> TYPE: DNA
<213> ORGANISM: Artificial Sequence
<220> FEATURE:
<223> OTHER INFORMATION: Antisense Compound

<400> SEQUENCE: 138
caagtcattc ccttgatggc    20

<210> SEQ ID NO 139
<211> LENGTH: 20
<212> TYPE: DNA
<213> ORGANISM: Artificial Sequence
<220> FEATURE:
<223> OTHER INFORMATION: Antisense Compound

<400> SEQUENCE: 139
atcaacctaa ggaagctctg    20

<210> SEQ ID NO 140
<211> LENGTH: 20
<212> TYPE: DNA
<213> ORGANISM: Artificial Sequence

```
<220> FEATURE:
<223> OTHER INFORMATION: Antisense Compound

<400> SEQUENCE: 140
taactgaaca ccccttgaca                                              20

<210> SEQ ID NO 141
<211> LENGTH: 20
<212> TYPE: DNA
<213> ORGANISM: Artificial Sequence
<220> FEATURE:
<223> OTHER INFORMATION: Antisense Compound

<400> SEQUENCE: 141
aattgtccct gctttagtca                                              20

<210> SEQ ID NO 142
<211> LENGTH: 20
<212> TYPE: DNA
<213> ORGANISM: Artificial Sequence
<220> FEATURE:
<223> OTHER INFORMATION: Antisense Compound

<400> SEQUENCE: 142
ggcagcaaat tgtccctgct                                              20

<210> SEQ ID NO 143
<211> LENGTH: 20
<212> TYPE: DNA
<213> ORGANISM: Artificial Sequence
<220> FEATURE:
<223> OTHER INFORMATION: Antisense Compound

<400> SEQUENCE: 143
gtgtttggca gcaaattgtc                                              20

<210> SEQ ID NO 144
<211> LENGTH: 20
<212> TYPE: DNA
<213> ORGANISM: Artificial Sequence
<220> FEATURE:
<223> OTHER INFORMATION: Antisense Compound

<400> SEQUENCE: 144
gggtaactgg tgccttatgc                                              20

<210> SEQ ID NO 145
<211> LENGTH: 20
<212> TYPE: DNA
<213> ORGANISM: Artificial Sequence
<220> FEATURE:
<223> OTHER INFORMATION: Antisense Compound

<400> SEQUENCE: 145
ggccaacatg cagggtaact                                              20

<210> SEQ ID NO 146
<211> LENGTH: 20
<212> TYPE: DNA
<213> ORGANISM: Artificial Sequence
<220> FEATURE:
<223> OTHER INFORMATION: Antisense Compound

<400> SEQUENCE: 146
attactcaac ccaaggttcc                                              20
```

```
<210> SEQ ID NO 147
<211> LENGTH: 20
<212> TYPE: DNA
<213> ORGANISM: Artificial Sequence
<220> FEATURE:
<223> OTHER INFORMATION: Antisense Compound

<400> SEQUENCE: 147
aagaaacttt atttatacaa                                              20

<210> SEQ ID NO 148
<211> LENGTH: 20
<212> TYPE: DNA
<213> ORGANISM: Artificial Sequence
<220> FEATURE:
<223> OTHER INFORMATION: Antisense Compound

<400> SEQUENCE: 148
gagacaaaga aactttattt                                              20

<210> SEQ ID NO 149
<211> LENGTH: 20
<212> TYPE: DNA
<213> ORGANISM: Artificial Sequence
<220> FEATURE:
<223> OTHER INFORMATION: Antisense Compound

<400> SEQUENCE: 149
cctagaattc agtcttccct                                              20

<210> SEQ ID NO 150
<211> LENGTH: 20
<212> TYPE: DNA
<213> ORGANISM: Artificial Sequence
<220> FEATURE:
<223> OTHER INFORMATION: Antisense Compound

<400> SEQUENCE: 150
gtttccatct agagtactag                                              20

<210> SEQ ID NO 151
<211> LENGTH: 20
<212> TYPE: DNA
<213> ORGANISM: Artificial Sequence
<220> FEATURE:
<223> OTHER INFORMATION: Antisense Compound

<400> SEQUENCE: 151
gccaaggcac ctgcagagag                                              20

<210> SEQ ID NO 152
<211> LENGTH: 20
<212> TYPE: DNA
<213> ORGANISM: Artificial Sequence
<220> FEATURE:
<223> OTHER INFORMATION: Antisense Compound

<400> SEQUENCE: 152
agtgagtggc agagtcagga                                              20

<210> SEQ ID NO 153
<211> LENGTH: 20
<212> TYPE: DNA
<213> ORGANISM: Artificial Sequence
<220> FEATURE:
<223> OTHER INFORMATION: Antisense Compound
```

<400> SEQUENCE: 153
cttccagtgt ctgcaaaagc                                                    20

<210> SEQ ID NO 154
<211> LENGTH: 20
<212> TYPE: DNA
<213> ORGANISM: Artificial Sequence
<220> FEATURE:
<223> OTHER INFORMATION: Antisense Compound

<400> SEQUENCE: 154
agccacccca ttgggagatg                                                    20

<210> SEQ ID NO 155
<211> LENGTH: 20
<212> TYPE: DNA
<213> ORGANISM: Artificial Sequence
<220> FEATURE:
<223> OTHER INFORMATION: Antisense Compound

<400> SEQUENCE: 155
gagcaaagcc accccattgg                                                    20

<210> SEQ ID NO 156
<211> LENGTH: 20
<212> TYPE: DNA
<213> ORGANISM: Artificial Sequence
<220> FEATURE:
<223> OTHER INFORMATION: Antisense Compound

<400> SEQUENCE: 156
ccagagcaaa gccaccccat                                                    20

<210> SEQ ID NO 157
<211> LENGTH: 20
<212> TYPE: DNA
<213> ORGANISM: Artificial Sequence
<220> FEATURE:
<223> OTHER INFORMATION: Antisense Compound

<400> SEQUENCE: 157
tcacagggaa caggagccca                                                    20

<210> SEQ ID NO 158
<211> LENGTH: 20
<212> TYPE: DNA
<213> ORGANISM: Artificial Sequence
<220> FEATURE:
<223> OTHER INFORMATION: Antisense Compound

<400> SEQUENCE: 158
ctcacaggga acaggagccc                                                    20

<210> SEQ ID NO 159
<211> LENGTH: 20
<212> TYPE: DNA
<213> ORGANISM: Artificial Sequence
<220> FEATURE:
<223> OTHER INFORMATION: Antisense Compound

<400> SEQUENCE: 159
agctcacagg gaacaggagc                                                    20

<210> SEQ ID NO 160

```
<211> LENGTH: 20
<212> TYPE: DNA
<213> ORGANISM: Artificial Sequence
<220> FEATURE:
<223> OTHER INFORMATION: Antisense Compound

<400> SEQUENCE: 160
cagctcacag ggaacaggag                                               20

<210> SEQ ID NO 161
<211> LENGTH: 20
<212> TYPE: DNA
<213> ORGANISM: Artificial Sequence
<220> FEATURE:
<223> OTHER INFORMATION: Antisense Compound

<400> SEQUENCE: 161
ggcagctcac agggaacagg                                               20

<210> SEQ ID NO 162
<211> LENGTH: 20
<212> TYPE: DNA
<213> ORGANISM: Artificial Sequence
<220> FEATURE:
<223> OTHER INFORMATION: Antisense Compound

<400> SEQUENCE: 162
aggcagctca cagggaacag                                               20

<210> SEQ ID NO 163
<211> LENGTH: 20
<212> TYPE: DNA
<213> ORGANISM: Artificial Sequence
<220> FEATURE:
<223> OTHER INFORMATION: Antisense Compound

<400> SEQUENCE: 163
caggcagctc acagggaaca                                               20

<210> SEQ ID NO 164
<211> LENGTH: 20
<212> TYPE: DNA
<213> ORGANISM: Artificial Sequence
<220> FEATURE:
<223> OTHER INFORMATION: Antisense Compound

<400> SEQUENCE: 164
ccaggcagct cacagggaac                                               20

<210> SEQ ID NO 165
<211> LENGTH: 20
<212> TYPE: DNA
<213> ORGANISM: Artificial Sequence
<220> FEATURE:
<223> OTHER INFORMATION: Antisense Compound

<400> SEQUENCE: 165
accaggcagc tcacagggaa                                               20

<210> SEQ ID NO 166
<211> LENGTH: 20
<212> TYPE: DNA
<213> ORGANISM: Artificial Sequence
<220> FEATURE:
<223> OTHER INFORMATION: Antisense Compound

<400> SEQUENCE: 166
```

```
ggaccaggca gctcacaggg                                              20

<210> SEQ ID NO 167
<211> LENGTH: 20
<212> TYPE: DNA
<213> ORGANISM: Artificial Sequence
<220> FEATURE:
<223> OTHER INFORMATION: Antisense Compound

<400> SEQUENCE: 167
aggaccaggc agctcacagg                                              20

<210> SEQ ID NO 168
<211> LENGTH: 20
<212> TYPE: DNA
<213> ORGANISM: Artificial Sequence
<220> FEATURE:
<223> OTHER INFORMATION: Antisense Compound

<400> SEQUENCE: 168
caggaccagg cagctcacag                                              20

<210> SEQ ID NO 169
<211> LENGTH: 20
<212> TYPE: DNA
<213> ORGANISM: Artificial Sequence
<220> FEATURE:
<223> OTHER INFORMATION: Antisense Compound

<400> SEQUENCE: 169
gcaggaccag gcagctcaca                                              20

<210> SEQ ID NO 170
<211> LENGTH: 20
<212> TYPE: DNA
<213> ORGANISM: Artificial Sequence
<220> FEATURE:
<223> OTHER INFORMATION: Antisense Compound

<400> SEQUENCE: 170
agcaggacca ggcagctcac                                              20

<210> SEQ ID NO 171
<211> LENGTH: 20
<212> TYPE: DNA
<213> ORGANISM: Artificial Sequence
<220> FEATURE:
<223> OTHER INFORMATION: Antisense Compound

<400> SEQUENCE: 171
cagcaggacc aggcagctca                                              20

<210> SEQ ID NO 172
<211> LENGTH: 20
<212> TYPE: DNA
<213> ORGANISM: Artificial Sequence
<220> FEATURE:
<223> OTHER INFORMATION: Antisense Compound

<400> SEQUENCE: 172
gcagcaggac caggcagctc                                              20

<210> SEQ ID NO 173
<211> LENGTH: 20
<212> TYPE: DNA
```

```
<213> ORGANISM: Artificial Sequence
<220> FEATURE:
<223> OTHER INFORMATION: Antisense Compound

<400> SEQUENCE: 173
tgcagcagga ccaggcagct                                              20

<210> SEQ ID NO 174
<211> LENGTH: 20
<212> TYPE: DNA
<213> ORGANISM: Artificial Sequence
<220> FEATURE:
<223> OTHER INFORMATION: Antisense Compound

<400> SEQUENCE: 174
ctgcagcagg accaggcagc                                              20

<210> SEQ ID NO 175
<211> LENGTH: 20
<212> TYPE: DNA
<213> ORGANISM: Artificial Sequence
<220> FEATURE:
<223> OTHER INFORMATION: Antisense Compound

<400> SEQUENCE: 175
acctgcagca ggaccaggca                                              20

<210> SEQ ID NO 176
<211> LENGTH: 20
<212> TYPE: DNA
<213> ORGANISM: Artificial Sequence
<220> FEATURE:
<223> OTHER INFORMATION: Antisense Compound

<400> SEQUENCE: 176
ccacctgcag caggaccagg                                              20

<210> SEQ ID NO 177
<211> LENGTH: 20
<212> TYPE: DNA
<213> ORGANISM: Artificial Sequence
<220> FEATURE:
<223> OTHER INFORMATION: Antisense Compound

<400> SEQUENCE: 177
tgccacctgc agcaggacca                                              20

<210> SEQ ID NO 178
<211> LENGTH: 20
<212> TYPE: DNA
<213> ORGANISM: Artificial Sequence
<220> FEATURE:
<223> OTHER INFORMATION: Antisense Compound

<400> SEQUENCE: 178
ttgccacctg cagcaggacc                                              20

<210> SEQ ID NO 179
<211> LENGTH: 20
<212> TYPE: DNA
<213> ORGANISM: Artificial Sequence
<220> FEATURE:
<223> OTHER INFORMATION: Antisense Compound

<400> SEQUENCE: 179
cttgccacct gcagcaggac                                              20
```

```
<210> SEQ ID NO 180
<211> LENGTH: 20
<212> TYPE: DNA
<213> ORGANISM: Artificial Sequence
<220> FEATURE:
<223> OTHER INFORMATION: Antisense Compound

<400> SEQUENCE: 180
gcttgccacc tgcagcagga                                          20

<210> SEQ ID NO 181
<211> LENGTH: 20
<212> TYPE: DNA
<213> ORGANISM: Artificial Sequence
<220> FEATURE:
<223> OTHER INFORMATION: Antisense Compound

<400> SEQUENCE: 181
agcttgccac ctgcagcagg                                          20

<210> SEQ ID NO 182
<211> LENGTH: 20
<212> TYPE: DNA
<213> ORGANISM: Artificial Sequence
<220> FEATURE:
<223> OTHER INFORMATION: Antisense Compound

<400> SEQUENCE: 182
gagcttgcca cctgcagcag                                          20

<210> SEQ ID NO 183
<211> LENGTH: 20
<212> TYPE: DNA
<213> ORGANISM: Artificial Sequence
<220> FEATURE:
<223> OTHER INFORMATION: Antisense Compound

<400> SEQUENCE: 183
agagcttgcc acctgcagca                                          20

<210> SEQ ID NO 184
<211> LENGTH: 20
<212> TYPE: DNA
<213> ORGANISM: Artificial Sequence
<220> FEATURE:
<223> OTHER INFORMATION: Antisense Compound

<400> SEQUENCE: 184
cagagcttgc cacctgcagc                                          20

<210> SEQ ID NO 185
<211> LENGTH: 20
<212> TYPE: DNA
<213> ORGANISM: Artificial Sequence
<220> FEATURE:
<223> OTHER INFORMATION: Antisense Compound

<400> SEQUENCE: 185
ccagagcttg ccacctgcag                                          20

<210> SEQ ID NO 186
<211> LENGTH: 20
<212> TYPE: DNA
<213> ORGANISM: Artificial Sequence
<220> FEATURE:
```

<223> OTHER INFORMATION: Antisense Compound

<400> SEQUENCE: 186
cccagagctt gccacctgca                                          20

<210> SEQ ID NO 187
<211> LENGTH: 20
<212> TYPE: DNA
<213> ORGANISM: Artificial Sequence
<220> FEATURE:
<223> OTHER INFORMATION: Antisense Compound

<400> SEQUENCE: 187
tcccagagct tgccacctgc                                          20

<210> SEQ ID NO 188
<211> LENGTH: 20
<212> TYPE: DNA
<213> ORGANISM: Artificial Sequence
<220> FEATURE:
<223> OTHER INFORMATION: Antisense Compound

<400> SEQUENCE: 188
gtagagatgc tcatgtagtc                                          20

<210> SEQ ID NO 189
<211> LENGTH: 20
<212> TYPE: DNA
<213> ORGANISM: Artificial Sequence
<220> FEATURE:
<223> OTHER INFORMATION: Antisense Compound

<400> SEQUENCE: 189
aaaaccagct ggtacaacag                                          20

<210> SEQ ID NO 190
<211> LENGTH: 20
<212> TYPE: DNA
<213> ORGANISM: Artificial Sequence
<220> FEATURE:
<223> OTHER INFORMATION: Antisense Compound

<400> SEQUENCE: 190 gaaaaccag ctggtacaac                                           20

<210> SEQ ID NO 191
<211> LENGTH: 20
<212> TYPE: DNA
<213> ORGANISM: Artificial Sequence
<220> FEATURE:
<223> OTHER INFORMATION: Antisense Compound

<400> SEQUENCE: 191
tccatgagca ggtggcacac                                          20

<210> SEQ ID NO 192
<211> LENGTH: 20
<212> TYPE: DNA
<213> ORGANISM: Artificial Sequence
<220> FEATURE:
<223> OTHER INFORMATION: Antisense Compound

<400> SEQUENCE: 192
atccatgagc aggtggcaca                                          20

```
<210> SEQ ID NO 193
<211> LENGTH: 20
<212> TYPE: DNA
<213> ORGANISM: Artificial Sequence
<220> FEATURE:
<223> OTHER INFORMATION: Antisense Compound

<400> SEQUENCE: 193
catccatgag caggtggcac                                              20

<210> SEQ ID NO 194
<211> LENGTH: 20
<212> TYPE: DNA
<213> ORGANISM: Artificial Sequence
<220> FEATURE:
<223> OTHER INFORMATION: Antisense Compound

<400> SEQUENCE: 194
tcatccatga gcaggtggca                                              20

<210> SEQ ID NO 195
<211> LENGTH: 20
<212> TYPE: DNA
<213> ORGANISM: Artificial Sequence
<220> FEATURE:
<223> OTHER INFORMATION: Antisense Compound

<400> SEQUENCE: 195
cccttccaca gcagctgctg                                              20

<210> SEQ ID NO 196
<211> LENGTH: 20
<212> TYPE: DNA
<213> ORGANISM: Artificial Sequence
<220> FEATURE:
<223> OTHER INFORMATION: Antisense Compound

<400> SEQUENCE: 196
agcccttcca cagcagctgc                                              20

<210> SEQ ID NO 197
<211> LENGTH: 20
<212> TYPE: DNA
<213> ORGANISM: Artificial Sequence
<220> FEATURE:
<223> OTHER INFORMATION: Antisense Compound

<400> SEQUENCE: 197
gagcccttcc acagcagctg                                              20

<210> SEQ ID NO 198
<211> LENGTH: 20
<212> TYPE: DNA
<213> ORGANISM: Artificial Sequence
<220> FEATURE:
<223> OTHER INFORMATION: Antisense Compound

<400> SEQUENCE: 198
aggagccctt ccacagcagc                                              20

<210> SEQ ID NO 199
<211> LENGTH: 20
<212> TYPE: DNA
<213> ORGANISM: Artificial Sequence
<220> FEATURE:
<223> OTHER INFORMATION: Antisense Compound
```

<400> SEQUENCE: 199
aaggagccct tccacagcag                                              20

<210> SEQ ID NO 200
<211> LENGTH: 20
<212> TYPE: DNA
<213> ORGANISM: Artificial Sequence
<220> FEATURE:
<223> OTHER INFORMATION: Antisense Compound

<400> SEQUENCE: 200
gaaggagccc ttccacagca                                              20

<210> SEQ ID NO 201
<211> LENGTH: 20
<212> TYPE: DNA
<213> ORGANISM: Artificial Sequence
<220> FEATURE:
<223> OTHER INFORMATION: Antisense Compound

<400> SEQUENCE: 201
tgaaggagcc cttccacagc                                              20

<210> SEQ ID NO 202
<211> LENGTH: 20
<212> TYPE: DNA
<213> ORGANISM: Artificial Sequence
<220> FEATURE:
<223> OTHER INFORMATION: Antisense Compound

<400> SEQUENCE: 202
ttgaaggagc ccttccacag                                              20

<210> SEQ ID NO 203
<211> LENGTH: 20
<212> TYPE: DNA
<213> ORGANISM: Artificial Sequence
<220> FEATURE:
<223> OTHER INFORMATION: Antisense Compound

<400> SEQUENCE: 203
cttgaaggag cccttccaca                                              20

<210> SEQ ID NO 204
<211> LENGTH: 20
<212> TYPE: DNA
<213> ORGANISM: Artificial Sequence
<220> FEATURE:
<223> OTHER INFORMATION: Antisense Compound

<400> SEQUENCE: 204
ggcttgaagg agcccttcca                                              20

<210> SEQ ID NO 205
<211> LENGTH: 20
<212> TYPE: DNA
<213> ORGANISM: Artificial Sequence
<220> FEATURE:
<223> OTHER INFORMATION: Antisense Compound

<400> SEQUENCE: 205
tgggcttgaa ggagcccttc                                              20

<210> SEQ ID NO 206
<211> LENGTH: 20

```
<212> TYPE: DNA
<213> ORGANISM: Artificial Sequence
<220> FEATURE:
<223> OTHER INFORMATION: Antisense Compound

<400> SEQUENCE: 206
ctgggcttga aggagccctt                                                   20

<210> SEQ ID NO 207
<211> LENGTH: 20
<212> TYPE: DNA
<213> ORGANISM: Artificial Sequence
<220> FEATURE:
<223> OTHER INFORMATION: Antisense Compound

<400> SEQUENCE: 207
gctgggcttg aaggagccct                                                   20

<210> SEQ ID NO 208
<211> LENGTH: 20
<212> TYPE: DNA
<213> ORGANISM: Artificial Sequence
<220> FEATURE:
<223> OTHER INFORMATION: Antisense Compound

<400> SEQUENCE: 208
gccctgggtt tcacatgctc                                                   20

<210> SEQ ID NO 209
<211> LENGTH: 20
<212> TYPE: DNA
<213> ORGANISM: Artificial Sequence
<220> FEATURE:
<223> OTHER INFORMATION: Antisense Compound

<400> SEQUENCE: 209
ggccctgggt ttcacatgct                                                   20

<210> SEQ ID NO 210
<211> LENGTH: 20
<212> TYPE: DNA
<213> ORGANISM: Artificial Sequence
<220> FEATURE:
<223> OTHER INFORMATION: Antisense Compound

<400> SEQUENCE: 210
tatacaggta attgtcaggg                                                   20

<210> SEQ ID NO 211
<211> LENGTH: 20
<212> TYPE: DNA
<213> ORGANISM: Artificial Sequence
<220> FEATURE:
<223> OTHER INFORMATION: Antisense Compound

<400> SEQUENCE: 211
ttatacaggt aattgtcagg                                                   20

<210> SEQ ID NO 212
<211> LENGTH: 20
<212> TYPE: DNA
<213> ORGANISM: Artificial Sequence
<220> FEATURE:
<223> OTHER INFORMATION: Antisense Compound

<400> SEQUENCE: 212
```
attatacagg taattgtcag 20

<210> SEQ ID NO 213
<211> LENGTH: 20
<212> TYPE: DNA
<213> ORGANISM: Artificial Sequence
<220> FEATURE:
<223> OTHER INFORMATION: Antisense Compound

<400> SEQUENCE: 213
gttgactgca taggtgagat 20

<210> SEQ ID NO 214
<211> LENGTH: 20
<212> TYPE: DNA
<213> ORGANISM: Artificial Sequence
<220> FEATURE:
<223> OTHER INFORMATION: Antisense Compound

<400> SEQUENCE: 214
aatgttgact gcataggtga 20

<210> SEQ ID NO 215
<211> LENGTH: 20
<212> TYPE: DNA
<213> ORGANISM: Artificial Sequence
<220> FEATURE:
<223> OTHER INFORMATION: Antisense Compound

<400> SEQUENCE: 215
caaatgttga ctgcataggt 20

<210> SEQ ID NO 216
<211> LENGTH: 20
<212> TYPE: DNA
<213> ORGANISM: Artificial Sequence
<220> FEATURE:
<223> OTHER INFORMATION: Antisense Compound

<400> SEQUENCE: 216
tccaaatgtt gactgcatag 20

<210> SEQ ID NO 217
<211> LENGTH: 20
<212> TYPE: DNA
<213> ORGANISM: Artificial Sequence
<220> FEATURE:
<223> OTHER INFORMATION: Antisense Compound

<400> SEQUENCE: 217
agacttcagg gtgctggctg 20

<210> SEQ ID NO 218
<211> LENGTH: 20
<212> TYPE: DNA
<213> ORGANISM: Artificial Sequence
<220> FEATURE:
<223> OTHER INFORMATION: Antisense Compound

<400> SEQUENCE: 218
cagacttcag ggtgctggct 20

<210> SEQ ID NO 219
<211> LENGTH: 20
<212> TYPE: DNA
<213> ORGANISM: Artificial Sequence

```
<220> FEATURE:
<223> OTHER INFORMATION: Antisense Compound

<400> SEQUENCE: 219
ccagacttca gggtgctggc                                                      20

<210> SEQ ID NO 220
<211> LENGTH: 20
<212> TYPE: DNA
<213> ORGANISM: Artificial Sequence
<220> FEATURE:
<223> OTHER INFORMATION: Antisense Compound

<400> SEQUENCE: 220
tcctggatta ttatagccac                                                      20

<210> SEQ ID NO 221
<211> LENGTH: 20
<212> TYPE: DNA
<213> ORGANISM: Artificial Sequence
<220> FEATURE:
<223> OTHER INFORMATION: Antisense Compound

<400> SEQUENCE: 221
atcctggatt attatagcca                                                      20

<210> SEQ ID NO 222
<211> LENGTH: 20
<212> TYPE: DNA
<213> ORGANISM: Artificial Sequence
<220> FEATURE:
<223> OTHER INFORMATION: Antisense Compound

<400> SEQUENCE: 222
catcctggat tattatagcc                                                      20

<210> SEQ ID NO 223
<211> LENGTH: 20
<212> TYPE: DNA
<213> ORGANISM: Artificial Sequence
<220> FEATURE:
<223> OTHER INFORMATION: Antisense Compound

<400> SEQUENCE: 223
gcatcctgga ttattatagc                                                      20

<210> SEQ ID NO 224
<211> LENGTH: 20
<212> TYPE: DNA
<213> ORGANISM: Artificial Sequence
<220> FEATURE:
<223> OTHER INFORMATION: Antisense Compound

<400> SEQUENCE: 224
gagcatcctg gattattata                                                      20

<210> SEQ ID NO 225
<211> LENGTH: 20
<212> TYPE: DNA
<213> ORGANISM: Artificial Sequence
<220> FEATURE:
<223> OTHER INFORMATION: Antisense Compound

<400> SEQUENCE: 225
tgagcatcct ggattattat                                                      20
```

```
<210> SEQ ID NO 226
<211> LENGTH: 20
<212> TYPE: DNA
<213> ORGANISM: Artificial Sequence
<220> FEATURE:
<223> OTHER INFORMATION: Antisense Compound

<400> SEQUENCE: 226
ctgagcatcc tggattatta                                           20

<210> SEQ ID NO 227
<211> LENGTH: 20
<212> TYPE: DNA
<213> ORGANISM: Artificial Sequence
<220> FEATURE:
<223> OTHER INFORMATION: Antisense Compound

<400> SEQUENCE: 227
cctgagcatc ctggattatt                                           20

<210> SEQ ID NO 228
<211> LENGTH: 20
<212> TYPE: DNA
<213> ORGANISM: Artificial Sequence
<220> FEATURE:
<223> OTHER INFORMATION: Antisense Compound

<400> SEQUENCE: 228
gcacttggct ggttcctggc                                           20

<210> SEQ ID NO 229
<211> LENGTH: 20
<212> TYPE: DNA
<213> ORGANISM: Artificial Sequence
<220> FEATURE:
<223> OTHER INFORMATION: Antisense Compound

<400> SEQUENCE: 229
ggtaagacaa ttcttccagt                                           20

<210> SEQ ID NO 230
<211> LENGTH: 20
<212> TYPE: DNA
<213> ORGANISM: Artificial Sequence
<220> FEATURE:
<223> OTHER INFORMATION: Antisense Compound

<400> SEQUENCE: 230
tggtaagaca attcttccag                                           20

<210> SEQ ID NO 231
<211> LENGTH: 20
<212> TYPE: DNA
<213> ORGANISM: Artificial Sequence
<220> FEATURE:
<223> OTHER INFORMATION: Antisense Compound

<400> SEQUENCE: 231
ttggtaagac aattcttcca                                           20

<210> SEQ ID NO 232
<211> LENGTH: 20
<212> TYPE: DNA
<213> ORGANISM: Artificial Sequence
<220> FEATURE:
<223> OTHER INFORMATION: Antisense Compound
```

<400> SEQUENCE: 232
cttggtaaga caattcttcc                                          20

<210> SEQ ID NO 233
<211> LENGTH: 20
<212> TYPE: DNA
<213> ORGANISM: Artificial Sequence
<220> FEATURE:
<223> OTHER INFORMATION: Antisense Compound

<400> SEQUENCE: 233
agcttggtaa gacaattctt                                          20

<210> SEQ ID NO 234
<211> LENGTH: 20
<212> TYPE: DNA
<213> ORGANISM: Artificial Sequence
<220> FEATURE:
<223> OTHER INFORMATION: Antisense Compound

<400> SEQUENCE: 234
gagcttggta agacaattct                                          20

<210> SEQ ID NO 235
<211> LENGTH: 20
<212> TYPE: DNA
<213> ORGANISM: Artificial Sequence
<220> FEATURE:
<223> OTHER INFORMATION: Antisense Compound

<400> SEQUENCE: 235
aagagcttgg taagacaatt                                          20

<210> SEQ ID NO 236
<211> LENGTH: 20
<212> TYPE: DNA
<213> ORGANISM: Artificial Sequence
<220> FEATURE:
<223> OTHER INFORMATION: Antisense Compound

<400> SEQUENCE: 236
gcaagagctt ggtaagacaa                                          20

<210> SEQ ID NO 237
<211> LENGTH: 20
<212> TYPE: DNA
<213> ORGANISM: Artificial Sequence
<220> FEATURE:
<223> OTHER INFORMATION: Antisense Compound

<400> SEQUENCE: 237
ggcaagagct tggtaagaca                                          20

<210> SEQ ID NO 238
<211> LENGTH: 20
<212> TYPE: DNA
<213> ORGANISM: Artificial Sequence
<220> FEATURE:
<223> OTHER INFORMATION: Antisense Compound

<400> SEQUENCE: 238
agggcaagag cttggtaaga                                          20

<210> SEQ ID NO 239

```
<211> LENGTH: 20
<212> TYPE: DNA
<213> ORGANISM: Artificial Sequence
<220> FEATURE:
<223> OTHER INFORMATION: Antisense Compound

<400> SEQUENCE: 239
acagggcaag agcttggtaa                                               20

<210> SEQ ID NO 240
<211> LENGTH: 20
<212> TYPE: DNA
<213> ORGANISM: Artificial Sequence
<220> FEATURE:
<223> OTHER INFORMATION: Antisense Compound

<400> SEQUENCE: 240
aacagggcaa gagcttggta                                               20

<210> SEQ ID NO 241
<211> LENGTH: 20
<212> TYPE: DNA
<213> ORGANISM: Artificial Sequence
<220> FEATURE:
<223> OTHER INFORMATION: Antisense Compound

<400> SEQUENCE: 241
aaacagggca agagcttggt                                               20

<210> SEQ ID NO 242
<211> LENGTH: 20
<212> TYPE: DNA
<213> ORGANISM: Artificial Sequence
<220> FEATURE:
<223> OTHER INFORMATION: Antisense Compound

<400> SEQUENCE: 242
aaaacagggc aagagcttgg                                               20

<210> SEQ ID NO 243
<211> LENGTH: 20
<212> TYPE: DNA
<213> ORGANISM: Artificial Sequence
<220> FEATURE:
<223> OTHER INFORMATION: Antisense Compound

<400> SEQUENCE: 243
gaaaacaggg caagagcttg                                               20

<210> SEQ ID NO 244
<211> LENGTH: 20
<212> TYPE: DNA
<213> ORGANISM: Artificial Sequence
<220> FEATURE:
<223> OTHER INFORMATION: Antisense Compound

<400> SEQUENCE: 244
cagaaaacag ggcaagagct                                               20

<210> SEQ ID NO 245
<211> LENGTH: 20
<212> TYPE: DNA
<213> ORGANISM: Artificial Sequence
<220> FEATURE:
<223> OTHER INFORMATION: Antisense Compound

<400> SEQUENCE: 245
```
tccagaaaac agggcaagag                                              20

<210> SEQ ID NO 246
<211> LENGTH: 20
<212> TYPE: DNA
<213> ORGANISM: Artificial Sequence
<220> FEATURE:
<223> OTHER INFORMATION: Antisense Compound

<400> SEQUENCE: 246
gggcaccatg ctgattttcc                                              20

<210> SEQ ID NO 247
<211> LENGTH: 20
<212> TYPE: DNA
<213> ORGANISM: Artificial Sequence
<220> FEATURE:
<223> OTHER INFORMATION: Antisense Compound

<400> SEQUENCE: 247
gctctctggc cagaggactg                                              20

<210> SEQ ID NO 248
<211> LENGTH: 20
<212> TYPE: DNA
<213> ORGANISM: Artificial Sequence
<220> FEATURE:
<223> OTHER INFORMATION: Antisense Compound

<400> SEQUENCE: 248
atgctctctg gccagaggac                                              20

<210> SEQ ID NO 249
<211> LENGTH: 20
<212> TYPE: DNA
<213> ORGANISM: Artificial Sequence
<220> FEATURE:
<223> OTHER INFORMATION: Antisense Compound

<400> SEQUENCE: 249
gatgctctct ggccagagga                                              20

<210> SEQ ID NO 250
<211> LENGTH: 20
<212> TYPE: DNA
<213> ORGANISM: Artificial Sequence
<220> FEATURE:
<223> OTHER INFORMATION: Antisense Compound

<400> SEQUENCE: 250
gctgatgctc tctggccaga                                              20

<210> SEQ ID NO 251
<211> LENGTH: 20
<212> TYPE: DNA
<213> ORGANISM: Artificial Sequence
<220> FEATURE:
<223> OTHER INFORMATION: Antisense Compound

<400> SEQUENCE: 251
gtccaggaac aggctctctg                                              20

<210> SEQ ID NO 252
<211> LENGTH: 20
<212> TYPE: DNA

```
<213> ORGANISM: Artificial Sequence
<220> FEATURE:
<223> OTHER INFORMATION: Antisense Compound

<400> SEQUENCE: 252
aggtccagga acaggctctc                                                    20

<210> SEQ ID NO 253
<211> LENGTH: 20
<212> TYPE: DNA
<213> ORGANISM: Artificial Sequence
<220> FEATURE:
<223> OTHER INFORMATION: Antisense Compound

<400> SEQUENCE: 253
caggtccagg aacaggctct                                                    20

<210> SEQ ID NO 254
<211> LENGTH: 20
<212> TYPE: DNA
<213> ORGANISM: Artificial Sequence
<220> FEATURE:
<223> OTHER INFORMATION: Antisense Compound

<400> SEQUENCE: 254
gcaggtccag gaacaggctc                                                    20

<210> SEQ ID NO 255
<211> LENGTH: 20
<212> TYPE: DNA
<213> ORGANISM: Artificial Sequence
<220> FEATURE:
<223> OTHER INFORMATION: Antisense Compound

<400> SEQUENCE: 255
agcaggtcca ggaacaggct                                                    20

<210> SEQ ID NO 256
<211> LENGTH: 20
<212> TYPE: DNA
<213> ORGANISM: Artificial Sequence
<220> FEATURE:
<223> OTHER INFORMATION: Antisense Compound

<400> SEQUENCE: 256
gagcaggtcc aggaacaggc                                                    20

<210> SEQ ID NO 257
<211> LENGTH: 20
<212> TYPE: DNA
<213> ORGANISM: Artificial Sequence
<220> FEATURE:
<223> OTHER INFORMATION: Antisense Compound

<400> SEQUENCE: 257
acttgggaac tcatcccagg                                                    20

<210> SEQ ID NO 258
<211> LENGTH: 20
<212> TYPE: DNA
<213> ORGANISM: Artificial Sequence
<220> FEATURE:
<223> OTHER INFORMATION: Antisense Compound

<400> SEQUENCE: 258
cacttgggaa ctcatcccag                                                    20
```

<210> SEQ ID NO 259
<211> LENGTH: 20
<212> TYPE: DNA
<213> ORGANISM: Artificial Sequence
<220> FEATURE:
<223> OTHER INFORMATION: Antisense Compound

<400> SEQUENCE: 259
gcacttggga actcatccca                                               20

<210> SEQ ID NO 260
<211> LENGTH: 20
<212> TYPE: DNA
<213> ORGANISM: Artificial Sequence
<220> FEATURE:
<223> OTHER INFORMATION: Antisense Compound

<400> SEQUENCE: 260
ctcagggagt tgctgaagct                                               20

<210> SEQ ID NO 261
<211> LENGTH: 20
<212> TYPE: DNA
<213> ORGANISM: Artificial Sequence
<220> FEATURE:
<223> OTHER INFORMATION: Antisense Compound

<400> SEQUENCE: 261
gctcagggag ttgctgaagc                                               20

<210> SEQ ID NO 262
<211> LENGTH: 20
<212> TYPE: DNA
<213> ORGANISM: Artificial Sequence
<220> FEATURE:
<223> OTHER INFORMATION: Antisense Compound

<400> SEQUENCE: 262
tggctcaggg agttgctgaa                                               20

<210> SEQ ID NO 263
<211> LENGTH: 20
<212> TYPE: DNA
<213> ORGANISM: Artificial Sequence
<220> FEATURE:
<223> OTHER INFORMATION: Antisense Compound

<400> SEQUENCE: 263
ctggctcagg gagttgctga                                               20

<210> SEQ ID NO 264
<211> LENGTH: 20
<212> TYPE: DNA
<213> ORGANISM: Artificial Sequence
<220> FEATURE:
<223> OTHER INFORMATION: Antisense Compound

<400> SEQUENCE: 264
gactggctca gggagttgct                                               20

<210> SEQ ID NO 265
<211> LENGTH: 20
<212> TYPE: DNA
<213> ORGANISM: Artificial Sequence
<220> FEATURE:

<223> OTHER INFORMATION: Antisense Compound

<400> SEQUENCE: 265
ggacccagct ctctgggaca　　　　　　　　　　　　　　　　　　　　　　　20

<210> SEQ ID NO 266
<211> LENGTH: 20
<212> TYPE: DNA
<213> ORGANISM: Artificial Sequence
<220> FEATURE:
<223> OTHER INFORMATION: Antisense Compound

<400> SEQUENCE: 266
tggacccagc tctctgggac　　　　　　　　　　　　　　　　　　　　　　　20

<210> SEQ ID NO 267
<211> LENGTH: 20
<212> TYPE: DNA
<213> ORGANISM: Artificial Sequence
<220> FEATURE:
<223> OTHER INFORMATION: Antisense Compound

<400> SEQUENCE: 267
tctggaccca gctctctggg　　　　　　　　　　　　　　　　　　　　　　　20

<210> SEQ ID NO 268
<211> LENGTH: 20
<212> TYPE: DNA
<213> ORGANISM: Artificial Sequence
<220> FEATURE:
<223> OTHER INFORMATION: Antisense Compound

<400> SEQUENCE: 268
ggtctggacc cagctctctg　　　　　　　　　　　　　　　　　　　　　　　20

<210> SEQ ID NO 269
<211> LENGTH: 20
<212> TYPE: DNA
<213> ORGANISM: Artificial Sequence
<220> FEATURE:
<223> OTHER INFORMATION: Antisense Compound

<400> SEQUENCE: 269
gggtctggac ccagctctct　　　　　　　　　　　　　　　　　　　　　　　20

<210> SEQ ID NO 270
<211> LENGTH: 20
<212> TYPE: DNA
<213> ORGANISM: Artificial Sequence
<220> FEATURE:
<223> OTHER INFORMATION: Antisense Compound

<400> SEQUENCE: 270
tggttggctc agagagctgg　　　　　　　　　　　　　　　　　　　　　　　20

<210> SEQ ID NO 271
<211> LENGTH: 20
<212> TYPE: DNA
<213> ORGANISM: Artificial Sequence
<220> FEATURE:
<223> OTHER INFORMATION: Antisense Compound

<400> SEQUENCE: 271
agtggttggc tcagagagct　　　　　　　　　　　　　　　　　　　　　　　20

```
<210> SEQ ID NO 272
<211> LENGTH: 20
<212> TYPE: DNA
<213> ORGANISM: Artificial Sequence
<220> FEATURE:
<223> OTHER INFORMATION: Antisense Compound

<400> SEQUENCE: 272
cagtggttgg ctcagagagc                                              20

<210> SEQ ID NO 273
<211> LENGTH: 20
<212> TYPE: DNA
<213> ORGANISM: Artificial Sequence
<220> FEATURE:
<223> OTHER INFORMATION: Antisense Compound

<400> SEQUENCE: 273
acagtggttg gctcagagag                                              20

<210> SEQ ID NO 274
<211> LENGTH: 20
<212> TYPE: DNA
<213> ORGANISM: Artificial Sequence
<220> FEATURE:
<223> OTHER INFORMATION: Antisense Compound

<400> SEQUENCE: 274
cacagtggtt ggctcagaga                                              20

<210> SEQ ID NO 275
<211> LENGTH: 20
<212> TYPE: DNA
<213> ORGANISM: Artificial Sequence
<220> FEATURE:
<223> OTHER INFORMATION: Antisense Compound

<400> SEQUENCE: 275
gcactgctgg caagcaggct                                              20

<210> SEQ ID NO 276
<211> LENGTH: 20
<212> TYPE: DNA
<213> ORGANISM: Artificial Sequence
<220> FEATURE:
<223> OTHER INFORMATION: Antisense Compound

<400> SEQUENCE: 276
aaggcttata cccctcttcc                                              20

<210> SEQ ID NO 277
<211> LENGTH: 20
<212> TYPE: DNA
<213> ORGANISM: Artificial Sequence
<220> FEATURE:
<223> OTHER INFORMATION: Antisense Compound

<400> SEQUENCE: 277
aaaggcttat acccctcttc                                              20

<210> SEQ ID NO 278
<220> FEATURE:

<400> SEQUENCE: 278

000
```

```
<210> SEQ ID NO 279
<211> LENGTH: 20
<212> TYPE: DNA
<213> ORGANISM: Artificial Sequence
<220> FEATURE:
<223> OTHER INFORMATION: Antisense Compound

<400> SEQUENCE: 279
ggaaaggctt ataccctct                                                   20

<210> SEQ ID NO 280
<211> LENGTH: 20
<212> TYPE: DNA
<213> ORGANISM: Artificial Sequence
<220> FEATURE:
<223> OTHER INFORMATION: Antisense Compound

<400> SEQUENCE: 280
tggaaaggct tataccctc                                                   20

<210> SEQ ID NO 281
<211> LENGTH: 20
<212> TYPE: DNA
<213> ORGANISM: Artificial Sequence
<220> FEATURE:
<223> OTHER INFORMATION: Antisense Compound

<400> SEQUENCE: 281
cttggaaagg cttataccc                                                   20

<210> SEQ ID NO 282
<211> LENGTH: 20
<212> TYPE: DNA
<213> ORGANISM: Artificial Sequence
<220> FEATURE:
<223> OTHER INFORMATION: Antisense Compound

<400> SEQUENCE: 282
gtcttggaaa ggcttatacc                                                  20

<210> SEQ ID NO 283
<211> LENGTH: 20
<212> TYPE: DNA
<213> ORGANISM: Artificial Sequence
<220> FEATURE:
<223> OTHER INFORMATION: Antisense Compound

<400> SEQUENCE: 283
ggtcttggaa aggcttatac                                                  20

<210> SEQ ID NO 284
<211> LENGTH: 20
<212> TYPE: DNA
<213> ORGANISM: Artificial Sequence
<220> FEATURE:
<223> OTHER INFORMATION: Antisense Compound

<400> SEQUENCE: 284
aggtcttgga aaggcttata                                                  20

<210> SEQ ID NO 285
<220> FEATURE:

<400> SEQUENCE: 285

000
```

```
<210> SEQ ID NO 286
<211> LENGTH: 20
<212> TYPE: DNA
<213> ORGANISM: Artificial Sequence
<220> FEATURE:
<223> OTHER INFORMATION: Antisense Compound

<400> SEQUENCE: 286
tgaggtcttg gaaaggctta                                              20

<210> SEQ ID NO 287
<211> LENGTH: 20
<212> TYPE: DNA
<213> ORGANISM: Artificial Sequence
<220> FEATURE:
<223> OTHER INFORMATION: Antisense Compound

<400> SEQUENCE: 287
agtccaaagg tgaacaaggg                                              20

<210> SEQ ID NO 288
<211> LENGTH: 20
<212> TYPE: DNA
<213> ORGANISM: Artificial Sequence
<220> FEATURE:
<223> OTHER INFORMATION: Antisense Compound

<400> SEQUENCE: 288
ccagtccaaa ggtgaacaag                                              20

<210> SEQ ID NO 289
<211> LENGTH: 20
<212> TYPE: DNA
<213> ORGANISM: Artificial Sequence
<220> FEATURE:
<223> OTHER INFORMATION: Antisense Compound

<400> SEQUENCE: 289
gtccagtcca aaggtgaaca                                              20

<210> SEQ ID NO 290
<211> LENGTH: 20
<212> TYPE: DNA
<213> ORGANISM: Artificial Sequence
<220> FEATURE:
<223> OTHER INFORMATION: Antisense Compound

<400> SEQUENCE: 290
tgtccagtcc aaaggtgaac                                              20

<210> SEQ ID NO 291
<211> LENGTH: 20
<212> TYPE: DNA
<213> ORGANISM: Artificial Sequence
<220> FEATURE:
<223> OTHER INFORMATION: Antisense Compound

<400> SEQUENCE: 291
tccacagcag cagccacagc                                              20

<210> SEQ ID NO 292
<211> LENGTH: 20
<212> TYPE: DNA
<213> ORGANISM: Artificial Sequence
<220> FEATURE:
```

<223> OTHER INFORMATION: Antisense Compound

<400> SEQUENCE: 292
tactcttctc tgagatgccc                                            20

<210> SEQ ID NO 293
<211> LENGTH: 20
<212> TYPE: DNA
<213> ORGANISM: Artificial Sequence
<220> FEATURE:
<223> OTHER INFORMATION: Antisense Compound

<400> SEQUENCE: 293
tttactcttc tctgagatgc                                            20

<210> SEQ ID NO 294
<211> LENGTH: 20
<212> TYPE: DNA
<213> ORGANISM: Artificial Sequence
<220> FEATURE:
<223> OTHER INFORMATION: Antisense Compound

<400> SEQUENCE: 294
gatttactct tctctgagat                                            20

<210> SEQ ID NO 295
<211> LENGTH: 20
<212> TYPE: DNA
<213> ORGANISM: Artificial Sequence
<220> FEATURE:
<223> OTHER INFORMATION: Antisense Compound

<400> SEQUENCE: 295
ggatttactc ttctctgaga                                            20

<210> SEQ ID NO 296
<211> LENGTH: 20
<212> TYPE: DNA
<213> ORGANISM: Artificial Sequence
<220> FEATURE:
<223> OTHER INFORMATION: Antisense Compound

<400> SEQUENCE: 296
aggatttact cttctctgag                                            20

<210> SEQ ID NO 297
<211> LENGTH: 20
<212> TYPE: DNA
<213> ORGANISM: Artificial Sequence
<220> FEATURE:
<223> OTHER INFORMATION: Antisense Compound

<400> SEQUENCE: 297
gaggatttac tcttctctga                                            20

<210> SEQ ID NO 298
<211> LENGTH: 20
<212> TYPE: DNA
<213> ORGANISM: Artificial Sequence
<220> FEATURE:
<223> OTHER INFORMATION: Antisense Compound

<400> SEQUENCE: 298
tgaggattta ctcttctctg                                            20

```
<210> SEQ ID NO 299
<211> LENGTH: 20
<212> TYPE: DNA
<213> ORGANISM: Artificial Sequence
<220> FEATURE:
<223> OTHER INFORMATION: Antisense Compound

<400> SEQUENCE: 299
tctggcttga gctctgagca                                               20

<210> SEQ ID NO 300
<211> LENGTH: 20
<212> TYPE: DNA
<213> ORGANISM: Artificial Sequence
<220> FEATURE:
<223> OTHER INFORMATION: Antisense Compound

<400> SEQUENCE: 300
gtctggcttg agctctgagc                                               20

<210> SEQ ID NO 301
<211> LENGTH: 20
<212> TYPE: DNA
<213> ORGANISM: Artificial Sequence
<220> FEATURE:
<223> OTHER INFORMATION: Antisense Compound

<400> SEQUENCE: 301
aagtcttttg gaaatctgcc                                               20

<210> SEQ ID NO 302
<211> LENGTH: 20
<212> TYPE: DNA
<213> ORGANISM: Artificial Sequence
<220> FEATURE:
<223> OTHER INFORMATION: Antisense Compound

<400> SEQUENCE: 302
ccttcatacc atggttcttc                                               20

<210> SEQ ID NO 303
<211> LENGTH: 20
<212> TYPE: DNA
<213> ORGANISM: Artificial Sequence
<220> FEATURE:
<223> OTHER INFORMATION: Antisense Compound

<400> SEQUENCE: 303
gagcacctct aggcaatgac                                               20

<210> SEQ ID NO 304
<211> LENGTH: 20
<212> TYPE: DNA
<213> ORGANISM: Artificial Sequence
<220> FEATURE:
<223> OTHER INFORMATION: Antisense Compound

<400> SEQUENCE: 304
ccgctgatca cagctgacat                                               20

<210> SEQ ID NO 305
<211> LENGTH: 20
<212> TYPE: DNA
<213> ORGANISM: Artificial Sequence
<220> FEATURE:
<223> OTHER INFORMATION: Antisense Compound
```

```
-continued

<400> SEQUENCE: 305
ccgctcatca ctgctgacat                                                   20

<210> SEQ ID NO 306
<211> LENGTH: 20
<212> TYPE: DNA
<213> ORGANISM: Artificial Sequence
<220> FEATURE:
<223> OTHER INFORMATION: Antisense Compound

<400> SEQUENCE: 306
ccactcatca ctgctgactt                                                   20
```

COMPOSITIONS AND THEIR USES DIRECTED TO IL-4R ALPHA

CROSS-REFERENCE TO RELATED APPLICATIONS

This application is a continuation of International Application No. PCT/US2006/006645, filed Feb. 24, 2006 which claims priority to U.S. Provisional Patent Application Ser. Nos. 60/656,760, filed Feb. 25, 2005; 60/688,897, filed Jun. 9, 2005; 60/700,656, filed Jul. 19, 2005; and 60/709,404 filed Aug. 18, 2005; all of which are incorporated herein by reference in their entirety.

INCORPORATION OF SEQUENCE LISTING

A copy of the sequence listing in both a paper and a computer-readable form is provided herewith and hereby incorporated by reference. The computer readable form is provided on 3.5" diskette containing the file named RTS0792WOSEQ.txt

BACKGROUND OF THE INVENTION

Allergic rhinitis and asthma are widespread conditions with complex and multifactorial etiologies. The severity of the conditions vary widely between individuals, and within individuals, dependent on factors such as genetics, environmental conditions, and cumulative respiratory pathology associated with duration and severity of disease. Both diseases are a result of immune system hyperresponsiveness to innocuous environmental antigens, with asthma typically including an atopic (i.e., allergic) component.

In asthma, the pathology manifests as inflammation, mucus overproduction, and reversible airway obstruction which may result in scarring and remodeling of the airways. Mild asthma is relatively well controlled with current therapeutic interventions including beta-agonists and low dose inhaled corticosteroids or cromolyn. However, moderate and severe asthma are less well controlled, and require daily treatment with more than one long-term control medication to achieve consistent control of asthma symptoms and normal lung function. With moderate asthma, doses of inhaled corticosteroids are increased relative to those given to mild asthmatics, and/or supplemented with long acting beta-agonists (LABA) (e.g., salmeterol) or leukotriene inhibitors (e.g., montelukast, zafirlukast). Although LABA can decrease dependence on corticosteroids, they are not as effective for total asthma control as corticosteroids (e.g., reduction of episodes, emergency room visits) (Lazarus et al., JAMA. 2001.285. 2583-2593; Lemanske et al., JAMA. 2001. 285: 2594-2603). With severe asthma, doses of inhaled corticosteroids are increased, and supplemented with both LABA and oral corticosteroids. Severe asthmatics often suffer from chronic symptoms, including night time symptoms; limitations on activities; and the need for emergency room visits. Additionally, chronic corticosteroid therapy at any level has a number of unwanted side effects, especially in children (e.g., damage to bones resulting in decreased growth).

Allergic rhinitis is inflammation of the nasal passages, and is typically associated with watery nasal discharge, sneezing, congestion and itching of the nose and eyes. It is frequently caused by exposure to irritants, particularly allergens. Allergic rhinitis affects about 20% of the American population and ranks as one of the most common illnesses in the US. Most suffer from seasonal symptoms due to exposure to allergens, such as pollen, that are produced during the natural plant growth season(s). A smaller proportion of sufferers have chronic allergies due to allergens that are produced throughout the year such as house dust mites or animal dander. A number of over the counter treatments are available for the treatment of allergic rhinitis including oral and nasal antihistamines, and decongestants. Antihistamines are utilized to block itching and sneezing and many of these drugs are associated with side effects such as sedation and performance impairment at high doses. Decongestants frequently cause insomnia, tremor, tachycardia, and hypertension. Nasal formulations, when taken improperly or terminated rapidly, can cause rebound congestion. Anticholinergics and montelukast have substantially fewer side effects, but they also have limited efficacy. Similarly, prescription medications are not free of side effects. Nasal corticosteroids can be used for prophylaxis or suppression of symptoms; however, compliance is variable due to side effects including poor taste and nasal irritation and bleeding. Allergen immunotherapy is expensive and time consuming and carries a low risk of anaphylaxis.

Persistent nasal inflammation can result in the development of nasal polyps. Nasal polyps are present in about 4.2% of patients with chronic rhinitis and asthma (4.4% of men and 3.8% of women) (Grigores et al., Allergy Asthma Proc. 2002, 23:169-174). The presence of polyps is increased with age in both sexes and in patients with cystic fibrosis and aspirin-hypersensitivity triad. Nasal polyposis results from chronic inflammation of the nasal and sinus mucous membranes. Chronic inflammation causes a reactive hyperplasia of the intranasal mucosal membrane, which results in the formation of polyps. The precise mechanism of polyp formation is incompletely understood. Nasal polyps are associated with nasal airway obstruction, postnasal drainage, dull headaches, snoring, anosmia, and rhinorrhea. Medical therapies include treatment for underlying chronic allergic rhinitis using antihistamines and topical nasal steroid sprays. For severe nasal polyposis causing severe nasal obstruction, treatment with short-term steroids may be beneficial. Topical use of cromolyn spray has also been found to be helpful to some patients in reducing the severity and size of the nasal polyps. Oral corticosteroids are the most effective medication for the short-term treatment of nasal polyps, and oral corticosteroids have the best effectiveness in shrinking inflammatory polyps. Intranasal steroid sprays may reduce or retard the growth of small nasal polyps, but they are relatively ineffective in massive nasal polyposis. Although nasal polyps can be treated pharmacologically, many of the therapeutics have undesirable side effects. Moreover, polyps tend to be recurrent, eventually requiring surgical intervention. Compositions and methods to inhibit post-surgical recurrence of nasal polyps are not presently available.

Other diseases characterized by similar inflammatory pathways include, but are not limited to, chronic bronchitis, pulmonary fibrosis, emphysema, chronic obstructive pulmonary disease (COPD), and pediatric asthma.

Interleukin Receptor 4-alpha and Inflammatory Signaling Pathways

It is generally acknowledged that allergy and asthma are a result of the dysregulation of the Th2 cytokine response. The presence of CD4+ T cells producing interleukin 4 (IL 4), IL 5 and IL 13 cytokines in bronchoalveolar lavage fluid and in airway epithelial biopsies of asthmatics has been clearly documented. Neutralization of IL 5 results in a decrease in eosinophilia in man, in the absence of a reduction in airway hyperresponsiveness (AHR). IL 4 and IL 13 have been implicated in multiple pathological processes that underlie asthma and allergy, including Th2 lymphocyte differentiation, induction of immunoglobulin E (IgE) production via regulation of the Ig isotype switch to the epsilon heavy chain in B lymphocytes, upregulation of IgE receptors and vascular associated adhesion molecule-1 (VCAM-1) expression, promotion of eosinophil transmigration in the lung, and mucus hypersecretion. IL 13 mediates the development of airway hyperresponsiveness (AHR) to cholinergic stimuli, lung remodeling, and promotion of the secretory phenotype of the inflamed airway epithelium. These observations make components of the Th2 cytokine pathway, particularly IL 4 and IL 13, potential targets for therapeutic intervention for asthma, allergy, and other forms of airway inflammation and/or hyperresponsiveness.

The IL 4 and IL 13 receptors share a common signaling chain, IL 4 receptor alpha (IL 4R-α). IL 4R-α pairs with the common gamma chain on cells of hematopoietic origin to form a type I IL 4R. This receptor binds exclusively IL 4. IL 4 and IL 13 also signal through a second receptor. The receptor is composed of IL 4R-α and IL 13R-α1 (type II IL 4R). IL 13R-α1 is present on both hematopoietic and non-hematopoietic cells. Formation of the IL 4R-α and IL 13R-α1 heterodimer results in a shift in affinity of IL 13R-α1 from a low affinity receptor, to a high affinity receptor. The IL 13R-α2 is a monomeric, high affinity IL 13 receptor that is thought to act as a decoy receptor to negatively regulate IL 13 activity. Signaling through the type I and type II IL 4Rs activates the Jak-Stat pathway; insulin-interleukin4 receptor (14R) motif associated factors such as insulin receptor substrate family of proteins; SH2 containing tyrosine phosphatases; and members of the Stat family such as Stat 6. A number of genetic studies have demonstrated that both IL 4R-α and Stat 6 are essential for allergen-induced pulmonary inflammation and AHR in mice.

IL 4R-α, was cloned independently by two groups (Galizzi et al., Int. Immunol., 1990, 2, 669-675; and Idzerda et al., J. Exp. Med., 1990, 171, 861-873). The human IL4 receptor gene was localized to 16p 11.2-16p 12.1 by in situ hybridization, and the mouse homolog was localized to the distal region of chromosome 7. The position on human chromosome 16 suggests that the IL4 receptor may be a candidate for rearrangements. For example, 12; 16 translocations are often associated with myxoid liposarcomas (Pritchard et al., Genomics, 1991, 10, 801-806).

Inhibitors of IL 4 and IL 13 independently have produced anti-inflammatory effects in mouse pulmonary inflammation models or in clinical trials (Wills-Karp M et al. Science 282: 2258-2261, 1998; Grunig G et al. Science 282: 2261-2263, 1998; Borish L C et al., Am J Respir Crit Care Med 160: 1816-1823, 1999; Kumar R K et al., Am J Respir Crit Care Med 170: 1043-1048, 2004; Yang G et al., Cytokine 28: 224-232, 2004) and are currently being pursued as novel therapeutics for allergy and asthma.

Antisense Oligonucleotides and Pulmonary Disease

Antisense oligonucleotides (ASOs) are being pursued as therapeutics for pulmonary inflammation, airway hyperresponsiveness, and/or asthma. Lung provides an ideal tissue for aerosolized ASOs for several reasons (Nyce and Metzger, Nature, 1997: 385:721-725, incorporated herein by reference); the lung can be targeted non-invasively and specifically, it has a large absorption surface; and is lined with surfactant that may facilitate distribution and uptake of ASOs. Delivery of ASOs to the lung by aerosol results in excellent distribution throughout the lung in both mice and primates. Immunohistochemical staining of inhaled ASOs in normalized and inflamed mouse lung tissue shows heavy staining in alveolar macrophages, eosinophils, and epithelium, moderate staining in blood vessels endothelium, and weak staining in bronchiolar epithelium. ASO-mediated target reduction is observed in dendritic cells, macrophages, eosinophils, and epithelial cells after aerosol administration. The estimated half life of a 2'-methoxyethoxy (2'-MOE) modified oligonucleotide delivered by aerosol administration to mouse or monkey is about 4 to 7, or at least 7 days, respectively. Moreover, ASOs have relatively predictable toxicities and pharmacokinetics based on backbone and nucleotide chemistry. Pulmonary administration of ASOs results in minimal systemic exposure, potentially increasing the safety of such compounds as compared to other classes of drugs.

Compositions and methods for formulation of ASOs and devices for delivery to the lung and nose are well known. ASOs are soluble in aqueous solution and may be delivered using standard nebulizer devices (Nyce, Exp. Opin. Invest. Drugs, 1997, 6:1149-1156). Formulations and methods for modulating the size of droplets using nebulizer devices to target specific portions of the respiratory tract and lungs are well known to those skilled in the art. Oligonucleotides can be delivered using other devices such as dry powder inhalers or metered dose inhalers which can provide improved patient convenience as compared to nebulizer devices, resulting in greater patient compliance.

Generally, the principle behind antisense technology is that an antisense compound hybridizes to a target nucleic acid and effects the modulation of gene expression activity, or function, such as transcription or translation. The modulation of gene expression can be achieved by, for example, target RNA degradation or occupancy-based inhibition. An example of modulation of target RNA function by degradation is RNase H-based degradation of the target RNA upon hybridization with a DNA-like antisense compound. Another example of modulation of gene expression by target degradation is RNA interference (RNAi) using small interfering RNAs (siRNAs). RNAi is a form of antisense-mediated gene silencing involving the introduction of double stranded (ds)RNA-like oligonucleotides leading to the sequence-specific reduction of targeted endogenous mRNA levels. This sequence-specificity makes antisense compounds extremely attractive as tools for target validation and gene functionalization, as well as therapeutics to selectively modulate the expression of genes involved in diseases.

Antisense oligonucleotides targeted to a number of targets including, but not limited to p38 alpha MAP kinase (US Patent Publication No. 20040171566, incorporated by reference); the CD28 receptor ligands B7-1 and B7-2 (US Patent Publication 20040235164, incorporated by reference); intracellular adhesion molecule (ICAM) (WO 2004/108945, incorporated by reference); and adenosine $A_1$ receptor (Nyce and Metzger, Nature, 1997, 385.721-725) have been tested for their ability to inhibit pulmonary inflammation and airway hyperresponsiveness in mouse, rabbit, and/or monkey models of asthma when delivered by inhalation. Various endpoints were analyzed in each case and a portion of the results are presented herein. ASOs targeted to p38 alpha MAP kinase reduced eosinophil recruitment, airway hyperresponsiveness (AHR), and mucus production in two different mouse models. ASOs targeted to each B7.1 and B7.2 decreased target expression and eosinophil recruitment. An ASO targeted to B7.2 also reduced AHR. ASOs targeted to ICAM-1 decreased AHR and decreased neutrophil and eosinophil recruitment in mice. Treatment of Cynomolgus monkeys with an ASO targeted to ICAM-1 significantly reduced airway impedance (resistance) induced by methacholine challenge in naturally Ascaris allergen-sensitized monkeys. An ASO targeted to adenosine $A_1$ receptor reduced receptor density on airway smooth muscle and reduced AHR in an allergic rabbit model.

These data demonstrate that oligonucleotides are effectively delivered by inhalation to cells within the lungs of multiple species, including a non-human primate, and are effective at reducing airway hyperresponsiveness and/or pulmonary inflammation.

However, treatment with any ASO targeted to any inflammatory mediator involved in pulmonary inflammation is not always effective at reducing AHR and/or pulmonary inflammation. ASOs targeted to Jun N-terminal Kinase (JNK-1) found to decrease target expression in vitro were tested in a mouse model of asthma. Treatment with each of two different antisense oligonucleotides targeted to JNK-1 were not effective at reducing methacholine induced AHR, eosinophil recruitment, or mucus production at any of the ASO doses tested.

A number of ASOs and siRNAs designed to target IL 4R-α have been reported for use as research or diagnostic tools, or as pharmaceuticals for the treatment of respiratory disease. US Patent Application U.S.20030104410 teaches an array of nucleic acid probes useful as research tools to identify or detect gene sequences. Allelic variations in the IL 4R-α gene have been identified that increase receptor signaling (Hershey et al., *NEJM*, 1997, 337:1720-1725; Rosa-Rosa et al., *J. Allergy Clin. Immunol.* 1999, 104:1008-1014; Kruse et al., *Immunol.*, 1999, 96, 365-371). PCT patent application WO 2000034789 teaches oligonucleotides for use in diagnostic testing to detect these allelic variations. Patent applications WO 2002085309, WO 2004011613 and U.S. 20040049022 teach ASOs targeted to a series of genes potentially relevant to respiratory disease, including IL 4R-α, for use in pharmaceutical compositions. Patent application U.S. 20050143333 teaches a series of siRNAs targeted to interleukins and interleukin receptors, including IL 4R-α. PCT application WO 2004045543 teaches algorithms and rational design and selection of functional siRNAs including those targeted to IL 4R-α. Although it is suggested in these publications that the ASOs and siRNAs can be used in pharmaceutical compositions, there are no data demonstrating the efficacy of the compounds in vivo for the prevention, amelioration, and/or treatment of any disease or disorder.

SUMMARY OF THE INVENTION

The invention provides compounds, particularly oligomeric compounds, especially nucleic acid and nucleic acid-like oligomers, which are targeted to a nucleic acid encoding IL-4R alpha. Preferably, the oligomeric compounds are antisense oligonucleotides targeted to IL 4R-α, particularly human IL 4R-α (GenBank Accession No. X52425.1, entered 26 May 1992 (SEQ ID NO. 1); GenBank Accession No. BM738518.1, entered 1 Mar. 2002; nucleotides 18636000 to 18689000 of GenBank Accession No. NT_010393.14 entered 19 Feb. 2004, each of which is incorporated by reference), that modulate the expression of IL 4R-α. The compounds comprise at least a 12 nucleobase portion, preferably at least a 17 nucleobase portion of the sequences listed in Table 3, 4 or 5, or are at least 90% identical to validated target segments, or the sequences listed in Table 3, 4, or 5.

The invention provides a method for modulating the expression of IL 4R-α in cells or tissues comprising contacting the cells with at least one compound of the instant invention, and analyzing the cells for indicators of a decrease in expression of IL 4R-α mRNA and/or protein by direct measurement of mRNA and/or protein levels, and/or indicators of pulmonary inflammation and/or airway hyperresponsiveness.

The invention further provides a method for the prevention, amelioration, and/or treatment of pulmonary inflammation and/or airway hyperresponsiveness comprising administering at least one compound of the instant invention to an individual in need of such intervention. The compound is preferably administered by aerosol (i.e., topically) to at least a portion of the respiratory tract. The portion of the respiratory tract selected is dependent upon the location of the inflammation. For example, in the case of asthma, the compound is preferably delivered predominantly to the lung. In the case of allergic rhinitis, the compound is preferably delivered predominantly to the nasal cavity and/or sinus. The compound is delivered using any of a number of standard delivery devices and methods well known to those skilled in the art, including, but not limited to nebulizers, nasal and pulmonary inhalers, dry powder inhalers, and metered dose inhalers.

The invention also provides a method of use of the compositions of the instant invention for the preparation of a medicament for the prevention, amelioration, and/or treatment disease, especially a disease associated with and including at least one indicator of pulmonary inflammation and/or airway hyperresponsiveness. The medicament is preferably formulated for aerosol administration to at least a portion of the respiratory tract.

DETAILED DESCRIPTION OF THE INVENTION

Asthma, allergy, and a number of other diseases or conditions related to pulmonary inflammation and/or AHR share common inflammatory mediators, including IL 4R-α, the common subunit of IL 4R and IL 13R. Therapeutic interventions for these diseases or conditions are not completely satisfactory due to lack of efficacy and/or unwanted side effects of the compounds. The instant invention provides oligomeric compounds, preferably ASOs, for the prevention, amelioration, and/or treatment of pulmonary inflammation and/or airway hyperresponsiveness. As used herein, the term "prevention" means to delay or forestall onset or development of a condition or disease for a period of time from hours to days, preferably weeks to months. As used herein, the term "amelioration" means a lessening of at least one indicator of the severity of a condition or disease. The severity of indicators may be determined by subjective or objective measures. As used herein, "treatment" means to administer a composition of the invention to effect an alteration or improvement of the disease or condition. Prevention, amelioration, and/or treatment may require administration of multiple doses at regular intervals, or prior to exposure to an agent (e.g., an allergen) to alter the course of the condition or disease. Moreover, a single agent may be used in a single individual for each prevention, amelioration, and treatment of a condition or disease sequentially, or concurrently. In a preferred method of the instant invention, the ASOs are delivered by aerosol for topical delivery to the respiratory tract, thereby limiting systemic exposure and reducing potential side effects.

Overview

Disclosed herein are oligomeric compounds, including antisense oligonucleotides and other antisense compounds for use in modulating the expression of nucleic acid molecules encoding IL 4R-α. This is accomplished by providing oligomeric compounds that hybridize with one or more target nucleic acid molecules encoding IL 4R-α. As used herein, the terms "target nucleic acid" and "nucleic acid molecule encoding IL 4R-α" have been used for convenience to encompass DNA encoding IL 4R-α, RNA (including pre-mRNA and mRNA or portions thereof) transcribed from such DNA, and also cDNA derived from such RNA. In a preferred embodiment, the target nucleic acid is an mRNA encoding IL 4R-α.

The principle behind antisense technology is that an antisense compound that hybridizes to a target nucleic acid, modulates gene expression activities such as transcription or translation. This sequence specificity makes antisense compounds extremely attractive as tools for target validation and gene functionalization, as well as therapeutics to selectively modulate the expression of genes involved in disease. Although not limited by mechanism of action, the compounds of the instant invention are proposed to work by an antisense, non-autocatalytic mechanism.

Compounds

The term "oligomeric compound" refers to a polymeric structure capable of hybridizing to a region of a nucleic acid molecule. This term includes oligonucleotides, oligonucleosides, oligonucleotide analogs, oligonucleotide mimetics, and chimeric combinations of these. Generally, oligomeric compounds comprise a plurality of monomeric subunits linked together by internucleoside linking groups and/or internucleoside linkage mimetics. Each of the monomeric subunits comprises a sugar, abasic sugar, modified sugar, or a sugar mimetic, and except for the abasic sugar includes a nucleobase, modified nucleobase or a nucleobase mimetic. Preferred monomeric subunits comprise nucleosides and modified nucleosides. Oligomeric compounds are routinely prepared linearly but can be joined or otherwise prepared to be circular. Moreover, branched structures are known in the art.

An "antisense compound" or "antisense oligomeric compound" refers to an oligomeric compound that is at least partially complementary to the region of a target nucleic acid molecule to which it hybridizes and which modulates (increases or decreases) its expression. Consequently, while all antisense compounds can be said to be oligomeric compounds, not all oligomeric compounds are antisense compounds. An "antisense oligonucleotide" is an antisense compound that is a nucleic acid-based oligomer. An antisense oligonucleotide can, in some cases, include one or more chemical modifications to the sugar, base, and/or internucleoside linkages. Nonlimiting examples of oligomeric compounds include primers, probes, antisense compounds, antisense oligonucleotides, external guide sequence (EGS) oligonucleotides, alternate splicers, and siRNAs. As such, these compounds can be introduced in the form of single-stranded, double-stranded, circular, branched or hairpins and can contain structural elements such as internal or terminal bulges or loops. Oligomeric double-stranded compounds can be two strands hybridized to form double-stranded compounds or a single strand with sufficient self complementarity to allow for hybridization and formation of a fully or partially double-stranded compound. The compounds of the instant invention are not auto-catalytic. As used herein, "auto-catalytic" means a compound has the ability to promote cleavage of the target RNA in the absence of accessory factors, e.g. proteins.

In one embodiment of the invention, the oligomeric compound is an antisense compound comprising a single stranded oligonucleotide. In some embodiments of the invention the oligomeric compound contains chemical modifications. In a preferred embodiment, the antisense compound is a single stranded, chimeric oligonucleotide wherein the modifications of sugars, bases, and internucleoside linkages are independently selected.

The oligomeric compounds in accordance with this invention may comprise an oligomeric compound from about 12 to about 35 nucleobases (i.e. from about 12 to about 35 linked nucleosides). In other words, a single-stranded compound of the invention comprises from about 12 to about 35 nucleobases, and a double-stranded antisense compound of the invention (such as a siRNA, for example) comprises two strands, each of which is from about 12 to about 35 nucleobases. Contained within the oligomeric compounds of the invention (whether single or double stranded and on at least one strand) are antisense portions. The "antisense portion" is that part of the oligomeric compound that is designed to work by one of the aforementioned antisense mechanisms. One of ordinary skill in the art will appreciate that this comprehends antisense portions of 12, 13, 14, 15, 16, 17, 18, 19, 20, 21, 22, 23, 24, 25, 26, 27, 28, 29, 30, 31, 32, 33, 34, or 35 nucleobases.

In one embodiment, the antisense compounds of the invention have antisense portions of 12 to 35 nucleobases. It is understood that the antisense portion may be about 12, 13, 14, 15, 16, 17, 18, 19, 20, 21, 22, 23, 24, 25, 26, 27, 28, 29, 30, 31, 32, 33, 34, or 35 nucleobases in length.

Antisense compounds 12 to 35 nucleobases in length comprising a stretch of at least eight (8), preferably at least 12, more preferably at least 17 consecutive nucleobases selected from within the illustrative antisense compounds are considered to be suitable antisense compounds as well.

Compounds of the invention include oligonucleotide sequences that comprise at least the 8 consecutive nucleobases from the 5'-terminus of one of the illustrative antisense compounds (the remaining nucleobases being a consecutive stretch of the same oligonucleotide beginning immediately upstream of the 5-terminus of the antisense compound which is specifically hybridizable to the target nucleic acid and continuing until the oligonucleotide contains about 12 to 35 nucleobases). Other compounds are represented by oligonucleotide sequences that comprise at least the 8 consecutive nucleobases from the 3'-terminus of one of the illustrative antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains about 12 to about 35 nucleobases). It is also understood that compounds may be represented by oligonucleotide sequences that comprise at least 8 consecutive nucleobases from an internal portion of the sequence of an illustrative compound, and may extend in either or both directions until the oligonucleotide contains about 12 to about 35 nucleobases.

Modifications can be made to the compounds of the instant invention and may include conjugate groups attached to one of the termini, selected nucleobase positions, sugar positions or to one of the internucleoside linkages. Possible modifications include, but are not limited to, 2'-F and 2'-OMethyl sugar modifications, inverted abasic caps, deoxynucleobases, and nucleobase analogs such as locked nucleic acids (LNA).

In one embodiment of the invention, double-stranded antisense compounds encompass short interfering RNAs (siRNAs). As used herein, the term "siRNA" is defined as a double-stranded compound having a first and second strand, each strand having a central portion and two independent terminal portions. The central portion of the first strand is complementary to the central portion of the second strand, allowing hybridization of the strands. The terminal portions are independently, optionally complementary to the corresponding terminal portion of the complementary strand. The ends of the strands may be modified by the addition of one or more natural or modified nucleobases to form an overhang. In one nonlimiting example, the first strand of the siRNA is antisense to the target nucleic acid, while the second strand is complementary to the first strand. Once the antisense strand is designed to target a particular nucleic acid target, the sense strand of the siRNA can then be designed and synthesized as the complement of the antisense strand and either strand may contain modifications or additions to either terminus. For example, in one embodiment, both strands of the siRNA duplex would be complementary over the central nucleobases, each having overhangs at one or both termini. It is possible for one end of a duplex to be blunt and the other to have overhanging nucleobases. In one embodiment, the number of overhanging nucleobases is from 1 to 6 on the 3' end of each strand of the duplex. In another embodiment, the number of overhanging nucleobases is from 1 to 6 on the 3' end of only one strand of the duplex. In a further embodiment, the number of overhanging nucleobases is from 1 to 6 on one or both 5' ends of the duplexed strands. In another embodiment, the number of overhanging nucleobases is zero. In a preferred embodiment, each of the strands is 19 nucleobases in length, fully hybridizable with the complementary strand, and includes no overhangs.

Each strand of the siRNA duplex may be from about 12 to about 35 nucleobases. In a preferred embodiment, each strand of the siRNA duplex is about 17 to about 25 nucleobases. The central complementary portion may be from about 12 to about 35 nucleobases in length. In a preferred embodiment, the central complimentary portion is about 17 to about 25 nucleobases in length. It is understood that each the strand of the siRNA duplex and the central complementary portion may be about 12, 13, 14, 15, 16, 17, 18, 19, 20, 21, 22, 23, 24, 25, 26, 27, 28, 29, 30, 31, 32, 33, 34, or 35 nucleobases in length. The terminal portions can be from 1 to 6 nucleobases. It is understood that the terminal portions can be about 1, 2, 3, 4, 5, or 6 nucleobases in length. The siRNAs may also have no terminal portions. The two strands of an siRNA can be linked internally leaving free 3' or 5' termini, or can be linked to form a continuous hairpin structure or loop. The hairpin structure may contain an overhang on either the 5' or 3' terminus producing an extension of single-stranded character.

Double-stranded compounds can be made to include chemical modifications as discussed herein.

Chemical Modifications

As is known in the art, a nucleoside is a base-sugar combination. The base portion of the nucleoside is normally a heterocyclic base (sometimes referred to as a "nucleobase" or simply a "base"). The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound. Within oligonucleotides, the phosphate groups are commonly referred to as forming the internucleoside backbone of the oligonucleotide. The normal linkage or backbone of RNA and DNA is a 3' to 5' phosphodiester linkage. It is often preferable to include chemical modifications in oligonucleotides to alter their activity. Chemical modifications can alter oligonucleotide activity by, for example: increasing affinity of an antisense oligonucleotide for its target RNA, increasing nuclease resistance, and/or altering the pharmacokinetics of the oligonucleotide. The use of chemistries that increase the affinity of an oligonucleotide for its target can allow for the use of shorter oligonucleotide compounds.

The term "nucleobase" or "heterocyclic base moiety" as used herein, refers to the heterocyclic base portion of a nucleoside. In general, a nucleobase is any group that contains one or more atom or groups of atoms capable of hydrogen bonding to a base of another nucleic acid. In addition to "unmodified" or "natural" nucleobases such as the purine nucleobases adenine (A) and guanine (G), and the pyrimidine nucleobases thymine (T), cytosine (C) and uracil (U), many modified nucleobases or nucleobase mimetics known to the art skilled are amenable to the present invention. The terms modified nucleobase and nucleobase mimetic can overlap but generally a modified nucleobase refers to a nucleobase that is fairly similar in structure to the parent nucleobase such as for example a 7-deaza purine or a 5-methyl cytosine whereas a nucleobase mimetic would include more complicated structures such as for example a tricyclic phenoxazine nucleobase mimetic. Methods for preparation of the above noted modified nucleobases are well known to those skilled in the art.

Oligomeric compounds of the present invention may also contain one or more nucleosides having modified sugar moieties. The furanosyl sugar ring of a nucleoside can be modified in a number of ways including, but not limited to, addition of a substituent group, bridging of two non-geminal ring atoms to form a bicyclic nucleic acid (BNA) and substitution of an atom or group such as —S—, —N(R)— or —C($R_1$)($R_2$) for the ring oxygen at the 4'-position. Modified sugar moieties are well known and can be used to alter, typically increase, the affinity of the oligomeric compound for its target and/or increase nuclease resistance. A representative list of preferred modified sugars includes but is not limited to bicyclic modified sugars (BNA's), including LNA and ENA (4'-($CH_2$)$_2$—O-2' bridge); and substituted sugars, especially 2'-substituted sugars having a 2'-F, 2'-$OCH_3$ or a 2'-O($CH_2$)$_2$—$OCH_3$ substituent group. Sugars can also be replaced with sugar mimetic groups among others. Methods for the preparations of modified sugars are well known to those skilled in the art.

The present invention includes internucleoside linking groups that link the nucleosides or otherwise modified monomer units together thereby forming an oligomeric compound. The two main classes of internucleoside linking groups are defined by the presence or absence of a phosphorus atom. Representative phosphorus containing internucleoside linkages include, but are not limited to, phosphodiesters, phosphotriesters, methylphosphonates, phosphoramidate, and phosphorothioates. Representative non-phosphorus containing internucleoside linking groups include, but are not limited to, methylenemethylimino (—$CH_2$—N($CH_3$)—O—$CH_2$—), thiodiester (—O—C(O)—S—), thionocarbamate (—O—C(O)(NH)—S—); siloxane (—O—Si(H)$_2$—O—); and N,N'-dimethylhydrazine (—$CH_2$—N($CH_3$)—N($CH_3$)—). Oligomeric compounds having non-phosphorus internucleoside linking groups are referred to as oligonucleosides. Modified internucleoside linkages, compared to natural phosphodiester linkages, can be used to alter, typically increase, nuclease resistance of the oligomeric compound. Internucleoside linkages having a chiral atom can be prepared racemic, chiral, or as a mixture. Representative chiral internucleoside linkages include, but are not limited to, alkylphosphonates and phosphorothioates. Methods of preparation of phosphorous-containing and non-phosphorous-containing linkages are well known to those skilled in the art.

As used herein the term "mimetic" refers to groups that are substituted for a sugar, a nucleobase, and/or internucleoside linkage. Mimetics are groups that are structurally quite different (not simply a modification) but functionally similar to the linked nucleosides of oligonucleotides. Generally, a mimetic is used in place of the sugar or sugar-internucleoside linkage combination, and the nucleobase is maintained for hybridization to a selected target. Representative examples of a sugar mimetic include, but are not limited to, cyclohexenyl or morpholino. Representative examples of a mimetic for a sugar-internucleoside linkage combination include, but are not limited to, peptide nucleic acids (PNA) and morpholino groups linked by uncharged achiral linkages. In some instances a mimetic is used in place of the nucleobase. Representative nucleobase mimetics are well known in the art and include, but are not limited to, tricyclic phenoxazine analogs and universal bases (Berger et al., Nuc Acid Res. 2000, 28:2911-14, incorporated herein by reference). Methods of synthesis of sugar, nucleoside and nucleobase mimetics are well known to those skilled in the art.

As used herein the term "nucleoside" includes, nucleosides, abasic nucleosides, modified nucleosides, and nucleosides having mimetic bases and/or sugar groups.

In the context of this invention, the term "oligonucleotide" refers to an oligomeric compound which is an oligomer or polymer of ribonucleic acid (RNA) or deoxyribonucleic acid (DNA). This term includes oligonucleotides composed of naturally- and non-naturally-occurring nucleobases, sugars and covalent internucleoside linkages, possibly further including non-nucleic acid conjugates.

The present invention provides compounds having reactive phosphorus groups useful for forming internucleoside linkages including for example phosphodiester and phosphorothioate internucleoside linkages. Methods of preparation and/or purification of precursors or olgomeric compounds of the instant invention are not a limitation of the compositions or methods of the invention. Methods for synthesis and purification of DNA, RNA, and the oligomeric compounds of the instant invention are well known to those skilled in the art.

As used herein the term "chimeric oligomeric compound" refers to an oligomeric compound having at least one sugar, nucleobase and/or internucleoside linkage that is differentially modified as compared to the other sugars, nucleobases and internucleoside linkages within the same oligomeric compound. The remainder of the sugars, nucleobases and internucleoside linkages can be independently modified or unmodified provided that they are distinguishable from the differentially modified moiety or moieties. In general a chimeric oligomeric compound will have modified nucleosides that can be in isolated positions or grouped together in regions that will define a particular motif. Any combination of modifications and or mimetic groups can comprise a chimeric oligomeric compound of the present invention.

Chimeric oligomeric compounds typically contain at least one region modified so as to confer increased resistance to nuclease degradation, increased cellular uptake, and/or increased binding affinity for the target nucleic acid. An additional region of the oligomeric compound may serve as a substrate for enzymes capable of cleaving RNA:DNA or RNA:RNA hybrids. By way of example, RNase H is a cellular endonuclease that cleaves the RNA strand of an RNA:DNA duplex. Activation of RNase H, therefore, results in cleavage of the RNA target, thereby greatly enhancing the efficiency of inhibition of gene expression. Consequently, comparable results can often be obtained with shorter oligomeric compounds when chimeras are used, compared to for example phosphorothioate deoxyoligonucleotides hybridizing to the same target region. Cleavage of the RNA target can be routinely detected by gel electrophoresis and, if necessary, associated nucleic acid hybridization techniques known in the art.

Certain chimeric as well as non-chimeric oligomeric compounds can be further described as having a particular motif. As used in the present invention the term "motif" refers to the orientation of modified sugar moieties and/or sugar mimetic groups in an oligomeric compound relative to like or differentially modified or unmodified nucleosides. As used in the present invention, the terms "sugars", "sugar moieties" and "sugar mimetic groups' are used interchangeably. Such motifs include, but are not limited to, gapped motifs, alternating motifs, fully modified motifs, hemimer motifs, blockmer motifs, and positionally modified motifs. The sequence and the structure of the nucleobases and type of internucleoside linkage is not a factor in determining the motif of an oligomeric compound.

As used in the present invention the term "gapped motif" refers to an oligomeric compound comprising a contiguous sequence of nucleosides that is divided into 3 regions, an internal region (gap) flanked by two external regions (wings). The regions are differentiated from each other at least by having differentially modified sugar groups that comprise the nucleosides. In some embodiments, each modified region is uniformly modified (e.g. the modified sugar groups in a given region are identical); however, other motifs can be applied to regions. For example, the wings in a gapmer could have an alternating motif. The internal region or the gap may, in some instances, comprise uniform unmodified β-D-ribonucleosides or β-D-deoxyribonucleosides or can be a sequence of nucleosides having uniformly modified sugars. The nucleosides located in the gap of a gapped oligomeric compound have sugar moieties that are different than the modified sugar moieties in each of the wings.

As used in the present invention the term "alternating motif" refers to an oligomeric compound comprising a contiguous sequence of nucleosides comprising two differentially sugar modified nucleosides that alternate for essentially the entire sequence of the oligomeric compound, or for essentially the entire sequence of a region of an oligomeric compound. The pattern of alternation can be described by the formula: $5'-A(-L-B-L-A)_n(-L-B)nn-3'$ where A and B are nucleosides differentiated by having at least different sugar groups, each L is an internucleoside linking group, nn is preferably 0 or 1 and n is preferably from about 5 to about 11; however, the number may be larger than about 11. This formula also allows for even and odd lengths for alternating oligomeric compounds wherein the 3' and 5'-terminal nucleosides are the same (odd) or different (even).

As used in the present invention the term "fully modified motif" refers to an oligomeric compound comprising a contiguous sequence of nucleosides wherein essentially each nucleoside is a sugar modified nucleoside having uniform modification.

As used in the present invention the term "hemimer motif" refers to a sequence of nucleosides that have uniform sugar moieties (identical sugars, modified or unmodified) and wherein one of the 5'-end or the 3'-end has a sequence of from 2 to 12 nucleosides that are sugar modified nucleosides that are different from the other nucleosides in the hemimer modified oligomeric compound. An example of a typical hemimer is an oligomeric compound comprising β-D-deoxyribonucleosides having a contiguous sequence of sugar modified nucleosides at one of the termini.

As used in the present invention the term "blockmer motif" refers to a sequence of nucleosides that have uniform sugars (identical sugars, modified or unmodified) that is internally interrupted by a block of sugar modified nucleosides that are uniformly modified and wherein the modification is different from the other nucleosides. In one aspect of the present invention oligomeric compounds having a blockmer motif comprise a sequence of β-D-deoxyribonucleosides having one internal block of from 2 to 6 sugar modified nucleosides. The internal block region can be at any position within the oligomeric compound as long as it is not at one of the termini which would then make it a hemimer. Methods of preparation of chimeric oligonucleotide compounds are well known to those skilled in the art.

As used in the present invention the term "positionally modified motif" comprises all other motifs. Methods of preparation of positionally modified oligonucleotide compounds are well known to those skilled in the art.

The compounds described herein contain one or more asymmetric centers and thus give rise to enantiomers, diastereomers, and other stereoisomeric configurations that may be defined, in terms of absolute stereochemistry, as (R) or (S), a or β, or as (D) or (L) such as for amino acids et al. The present invention is meant to include all such possible isomers, as well as their racemic and optically pure forms.

In one aspect of the present invention oligomeric compounds are modified by covalent attachment of one or more conjugate groups. Conjugate groups may be attached by reversible or irreversible attachments. Conjugate groups may be attached directly to oligomeric compounds or by use of a linker. Linkers may be mono- or bifunctional linkers. Such attachment methods and linkers are well known to those skilled in the art. In general, conjugate groups are attached to oligomeric compounds to modify one or more properties. Such considerations are well known to those skilled in the art.

Oligomer Synthesis

Oligomerization of modified and unmodified nucleosides can be routinely performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

Oligomeric compounds of the present invention can be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The invention is not limited by the method of oligomer synthesis.

Oligomer Purification and Analysis

Methods of oligonucleotide purification and analysis are known to those skilled in the art. Analysis methods include capillary electrophoresis (CE) and electrospray-mass spectroscopy. Such synthesis and analysis methods can be performed in multi-well plates. The method of the invention is not limited by the method of oligomer purification.

Hybridization

"Hybridization" means the pairing of complementary strands of oligomeric compounds. While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An oligomeric compound is specifically hybridizable when there is a sufficient degree of complementarity to avoid non-specific binding of the oligomeric compound to non-target nucleic acid sequences under conditions in which specific binding is desired, i.e., under physiological conditions in the case of in vivo assays or therapeutic treatment, and under conditions in which assays are performed in the case of in vitro assays.

"Stringent hybridization conditions" or "stringent conditions" refers to conditions under which an oligomeric compound will hybridize to its target sequence, but to a minimal number of other sequences. Stringent conditions are sequence-dependent and will be different in different circumstances, and "stringent conditions" under which oligomeric compounds hybridize to a target sequence are determined by the nature and composition of the oligomeric compounds and the assays in which they are being investigated.

"Complementarity," as used herein, refers to the capacity for precise pairing between two nucleobases on one or two oligomeric compound strands. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be a complementary position. The oligomeric compound and the further DNA or RNA are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligomeric compound and a target nucleic acid.

Identity

Oligomeric compounds, or a portion thereof, may have a defined percent identity to a SEQ ID NO, or a compound having a specific Isis number. As used herein, a sequence is identical to the sequence disclosed herein if it has the same nucleobase pairing ability. For example, a RNA which contains uracil in place of thymidine in the disclosed sequences of the instant invention would be considered identical as they both pair with adenine. Similarly, a G-clamp modified heterocyclic base would be considered identical to a cytosine or a 5-Me cytosine in the sequences of the instant application as it pairs with a guanine. This identity may be over the entire length of the oligomeric compound, or in a portion of the oligomeric compound (e.g., nucleobases 1-20 of a 27-mer may be compared to a 20-mer to determine percent identity of the oligomeric compound to the SEQ ID NO.) It is understood by those skilled in the art that an oligonucleotide need not have an identical sequence to those described herein to function similarly to the oligonucleotides described herein. Shortened (i.e., deleted, and therefore non-identical) versions of oligonucleotides taught herein, or non-identical (e.g., one base replaced with another with non-identical nucleobase pairing, or abasic site) versions of the oligonucleotides taught herein fall within the scope of the invention. Percent identity is calculated according to the number of bases that have identical base pairing corresponding to the SEQ ID NO or compound to which it is being compared. The non-identical bases may be adjacent to each other, dispersed through out the oligonucleotide, or both.

For example, a 16-mer having the same sequence as nucleobases 2-17 of a 20-mer is 80% identical to the 20-mer. Alternatively, a 20-mer containing four nucleobases not identical to the 20-mer is also 80% identical to the 20-mer. A 14-mer having the same sequence as nucleobases 1-14 of an 18-mer is 78% identical to the 18-mer. Such calculations are well within the ability of those skilled in the art.

The percent identity is based on the percent of nucleobases in the original sequence present in a portion of the modified sequence. Therefore, a 30 nucleobase oligonucleotide comprising the full sequence of a 20 nucleobase SEQ ID NO would have a portion of 100% identity with the 20 nucleobase SEQ ID NO while further comprising an additional 10 nucleobase portion. In the context of the invention, the full length of the modified sequence may constitute a single portion. In a preferred embodiment, the oligonucleotides of the instant invention are at least about 80%, more preferably at least about 85%, most preferably at least about 90% identical to the active target segments and/or oligonucleotides presented herein.

It is well known by those skilled in the art that it is possible to increase or decrease the length of an antisense oligonucleotide and/or introduce mismatch bases without eliminating activity. For example, in Woolf et al. (Proc. Natl. Acad. Sci. USA 89:7305-7309. 1992, incorporated herein by reference), a series of oligomers 13-25 nucleobases in length were tested for their ability to induce cleavage of a target RNA in an oocyte injection model. Oligonucleotides 25 nucleobases in length with 8 or 11 mismatch bases near the ends of the oligonucleotide were able to direct specific cleavage of the target mRNA, albeit to a lesser extent than the oligonucleotide that contained no mismatches. Similarly, target specific cleavage was achieved using a 13 nucleobase oligomer, including those with 1 or 3 mismatches. Maher and Dolnick (Nuc. Acid. Res. 16:3341-3358.1988, incorporated herein by reference) tested a series of tandem 14 nucleobase oligonucleotides, and a 28 and 42 nucleobase oligonucleotide comprised of the sequence of two or three of the tandem oligonucleotides, respectively, for their ability to arrest translation of human DHFR in a rabbit reticulocyte assay. Each of the three 14 nucleobase oligonucleotides alone were able to inhibit translation, albeit at a more modest level, than the 28 or 42 nucleobase oligonucleotide.

Target Nucleic Acids

"Targeting" an oligomeric compound to a particular target nucleic acid molecule can be a multistep process. The process usually begins with the identification of a target nucleic acid whose expression is to be modulated. For example, the target nucleic acid can be a cellular gene (or mRNA transcribed from the gene) whose expression is associated with a particular disorder or disease state, or a nucleic acid molecule from an infectious agent. As disclosed herein, the target nucleic acid encodes IL-4R alpha.

Target Regions, Segments, and Sites

The targeting process usually also includes determination of at least one target region, segment, or site within the target nucleic acid for the antisense interaction to occur such that the desired effect, e.g., modulation of expression, will result. "Region" is defined as a portion of the target nucleic acid having at least one identifiable structure, function, or characteristic. Target regions include, but are not limited to translation initiation and termination regions, coding regions, open reading frames, introns, exons, 3'-untranslated regions (3'-UTR), and 5'-untranslated regions (5'-UTR). Within regions of target nucleic acids are segments. "Segments" are defined as smaller or sub-portions of regions within a target nucleic acid such as stop codons and start codons. "Sites," as used in the present invention, are defined as unique nucleobase positions within a target nucleic acid such as splice junctions. Such regions, segments, and sites are well known to those skilled in the art.

Variants

It is also known in the art that alternative RNA transcripts can be produced from the same genomic region of DNA. These alternative transcripts are generally known as "variants." More specifically, "pre-mRNA variants" are transcripts produced from the same genomic DNA that differ from other transcripts produced from the same genomic DNA in either their start or stop position and contain both intronic and exonic sequence. Variants can result in mRNA variants including, but not limited to, those with alternate splice junctions, or alternate initiation and termination codons. Variants in genomic and mRNA sequences can result in disease. Oligonucleotides to such variants are within the scope of the instant invention.

Target Names, Synonyms, Features

In accordance with the present invention are compositions and methods for modulating the expression of IL 4R-α (also known as Interleukin 4 alpha receptor; CD 124; IL-4Ra; interleukin 4 receptor alpha chain). Table 1 lists the GenBank accession numbers of sequences corresponding to nucleic acid molecules encoding IL 4R-α (nt=nucleotide), the date the version of the sequence was entered in GenBank, and the corresponding SEQ ID NO in the instant application, when assigned, each of which is incorporated herein by reference.

TABLE 1

Gene Targets

| Species | Genbank # | Genbank Date | SEQ ID NO |
| --- | --- | --- | --- |
| Human | BM738518.1 | 1 Mar. 2002 | |
| Human | nt 18636000 to 18689000 of NT_010393.14 | 19 Feb. 2004 | |
| Human | X52425.1 | 26 May 1992 | 1 |
| Mouse | AF000304.1 | 1 Dec. 1997 | |
| Mouse | assembled from M64868.1 and M64879.1 | Both 6 May 1996 | |
| Mouse | BB867141.1 | 9 Jul. 2003 | |
| Mouse | BC012309.1 | 3 Jan. 2005 | |
| Mouse | M27959.1 | 16 Sep. 1994 | |
| Mouse | M27960.1 | 12 Jun. 1993 | 2 |
| Mouse | M29854.1 | 12 Jun. 1993 | |

Modulation of Target Expression

Modulation of expression of a target nucleic acid can be achieved through alteration of any number of nucleic acid (DNA or RNA) functions. "Modulation" means a perturbation of function, for example, either an increase (stimulation or induction) or a decrease (inhibition or reduction) in expression. As another example, modulation of expression can include perturbing splice site selection of pre-mRNA processing. "Expression" includes all the functions by which a gene's coded information is converted into structures present and operating in a cell. These structures include the products of transcription and translation. "Modulation of expression" means the perturbation of such functions. The functions of RNA to be modulated can include translocation functions, which include, but are not limited to, translocation of the RNA to a site of protein translation, translocation of the RNA to sites within the cell which are distant from the site of RNA synthesis, and translation of protein from the RNA. RNA processing functions that can be modulated include, but are not limited to, splicing of the RNA to yield one or more RNA species, capping of the RNA, 3' maturation of the RNA and catalytic activity or complex formation involving the RNA which may be engaged in or facilitated by the RNA. Modulation of expression can result in the increased level of one or more nucleic acid species or the decreased level of one or more nucleic acid species, either temporally or by net steady state level. One result of such interference with target nucleic acid function is modulation of the expression of IL 4R-α. Thus, in one embodiment modulation of expression can mean increase or decrease in target RNA or protein levels. In another embodiment modulation of expression can mean an increase or decrease of one or more RNA splice products, or a change in the ratio of two or more splice products.

The effect of oligomeric compounds of the present invention on target nucleic acid expression can be tested in any of a variety of cell types provided that the target nucleic acid is present at measurable levels. The effect of oligomeric compounds of the present invention on target nucleic acid expression can be routinely determined using, for example, PCR or Northern blot analysis. Cell lines are derived from both normal tissues and cell types and from cells associated with various disorders (e.g. hyperproliferative disorders). Cell lines derived from multiple tissues and species can be obtained from American Type Culture Collection (ATCC, Manassas, Va.) and are well known to those skilled in the art. Primary cells, or those cells which are isolated from an animal and not subjected to continuous culture, can be prepared according to methods known in the art or obtained from various commercial suppliers. Additionally, primary cells include those obtained from donor human subjects in a clinical setting (i.e. blood donors, surgical patients). Primary cells prepared by methods known in the art.

Assaying Modulation of Expression

Modulation of IL 4R-α expression can be assayed in a variety of ways known in the art. IL 4R-α mRNA levels can be quantitated by, e.g., Northern blot analysis, competitive polymerase chain reaction (PCR), or real-time PCR. RNA analysis can be performed on total cellular RNA or poly(A)+ mRNA by methods known in the art. Methods of RNA isolation are taught in, for example, Ausubel, F. M. et al., *Current Protocols in Molecular Biology*, Volume 1, pp. 4.1.1-4.2.9 and 4.5.1-4.5.3, John Wiley & Sons, Inc., 1993.

Northern blot analysis is routine in the art and is taught in, for example, Ausubel, F. M. et al., *Current Protocols in Molecular Biology*, Volume 1, pp. 4.2.1-4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions. The method of analysis of modulation of RNA levels is not a limitation of the instant invention.

Levels of a protein encoded by IL 4R-α can be quantitated in a variety of ways well known in the art, such as immunoprecipitation, Western blot analysis (immunoblotting), ELISA or fluorescence-activated cell sorting (FACS). Antibodies directed to a protein encoded by IL 4R-α can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., *Current Protocols in Molecular Biology*, Volume 2, pp. 11.12.1-11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1-11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1-10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1-11.2.22, John Wiley & Sons, Inc., 1991.

Validated Target Segments

The locations on the target nucleic acid to which active oligomeric compounds hybridize are herein below referred to as "validated target segments." As used herein the term "validated target segment" is defined as at least an 8-nucleobase portion of a target region, preferably at least a 12-nucleobase portion of a target region, to which an active oligomeric compound is targeted. While not wishing to be bound by theory, it is presently believed that these target segments represent portions of the target nucleic acid which are accessible for hybridization.

Target segments can include DNA or RNA sequences that comprise at least the 8, preferably 12 consecutive nucleobases from the 5'-terminus of a validated target segment (the remaining nucleobases being a consecutive stretch of the same DNA or RNA beginning immediately upstream of the 5'-terminus of the target segment and continuing until the DNA or RNA contains about 12 to about 35 nucleobases). Similarly validated target segments are represented by DNA or RNA sequences that comprise at least the 8, preferably 12 consecutive nucleobases from the 3-terminus of a validated target segment (the remaining nucleobases being a consecutive stretch of the same DNA or RNA beginning immediately downstream of the 3'-terminus of the target segment and continuing until the DNA or RNA contains about 12 to about 35 nucleobases). It is also understood that a validated oligomeric target segment can be represented by DNA or RNA sequences that comprise at least 8, preferably 12 consecutive nucleobases from an internal portion of the sequence of a validated target segment, and can extend in either or both directions until the oligonucleotide contains about 12 to about 35 nucleobases.

Screening for Modulator Oligomeric Compounds

In another embodiment, the validated target segments identified herein can be employed in a screen for additional compounds that modulate the expression of IL 4R-α. "Modulators" are those compounds that modulate the expression of IL 4R-α and which comprise at least an 8-nucleobase portion which is complementary to a validated target segment. The screening method comprises the steps of contacting a validated target segment of a nucleic acid molecule encoding IL 4R-α with one or more candidate modulators, and selecting for one or more candidate modulators which perturb the expression of a nucleic acid molecule encoding IL 4R-α. Once it is shown that the candidate modulator or modulators are capable of modulating the expression of a nucleic acid molecule encoding IL 4R-α, the modulator can then be employed in further investigative studies of the function of IL 4R-α, or for use as a research, diagnostic, or therapeutic agent.

Modulator compounds of IL 4R-α can also be identified or further investigated using one or more phenotypic assays, each having measurable endpoints predictive of efficacy in the treatment of a particular disease state or condition. Phenotypic assays, kits and reagents for their use are well known to those skilled in the art.

Kits, Research Reagents, and Diagnostics

The oligomeric compounds of the present invention can be utilized for diagnostics, and as research reagents and kits. Furthermore, antisense compounds, which are able to inhibit gene expression with specificity, are often used by those of ordinary skill to elucidate the function of particular genes or to distinguish between functions of various members of a biological pathway.

For use in kits and diagnostics, the oligomeric compounds of the present invention, either alone or in combination with other compounds or therapeutics, can be used as tools in differential and/or combinatorial analyses to elucidate expression patterns of a portion or the entire complement of genes expressed within cells and tissues. Methods of gene expression analysis are well known to those skilled in the art.

Therapeutics

Compounds of the invention can be used to modulate the expression of IL 4R-α in an animal, such as a human. In one non-limiting embodiment, the methods comprise the step of administering to said animal an effective amount of an antisense compound that inhibits expression of IL 4R-α. In one embodiment, the antisense compounds of the present invention effectively inhibit the levels or function of IL 4R-α RNA. Because reduction in IL 4R-α mRNA levels can lead to alteration in IL 4R-α protein products of expression as well, such resultant alterations can also be measured. Antisense compounds of the present invention that effectively inhibit the level or function of IL 4R-α RNA or protein products of expression is considered an active antisense compound. In one embodiment, the antisense compounds of the invention inhibit the expression of IL 4R-α causing a reduction of RNA by at least 10%, by at least 20%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100%.

For example, the reduction of the expression of IL 4R-α can be measured in a bodily fluid, tissue or organ of the animal. Methods of obtaining samples for analysis, such as body fluids (e.g., sputum), tissues (e.g., biopsy), or organs, and methods of preparation of the samples to allow for analysis are well known to those skilled in the art. Methods for analysis of RNA and protein levels are discussed above and are well known to those skilled in the art. The effects of treatment can be assessed by measuring biomarkers associated with the target gene expression in the aforementioned fluids, tissues or organs, collected from an animal contacted with one or more compounds of the invention, by routine clinical methods known in the art. These biomarkers include but are not limited to: liver transaminases, bilirubin, albumin, blood urea nitrogen, creatine and other markers of kidney and liver function; interleukins, tumor necrosis factors, intracellular adhesion molecules, C-reactive protein and other markers of inflammation.

The compounds of the present invention can be utilized in pharmaceutical compositions by adding an effective amount of a compound to a suitable pharmaceutically acceptable diluent or carrier. Acceptable carriers and diluents are well known to those skilled in the art. Selection of a diluent or carrier is based on a number of factors, including, but not limited to, the solubility of the compound and the route of administration. Such considerations are well understood by those skilled in the art. In one aspect, the compounds of the present invention inhibit the expression of IL 4R-α. The compounds of the invention can also be used in the manufacture of a medicament for the treatment of diseases and disorders related to IL 4R-α expression.

Methods whereby bodily fluids, organs or tissues are contacted with an effective amount of one or more of the antisense compounds or compositions of the invention are also contemplated. Bodily fluids, organs or tissues can be contacted with one or more of the compounds of the invention resulting in modulation of IL 4R-α expression in the cells of bodily fluids, organs or tissues. An effective amount can be determined by monitoring the modulatory effect of the antisense compound or compounds or compositions on target nucleic acids or their products by methods routine to the skilled artisan.

Thus, provided herein is the use of an isolated single- or double-stranded oligomeric compound targeted to IL 4R-α in the manufacture of a medicament for the treatment of a disease or disorder by means of the method described above. In a preferred embodiment, the oliogmeric compound is a single stranded compound.

Salts, Prodrugs and Bioequivalents

The oligomeric compounds of the present invention comprise any pharmaceutically acceptable salts, esters, or salts of such esters, or any other functional chemical equivalent which, upon administration to an animal including a human, is capable of providing (directly or indirectly) the biologically active metabolite or residue thereof. Accordingly, for example, the disclosure is also drawn to prodrugs and pharmaceutically acceptable salts of the oligomeric compounds of the present invention, pharmaceutically acceptable salts of such prodrugs, and other bioequivalents.

The term "prodrug" indicates a therapeutic agent that is prepared in an inactive or less active form that is converted to an active form (i.e., drug) within the body or cells thereof by the action of endogenous enzymes, chemicals, and/or conditions. In particular, prodrug versions of the oligonucleotides of the invention are prepared as SATE ((S-acetyl-2-thioethyl) phosphate) derivatives according to the methods disclosed in WO 93/24510 or WO 94/26764. Prodrugs can also include oligomeric compounds wherein one or both ends comprise nucleobases that are cleaved (e.g., phosphodiester backbone linkages) to produce the active compound.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. Sodium salts of antisense oligonucleotides are useful and are well accepted for therapeutic administration to humans. In another embodiment, sodium salts of dsRNA compounds are also provided.

Formulations

The oligomeric compounds of the invention may also be admixed, encapsulated, conjugated or otherwise associated with other molecules, molecule structures or mixtures of compounds.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. In a preferred embodiment, administration is topical to the surface of the respiratory tract, particularly pulmonary, e.g., by nebulization, inhalation, or insufflation of powders or aerosols, by mouth and/or nose.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers, finely divided solid carriers, or both, and then, if necessary, shaping the product (e.g., into a specific particle size for delivery). In a preferred embodiment, the pharmaceutical formulations of the instant invention are prepared for pulmonary administration in an appropriate solvent, e.g., water or normal saline, possibly in a sterile formulation, with carriers or other agents to allow for the formation of droplets of the desired diameter for delivery using inhalers, nasal delivery devices, nebulizers, and other devices for pulmonary delivery. Alternatively, the pharmaceutical formulations of the instant invention may be formulated as dry powders for use in dry powder inhalers.

A "pharmaceutical carrier" or "excipient" can be a pharmaceutically acceptable solvent, suspending agent or any other pharmacologically inert vehicle for delivering one or more nucleic acids to an animal and are known in the art. The excipient may be liquid or solid and is selected, with the planned manner of administration in mind, so as to provide for the desired bulk, consistency, etc., when combined with a nucleic acid and the other components of a given pharmaceutical composition.

Combinations

Compositions of the invention can contain two or more oligomeric compounds. In another related embodiment, compositions of the present invention can contain one or more antisense compounds, particularly oligonucleotides, targeted to a first nucleic acid and one or more additional antisense compounds targeted to a second nucleic acid target. Alternatively, compositions of the present invention can contain two or more antisense compounds targeted to different regions of the same nucleic acid target. Two or more combined compounds may be used together or sequentially. Compositions of the instant invention can also be combined with other non-oligomeric compound therapeutic agents.

Nonlimiting Disclosure and Incorporation by Reference

While certain compounds, compositions and methods of the present invention have been described with specificity in accordance with certain embodiments, the following examples serve only to illustrate the compounds of the invention and are not intended to limit the same. Each of the references, GenBank accession numbers, and the like recited in the present application is incorporated herein by reference in its entirety.

EXAMPLE 1

Cell Types

The effect of oligomeric compounds on target nucleic acid expression was tested in the following cell types.

A549:

The human lung carcinoma cell line A549 was obtained from the American Type Culture Collection (Manassas, Va.). A549 cells were routinely cultured in DMEM, high glucose (Invitrogen Life Technologies, Carlsbad, Calif.) supplemented with 10% fetal bovine serum, 100 units per ml penicillin, and 100 micrograms per ml streptomycin (Invitrogen Life Technologies, Carlsbad, Calif.). Cells were routinely passaged by trypsinization and dilution when they reached approximately 90% confluence. Cells were seeded into 96-well plates (Falcon-Primaria #3872) at a density of approximately 5000 cells/well for use in oligomeric compound transfection experiments.

b.END:

The mouse brain endothelial cell line b.END was obtained from Dr. Werner Risau at the Max Plank Institute (Bad Nauheim, Germany). b.END cells were routinely cultured in DMEM, high glucose (Invitrogen Life Technologies, Carlsbad, Calif.) supplemented with 10% fetal bovine serum (Invitrogen Life Technologies, Carlsbad, Calif.). Cells were routinely passaged by trypsinization and dilution when they reached approximately 90% confluence. Cells were seeded into 96-well plates (Falcon-Primaria #353872, BD Biosciences, Bedford, Mass.) at a density of approximately 3000 cells/well for use in oligomeric compound transfection experiments.

Treatment with Oligomeric Compounds

When cells reach appropriate confluency, they are treated with oligonucleotide using a transfection lipid and method, such as Lipofectin™ essentially by the manufacturer's instructions, as described.

When cells reached 65-75% confluency, they were treated with oligonucleotide. Oligonucleotide was mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of oligonucleotide and a LIPOFECTIN™ concentration of 2.5 or 3 µg/mL per 100 nM oligonucleotide. This transfection mixture was incubated at room temperature for approximately 0.5 hours. For cells grown in 96-well plates, wells were washed once with 100 µL OPTI-MEM™-1 and then treated with 130 µL of the transfection mixture. Cells grown in 24-well plates or other standard tissue culture plates are treated similarly, using appropriate volumes of medium and oligonucleotide. Cells are treated and data are obtained in duplicate or triplicate. After approximately 4-7 hours of treatment at 37° C., the medium containing the transfection mixture was replaced with fresh culture medium. Cells were harvested 16-24 hours after oligonucleotide treatment.

Other transfection reagents and methods (e.g., electroporation) for delivery of oligonucleotides to the cell are well known. The method of delivery of oligonucleotide to the cells is not a limitation of the instant invention.

Control Oligonucleotides

Control oligonucleotides are used to determine the optimal oligomeric compound concentration for a particular cell line. Furthermore, when oligomeric compounds of the invention are tested in oligomeric compound screening experiments or phenotypic assays, control oligonucleotides are tested in parallel with compounds of the invention.

The concentration of oligonucleotide used varies from cell line to cell line. To determine the optimal oligonucleotide concentration for a particular cell line, the cells are treated with a positive control oligonucleotide at a range of concentrations. The concentration of positive control oligonucleotide that results in 80% inhibition of the target mRNA is then utilized as the screening concentration for new oligonucleotides in subsequent experiments for that cell line. If 80% inhibition is not achieved, the lowest concentration of positive control oligonucleotide that results in 60% inhibition of the target mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM when the antisense oligonucleotide is transfected using a liposome reagent and 11 M to 40 μM when the antisense oligonucleotide is transfected by electroporation.

EXAMPLE 2

Real-Time Quantitative PCR Analysis of IL 4R-α mRNA Levels

Quantitation of IL 4R-α mRNA levels was accomplished by real-time quantitative PCR using the ABI PRISM™ 7600, 7700, or 7900 Sequence Detection System (PE-Applied Biosystems, Foster City, Calif.) according to manufacturer's instructions.

Prior to quantitative PCR analysis, primer-probe sets specific to the target gene being measured were evaluated for their ability to be "multiplexed" with a GAPDH amplification reaction. After isolation the RNA is subjected to sequential reverse transcriptase (RT) reaction and real-time PCR, both of which are performed in the same well. RT and PCR reagents were obtained from Invitrogen Life Technologies (Carlsbad, Calif.). RT, real-time PCR was carried out in the same by adding 20 μL PCR cocktail (2.5×PCR buffer minus MgCl$_2$, 6.6 mM MgCl$_2$, 375 μM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 μL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by RT, real-time PCR were normalized using either the expression level of GAPDH, a gene whose expression is constant, or by quantifying total RNA using RiboGreen™ (Molecular Probes, Inc. Eugene, Oreg.). GAPDH expression was quantified by RT, real-time PCR, by being run simultaneously with the target, multiplexing, or separately. Total RNA was quantified using RiboGreen™ RNA quantification reagent (Molecular Probes, Inc. Eugene, Oreg.).

170 μL of RiboGreen™ working reagent (RiboGreen™ reagent diluted 1:350 in 10 mM Tris-HCl, 1 mM EDTA, pH 7.5) was pipetted into a 96-well plate containing 30 μL purified cellular RNA. The plate was read in a CytoFluor 4000 (PE Applied Biosystems) with excitation at 485 nm and emission at 530 nm.

The GAPDH PCR probes have JOE covalently linked to the 5' end and TAMRA or MGB covalently linked to the 3' end, where JOE is the fluorescent reporter dye and TAMRA or MGB is the quencher dye. In some cell types, primers and probe designed to a GAPDH sequence from a different species are used to measure GAPDH expression. For example, a human GAPDH primer and probe set is used to measure GAPDH expression in monkey-derived cells and cell lines.

Probes and primers for use in real-time PCR were designed to hybridize to target-specific sequences. The primers and probes and the target nucleic acid sequences to which they hybridize are presented in Table 2. The target-specific PCR probes have FAM covalently linked to the 5' end and TAMRA or MGB covalently linked to the 3' end, where FAM is the fluorescent dye and TAMRA or MGB is the quencher dye.

TABLE 2

Gene target-specific primers and probes for use in real-time PCR

| Target Name | Species | Target SEQ ID NO | Sequence Description | Sequence (5' to 3') | SEQ ID NO |
|---|---|---|---|---|---|
| IL-4R alpha | Human | 1 | Fwd Primer | AATGGTCCCACCAATTGCA | 3 |
| IL-4R alpha | Human | 1 | Reverse Primer | CTCCGTTGTTCTCAGGGATACAC | 4 |
| IL-4R alpha | Human | 1 | Probe | TTTTTCTGCTCTCCGAAGCCC | 5 |
| IL-4R alpha | Mouse | 2 | Fwd Primer | TCCCATTTTGTCCACCGAATA | 6 |
| IL-4R alpha | Mouse | 2 | Reverse Primer | GTTTCTAGGCCCAGCTTCCA | 7 |
| IL-4R alpha | Mouse | 2 | Probe | TGTCACTCAAGGCTCTCAGCGGTCC | 8 |

EXAMPLE 3

Antisense Inhibition of Mouse IL-4R alpha by Oligomeric Compounds

A series of oligomeric compounds was designed to target different regions of mouse IL 4R-α RNA, using published sequences cited in Table 1. The compounds are shown in Table 3. All compounds in Table 3 are chimeric oligonucleotides ("gapmers") 20 nucleotides in length, composed of a central "gap" region consisting of 10 2'-deoxynucleotides, which is flanked on both sides (5' and 3') by five-nucleotide "wings". The wings are composed of 2'-O-(2-methoxyethyl) nucleotides, also known as 2'-MOE nucleotides. The internucleoside (backbone) linkages are phosphorothioate throughout the oligonucleotide. All cytidine residues are 5-methylcytidines. The compounds were analyzed for their effect on gene target mRNA levels by quantitative real-time PCR as described in other examples herein, using the target-specific primers and probes shown in Table 2. Data are averages from two experiments in which b.END cells were treated with 150 nM of the compounds in Table 3 using Lipofectin™. A reduction in expression is expressed as percent inhibition in Table 3. If the target expression level of oligomeric compound-treated cell was higher than control, percent inhibition is expressed as zero inhibition. The target regions to which these oligomeric compounds are inhibitory are herein referred to as "validated target segments."

TABLE 3

Inhibition of mouse IL 4R-α mRNA levels by chimeric oligonucleotides having 2'-MOE wings and deoxy gap

| ISIS # | Target SEQ ID/ GenBank | Target Site | Sequence (5' to 3') | % Inhib | SEQ ID NO |
|---|---|---|---|---|---|
| 231931 | Assm.fr. M64868.1/ M64879.1 | 1364 | ACCCGCACAAGGTCCTGGGC | 20 | 9 |
| 231932 | Assm.fr. M64868.1/ M64879.1 | 2204 | CAGGTCTTACCATTACCACT | 33 | 10 |
| 231933 | Assm.fr. M64868.1/ M64879.1 | 2506 | GCCCACTCACTTCTGCAGGG | 50 | 11 |
| 231934 | Assm.fr. M64868.1/ M64879.1 | 2804 | CGGTTGTACCACGTGATGCT | 51 | 12 |
| 231935 | Assm.fr. M64868.1/ M64879.1 | 2813 | TGATACTCACGGTTGTACCA | 29 | 13 |
| 231936 | Assm.fr. M64868.1/ M64879.1 | 3327 | AGGAACTCACTTGGTAATGC | 9 | 14 |
| 231937 | Assm.fr. M64868.1/ M64879.1 | 3559 | TGTACCCTCTTACCTGTGCA | 30 | 15 |
| 231929 | BB867141.1 | 49 | CAAAAGGTGCCTGCGAGTTC | 19 | 16 |
| 231930 | BC012309.1 | 101 | GGCTGGGTTACAGGAACAAG | 0 | 17 |
| 231928 | M27959.1 | 900 | AGCTGGAAGTGGTTGTACCA | 23 | 18 |
| 231860 | 2 | 78 | AATCAGAAGCCAGGTCCCTC | 66 | 19 |
| 231861 | 2 | 209 | CAAAAGGTGCCTGCACAAGG | 34 | 20 |
| 231862 | 2 | 233 | TGCAAAGCCGCCCCATTGGG | 66 | 21 |
| 231863 | 2 | 244 | CAGGAACTTGGTGCAAAGCC | 60 | 22 |
| 231864 | 2 | 330 | TAGTCAGAGAAGCAGGTGGG | 44 | 23 |
| 231865 | 2 | 340 | AGTGCGGATGTAGTCAGAGA | 39 | 24 |
| 231866 | 2 | 388 | CTGAGAACTGCAGTCCACAG | 58 | 25 |
| 231867 | 2 | 438 | GTGAGGTTTTCAGAGAACTC | 28 | 26 |
| 231868 | 2 | 443 | TGCATGTGAGGTTTTCAGAG | 48 | 27 |
| 231869 | 2 | 611 | GTGTGAGGTTGTCTGGAGCT | 63 | 28 |
| 231870 | 2 | 624 | ACATTGGTGTGGAGTGTGAG | 38 | 29 |
| 231871 | 2 | 716 | CTCTGGAGATGTTGACCATG | 48 | 30 |
| 231872 | 2 | 721 | GTCCTCTCTGGAGATGTTGA | 43 | 31 |
| 231873 | 2 | 726 | GGGTTGTCCTCTCTGGAGAT | 32 | 32 |
| 231874 | 2 | 758 | TGTAGGTCACATTATAGACT | 66 | 33 |
| 231875 | 2 | 891 | GGGTTGTACCACGTGATGCT | 27 | 34 |

TABLE 3-continued

Inhibition of mouse IL 4R-α mRNA levels by chimeric oligonucleotides having 2'-MOE wings and deoxy gap

| ISIS # | Target SEQ ID/ GenBank | Target Site | Sequence (5' to 3') | % Inhib | SEQ ID NO |
|---|---|---|---|---|---|
| 231876 | 2 | 918 | TCACTCAGTCACAGATTTTC | 70 | 35 |
| 231877 | 2 | 1014 | AGCTGGAAGTCCATCTCCTG | 23 | 36 |
| 231878 | 2 | 1114 | CTTCTTAATCTTGGTAATGC | 40 | 37 |
| 231879 | 2 | 1121 | ACCATATCTTCTTAATCTTG | 25 | 38 |
| 231880 | 2 | 1126 | GTCCCACCATATCTTCTTAA | 11 | 39 |
| 231881 | 2 | 1131 | ATCTGGTCCCACCATATCTT | 36 | 40 |
| 231882 | 2 | 1136 | TGGGAATCTGGTCCCACCAT | 43 | 41 |
| 231883 | 2 | 1225 | GGTTGACTCCTGGCTTCGGG | 7 | 42 |
| 231884 | 2 | 1385 | GGACGGTCCTGCTGACCTCC | 65 | 43 |
| 231885 | 2 | 1390 | CCAGAGGACGGTCCTGCTGA | 55 | 44 |
| 231886 | 2 | 1395 | TCTGGCCAGAGGACGGTCCT | 65 | 45 |
| 231887 | 2 | 1424 | TACAGCGCACCACACTGACA | 80 | 46 |
| 231888 | 2 | 1430 | GCTCCATACAGCGCACCACA | 72 | 47 |
| 231889 | 2 | 1435 | AAACAGCTCCATACAGCGCA | 77 | 48 |
| 231890 | 2 | 1440 | GCCTCAAACAGCTCCATACA | 58 | 49 |
| 231891 | 2 | 1460 | CCTCCACATTCTGTACTGGG | 75 | 50 |
| 231892 | 2 | 1505 | CAGGTGACATGCTCAGGTCC | 63 | 51 |
| 231893 | 2 | 1510 | GTTCTCAGGTGACATGCTCA | 68 | 52 |
| 231894 | 2 | 1515 | CCGCTGTTCTCAGGTGACAT | 88 | 53 |
| 231895 | 2 | 1575 | AACAGGTTCTCAGTGAGCCG | 62 | 54 |
| 231896 | 2 | 1834 | CCGGTAGGCAGGATTGTCTG | 62 | 55 |
| 231897 | 2 | 1839 | AAACTCCGGTAGGCAGGATT | 68 | 56 |
| 231898 | 2 | 1844 | CACTAAAACTCCGGTAGGCA | 71 | 57 |
| 231899 | 2 | 1880 | CCAGCTCTCCAGGATTGGG | 68 | 58 |
| 231900 | 2 | 1960 | TGGTGGCCCTGAAGAATGGG | 30 | 59 |
| 231901 | 2 | 1991 | GGATCTGCTCCCAGCTCTCC | 85 | 60 |
| 231902 | 2 | 1996 | GTGAAGGATCTGCTCCCAGC | 80 | 61 |
| 231903 | 2 | 2001 | CTCATGTGAAGGATCTGCTC | 69 | 62 |
| 231904 | 2 | 2006 | GGACACTCATGTGAAGGATC | 52 | 63 |
| 231905 | 2 | 2011 | CTGCAGGACACTCATGTGAA | 67 | 64 |
| 231906 | 2 | 2079 | TTCACTGCCTGCACAAACTC | 60 | 65 |
| 231907 | 2 | 2084 | CCTGCTTCACTGCCTGCACA | 72 | 66 |
| 231908 | 2 | 2166 | CTGCTGAGCAGGCTCGAGAA | 51 | 67 |
| 231909 | 2 | 2437 | GTCATCCCCAAAGGGCTTGG | 69 | 68 |
| 231910 | 2 | 2442 | CCCAGGTCATCCCCAAAGGG | 71 | 69 |
| 231911 | 2 | 2469 | GTGAGGGACGAGTACACAAT | 68 | 70 |

TABLE 3-continued

Inhibition of mouse IL 4R-α mRNA levels by chimeric oligonucleotides having 2'-MOE wings and deoxy gap

| ISIS # | Target SEQ ID/ GenBank | Target Site | Sequence (5' to 3') | % Inhib | SEQ ID NO |
|---|---|---|---|---|---|
| 231912 | 2 | 2497 | TTGCTTCAGGTGGCCACACA | 69 | 71 |
| 231913 | 2 | 2502 | TGGTGTTGCTTCAGGTGGCC | 71 | 72 |
| 231914 | 2 | 2507 | GGCTGTGGTGTTGCTTCAGG | 51 | 73 |
| 231915 | 2 | 2719 | CTGGCTGGGAACAGGAGAGT | 64 | 74 |
| 231916 | 2 | 2788 | AGCAACAACAGCACACTCAC | 78 | 75 |
| 231917 | 2 | 2793 | ACCTCAGCAACAACAGCACA | 82 | 76 |
| 231918 | 2 | 2798 | CACAGACCTCAGCAACAACA | 78 | 77 |
| 231919 | 2 | 2827 | TCCCTGGCTTGGAGGAACCC | 62 | 78 |
| 231920 | 2 | 2859 | CCTGCCAGCTGGGCTGTCTC | 66 | 79 |
| 231921 | 2 | 2869 | TTCTGGGAAACCTGCCAGCT | 73 | 80 |
| 231922 | 2 | 3340 | ACTTTGGGCAATCAAGTTTG | 32 | 81 |
| 231923 | 2 | 3345 | CAGTGACTTTGGGCAATCAA | 64 | 82 |
| 231924 | 2 | 3350 | ACTGGCAGTGACTTTGGGCA | 59 | 83 |
| 231925 | 2 | 3355 | GGGTAACTGGCAGTGACTTT | 56 | 84 |
| 231926 | 2 | 3671 | TAAAGACTTTATTGACATAA | 41 | 85 |
| 231927 | 2 | 3678 | GACAAGATAAAGACTTTATT | 41 | 86 |

All oligonucleotides targeted to the following regions of a GenBank sequence assembled from assembled from M64868.1 and M64879.1 were effective at inhibiting expression of IL 4R-α at least 40% as can be determined by the table above: nucleotides 2506-2525 and 2804-2323. These are validated target segments. All oligonucleotides targeted to the following regions of SEQ ID NO: 2 were effective at inhibiting expression of IL 4R-α at least 40% as can be determined by the table above: nucleotides 78-97; 233-263; 330-349; 388-407; 443-462; 611-630; 716-740; 758-777; 918-9937; 1014-1033; 1114-1133; 1136-1155; 1385-1314; 1424-1459; 1505-1534; 1575-1594; 1834-1863; 1880-1899; 1991-2030; 2979-2103; 2166-2185; 2437-2461; 2469-2488; 2497-2526; 2719-2738; 2788-2817; 2827-2846; 2859-2888; 3345-3374; and 3671-3697. These are validated target segments.

EXAMPLE 4

Antisense Inhibition of Human IL 4R-α by Oligomeric Compounds

A series of oligomeric compounds was designed to target different regions of human IL 4R-α RNA, using published sequences cited in Table 1. The compounds are shown in Tables 4 and 5. All compounds in Tables 4 and 5 are chimeric oligonucleotides ("gapmers") 20 nucleotides in length, composed of a central "gap" region consisting of 10 2'-deoxynucleotides, which is flanked on both sides (5' and 3') by five-nucleotide "wings". The wings are composed of 2'-O-(2-methoxyethyl)nucleotides, also known as 2'-MOE nucleotides. The internucleoside (backbone) linkages are phosphorothioate throughout the oligonucleotide. All cytidine residues are 5-methylcytidines. The compounds were analyzed for their effect on gene target mRNA levels by quantitative real-time PCR as described in other examples herein, using the human target-specific primers and probes shown in Table 2. Data are averages from two experiments in which A549 cells were treated with 85 nM of the compounds in Table 4, and 70 nM of the compound in Table 5, using Lipofectin™. A reduction in expression is expressed as percent inhibition in Tables 4 and 5. If the target expression level of oligomeric compound-treated cell was higher than control, percent inhibition is expressed as zero inhibition. The target regions to which these oligomeric compounds are inhibitory are herein referred to as "validated target segments."

TABLE 4

Inhibition of human IL 4R-α mRNA levels by chimeric oligonucleotides having 2'-MOE wings and deoxy gap

| ISIS # | Target SEQ ID/ GenBank | Target Site | Sequence (5' to 3') | % Inhib | SEQ ID NO |
|---|---|---|---|---|---|
| 364941 | 1 | 21 | GTAAATCTTTAATTATCTGC | 9 | 87 |
| 364945 | 1 | 234 | CATGTTCCCAGAGCTTGCCA | 19 | 88 |
| 364946 | 1 | 246 | CTGCAAGACCTTCATGTTCC | 40 | 89 |
| 364947 | 1 | 287 | CAAGTAGAGATGCTCATGTA | 30 | 90 |
| 364948 | 1 | 317 | CAATTGGTGGGACCATTCAT | 36 | 91 |
| 364949 | 1 | 487 | ACAGCAGCTGCTGCCCAGCC | 51 | 92 |
| 364951 | 1 | 741 | AATCCCAGACTTCAGGGTGC | 45 | 93 |
| 364952 | 1 | 777 | GCACTGAGCCCAGGCCCTCA | 56 | 94 |
| 364953 | 1 | 917 | CTGACATAGCACAACAGGCA | 55 | 95 |
| 364954 | 1 | 931 | TAATCTTGGTGATGCTGACA | 48 | 96 |
| 364955 | 1 | 936 | TTTCTTAATCTTGGTGATGC | 25 | 97 |
| 364958 | 1 | 1160 | CCCTGGAAAGGCATCTCTTT | 54 | 98 |
| 364959 | 1 | 1175 | GCTGATTTTCCAGAGCCCTG | 59 | 99 |
| 364960 | 1 | 1182 | GCACCATGCTGATTTTCCAG | 57 | 100 |
| 364962 | 1 | 1492 | CCCAGGGCATGTGAGCACTC | 49 | 101 |
| 364963 | 1 | 1499 | AACTCATCCCAGGGCATGTG | 59 | 102 |
| 364964 | 1 | 1509 | TGCACTTGGGAACTCATCCC | 49 | 103 |
| 364965 | 1 | 1608 | GCAAGTCAGGTTGTCTGGAC | 54 | 104 |
| 364966 | 1 | 1708 | GTGGGTCTGGACCCAGCTCT | 46 | 105 |
| 364967 | 1 | 1716 | GGCCAGCAGTGGGTCTGGAC | 48 | 106 |
| 364968 | 1 | 1845 | TGCCCCATGCTGGAGGACAT | 37 | 107 |
| 364969 | 1 | 1976 | GAGAAGGCCTTGTAACCAGC | 53 | 108 |
| 364970 | 1 | 2000 | ACAGCACTGCTGGCAAGCAG | 35 | 109 |
| 364971 | 1 | 2038 | CCCCACTGCTAGCCCCAAAC | 24 | 110 |
| 364972 | 1 | 2043 | CTCTTCCCCACTGCTAGCCC | 25 | 111 |
| 364973 | 1 | 2058 | GAAAGGCTTATACCCCTCTT | 62 | 112 |
| 364974 | 1 | 2067 | GAGGTCTTGGAAAGGCTTAT | 55 | 113 |
| 364975 | 1 | 2082 | AGGGCAGCCAGGAATGAGGT | 42 | 114 |
| 364976 | 1 | 2087 | TCCCCAGGGCAGCCAGGAAT | 37 | 115 |
| 364977 | 1 | 2230 | GCTTTGGCATGTCCTCTACC | 50 | 116 |
| 364978 | 1 | 2301 | GGCTGAGTAGACAATGCCAC | 26 | 117 |
| 364979 | 1 | 2315 | AGGTGGCAGGTAAGGGCTGA | 39 | 118 |
| 364980 | 1 | 2390 | CCACAGCAAGGACTGGCCAT | 45 | 119 |
| 364981 | 1 | 2469 | CAGTGGAACCCCACCTGGAG | 23 | 120 |
| 364983 | 1 | 2541 | GAAGGATGATGAGGATTTAC | 51 | 121 |
| 364984 | 1 | 2548 | CAGGATGGAAGGATGATGAG | 41 | 122 |

TABLE 4-continued

Inhibition of human IL 4R-α mRNA levels by chimeric oligonucleotides having 2'-MOE wings and deoxy gap

| ISIS # | Target SEQ ID/ GenBank | Target Site | Sequence (5' to 3') | % Inhib | SEQ ID NO |
|---|---|---|---|---|---|
| 364985 | 1 | 2569 | AGCTCTGAGCATTGCCAGGG | 45 | 123 |
| 364986 | 1 | 2626 | CCCTCATGTATGTGGGTCCC | 48 | 124 |
| 364987 | 1 | 2643 | GACATGCACCTAAGAGACCC | 49 | 125 |
| 364988 | 1 | 2674 | TAGTCCTCATCTGCAGACTC | 50 | 126 |
| 364989 | 1 | 2731 | AATCTGCCAGCCTGGCTGCC | 41 | 127 |
| 364991 | 1 | 2751 | GGTTCTTCAAGTCTTTTGGA | 56 | 128 |
| 364993 | 1 | 2772 | GGCCAATCACCTTCATACCA | 47 | 129 |
| 364994 | 1 | 2836 | GAGCCCAGCCCAATGCTGGG | 7 | 130 |
| 364995 | 1 | 2856 | CTACTCTCATGGGATGTGGC | 61 | 131 |
| 364996 | 1 | 2861 | GCCCTCTACTCTCATGGGAT | 58 | 132 |
| 364997 | 1 | 2909 | GGCCTCAGTTTTCCTGCAGG | 30 | 133 |
| 364998 | 1 | 2915 | CCCAAGGGCCTCAGTTTTCC | 55 | 134 |
| 364999 | 1 | 2952 | GAGGGAGCAGCCAACAACTC | 31 | 135 |
| 365000 | 1 | 3048 | AGACAGAGGCAGGTGGGCCT | 35 | 136 |
| 365001 | 1 | 3053 | CAGTGAGACAGAGGCAGGTG | 63 | 137 |
| 365002 | 1 | 3103 | CAAGTCATTCCCTTGATGGC | 48 | 138 |
| 365004 | 1 | 3198 | ATCAACCTAAGGAAGCTCTG | 49 | 139 |
| 365005 | 1 | 3238 | TAACTGAACACCCCTTGACA | 6 | 140 |
| 365006 | 1 | 3290 | AATTGTCCCTGCTTTAGTCA | 16 | 141 |
| 365007 | 1 | 3297 | GGCAGCAAATTGTCCCTGCT | 55 | 142 |
| 365008 | 1 | 3303 | GTGTTTGGCAGCAAATTGTC | 46 | 143 |
| 365009 | 1 | 3420 | GGGTAACTGGTGCCTTATGC | 53 | 144 |
| 365010 | 1 | 3432 | GGCCAACATGCAGGGTAACT | 44 | 145 |
| 365011 | 1 | 3477 | ATTACTCAACCCAAGGTTCC | 20 | 146 |
| 365012 | 1 | 3572 | AAGAAACTTTATTTATACAA | 0 | 147 |
| 365013 | 1 | 3578 | GAGACAAAGAAACTTTATTT | 2 | 148 |
| 365014 | 18636000-18639000 of NT_010393.14 | 8231 | CCTAGAATTCAGTCTTCCCT | 41 | 149 |
| 365015 | 18636000-18639000 of NT_010393.14 | 20215 | GTTTCCATCTAGAGTACTAG | 35 | 150 |
| 365016 | 18636000-18639000 of NT_010393.14 | 27651 | GCCAAGGCACCTGCAGAGAG | 38 | 151 |
| 365017 | 18636000-18639000 of NT_010393.14 | 47104 | AGTGAGTGGCAGAGTCAGGA | 48 | 152 |

TABLE 4-continued

Inhibition of human IL 4R-α mRNA levels by chimeric oligonucleotides having 2'-MOE wings and deoxy gap

| ISIS # | Target SEQ ID/ GenBank | Target Site | Sequence (5' to 3') | % Inhib | SEQ ID NO |
|---|---|---|---|---|---|
| 365018 | 18636000-18639000 of NT_010393.14 | 49717 | CTTCCAGTGTCTGCAAAAGC | 0 | 153 |

TABLE 5

Inhibition of human IL 4R-α mRNA levels by chimeric oligonucleotides having 2'-MOE wings and deoxy gap

| ISIS # | Target SEQ ID NO | Target Site | Sequence (5' to 3') | % Inhib | SEQ ID NO |
|---|---|---|---|---|---|
| 364942 | 1 | 167 | AGCCACCCCATTGGGAGATG | 88 | 154 |
| 364943 | 1 | 173 | GAGCAAAGCCACCCCATTGG | 83 | 155 |
| 369527 | 1 | 176 | CCAGAGCAAAGCCACCCCAT | 51 | 156 |
| 369528 | 1 | 193 | TCACAGGGAACAGGAGCCCA | 48 | 157 |
| 369529 | 1 | 194 | CTCACAGGGAACAGGAGCCC | 62 | 158 |
| 369530 | 1 | 196 | AGCTCACAGGGAACAGGAGC | 44 | 159 |
| 369531 | 1 | 197 | CAGCTCACAGGGAACAGGAG | 54 | 160 |
| 369532 | 1 | 199 | GGCAGCTCACAGGGAACAGG | 69 | 161 |
| 369533 | 1 | 200 | AGGCAGCTCACAGGGAACAG | 64 | 162 |
| 369534 | 1 | 201 | CAGGCAGCTCACAGGGAACA | 64 | 163 |
| 369535 | 1 | 202 | CCAGGCAGCTCACAGGGAAC | 58 | 164 |
| 369536 | 1 | 203 | ACCAGGCAGCTCACAGGGAA | 65 | 165 |
| 369537 | 1 | 205 | GGACCAGGCAGCTCACAGGG | 63 | 166 |
| 369538 | 1 | 206 | AGGACCAGGCAGCTCACAGG | 74 | 167 |
| 369539 | 1 | 207 | CAGGACCAGGCAGCTCACAG | 66 | 168 |
| 369540 | 1 | 208 | GCAGGACCAGGCAGCTCACA | 57 | 169 |
| 369541 | 1 | 209 | AGCAGGACCAGGCAGCTCAC | 48 | 170 |
| 369542 | 1 | 210 | CAGCAGGACCAGGCAGCTCA | 46 | 171 |
| 369543 | 1 | 211 | GCAGCAGGACCAGGCAGCTC | 48 | 172 |
| 369544 | 1 | 212 | TGCAGCAGGACCAGGCAGCT | 39 | 173 |
| 369545 | 1 | 213 | CTGGAGCAGGACGAGGCAGC | 22 | 174 |
| 369546 | 1 | 215 | ACCTGCAGCAGGACCAGGCA | 38 | 175 |
| 369547 | 1 | 217 | CCACCTGCAGCAGGACCAGG | 63 | 176 |
| 369548 | 1 | 219 | TGCCACCTGCAGCAGGACCA | 57 | 177 |
| 369549 | 1 | 220 | TTGCCACCTGCAGCAGGACC | 61 | 178 |
| 369550 | 1 | 221 | CTTGCCACCTGCAGCAGGAC | 60 | 179 |
| 369551 | 1 | 222 | GCTTGCCACCTGCAGCAGGA | 44 | 180 |
| 369552 | 1 | 223 | AGCTTGCCACCTGCAGGAGG | 42 | 181 |
| 364944 | 1 | 224 | GAGCTTGCCACCTGCAGCAG | 56 | 182 |
| 369553 | 1 | 225 | AGAGCTTGCCACCTGCAGCA | 64 | 183 |
| 369554 | 1 | 226 | CAGAGCTTGCCACCTGCAGC | 65 | 184 |
| 369555 | 1 | 227 | CCAGAGCTTGCCACCTGCAG | 66 | 185 |
| 369556 | 1 | 228 | CCCAGAGCTTGCCACCTGCA | 70 | 186 |
| 369557 | 1 | 229 | TCCCAGAGCTTGCCACCTGC | 50 | 187 |
| 369558 | 1 | 284 | GTAGAGATGCTCATGTAGTC | 50 | 188 |
| 369559 | 1 | 353 | AAAACCAGCTGGTACAACAG | 40 | 189 |
| 369560 | 1 | 355 | GAAAACCAGCTGGTACAAC | 36 | 190 |
| 369561 | 1 | 428 | TCCATGAGCAGGTGGCACAC | 67 | 191 |
| 369562 | 1 | 429 | ATCCATGAGCAGGTGGCACA | 71 | 192 |
| 369563 | 1 | 430 | CATCCATGAGCAGGTGGCAC | 78 | 193 |
| 369564 | 1 | 431 | TCATCCATGAGCAGGTGGCA | 75 | 194 |
| 369565 | 1 | 494 | CCCTTCCACAGCAGCTGCTG | 78 | 195 |
| 369566 | 1 | 496 | AGCCCTTCCACAGCAGCTGC | 86 | 196 |
| 369567 | 1 | 497 | GAGCCCTTCCACAGCAGCTG | 71 | 197 |
| 369568 | 1 | 499 | AGGAGCCCTTCCACAGCAGC | 74 | 198 |
| 369569 | 1 | 500 | AAGGAGCCCTTCCACAGCAG | 76 | 199 |
| 369570 | 1 | 501 | GAAGGAGCCCTTCCACAGCA | 71 | 200 |
| 369571 | 1 | 502 | TGAAGGAGCCCTTCCACAGC | 54 | 201 |
| 369572 | 1 | 503 | TTGAAGGAGCCCTTCCACAG | 35 | 202 |
| 369573 | 1 | 504 | CTTGAAGGAGCCCTTCCACA | 51 | 203 |
| 369574 | 1 | 506 | GGCTTGAAGGAGCCCTTCCA | 40 | 204 |
| 369575 | 1 | 508 | TGGGCTTGAAGGAGCCCTTC | 0 | 205 |
| 369576 | 1 | 509 | CTGGGCTTGAAGGAGCCCTT | 0 | 206 |

TABLE 5-continued

Inhibition of human IL 4R-α mRNA levels by chimeric oligonucleotides having 2'-MOE wings and deoxy gap

| ISIS # | Target SEQ ID NO | Target Site | Sequence (5' to 3') | % Inhib | SEQ ID NO |
|---|---|---|---|---|---|
| 369577 | 1 | 510 | GCTGGGCTTGAAGGAGCCCT | 3 | 207 |
| 369578 | 1 | 530 | GCCCTGGGTTTCACATGCTC | 64 | 208 |
| 369579 | 1 | 531 | GGCCCTGGGTTTCACATGCT | 62 | 209 |
| 369580 | 1 | 619 | TATACAGGTAATTGTCAGGG | 53 | 210 |
| 369581 | 1 | 620 | TTATACAGGTAATTGTCAGG | 55 | 211 |
| 369582 | 1 | 621 | ATTATACAGGTAATTGTCAG | 40 | 212 |
| 369583 | 1 | 642 | GTTGACTGCATAGGTGAGAT | 70 | 213 |
| 369584 | 1 | 645 | AATGTTGACTGCATAGGTGA | 72 | 214 |
| 369585 | 1 | 647 | CAAATGTTGACTGCATAGGT | 68 | 215 |
| 369586 | 1 | 649 | TCCAAATGTTGACTGCATAG | 61 | 216 |
| 364950 | 1 | 735 | AGACTTCAGGGTGCTGGCTG | 45 | 217 |
| 369587 | 1 | 736 | CAGACTTCAGGGTGCTGGCT | 63 | 218 |
| 369588 | 1 | 737 | CCAGACTTCAGGGTGCTGGC | 63 | 219 |
| 369589 | 1 | 998 | TCCTGGATTATTATAGCCAC | 45 | 220 |
| 364956 | 1 | 999 | ATCCTGGATFATTATAGCCA | 39 | 221 |
| 369590 | 1 | 1000 | CATCCTGGATTATTATAGCC | 43 | 222 |
| 369591 | 1 | 1001 | GCATCCTGGATTATTATAGC | 51 | 223 |
| 369592 | 1 | 1003 | GAGCATCCTGGATTATTATA | 45 | 224 |
| 369593 | 1 | 1004 | TGAGCATCCTGGATTATTAT | 26 | 225 |
| 369594 | 1 | 1005 | CTGAGCATCCTGGATTATTA | 52 | 226 |
| 369595 | 1 | 1006 | CCTGAGCATCCTGGATTATT | 41 | 227 |
| 364957 | 1 | 1053 | GCACTTGGCTGGTTCCTGGC | 77 | 228 |
| 369596 | 1 | 1077 | GGTAAGACAATTCTTCCAGT | 77 | 229 |
| 369597 | 1 | 1078 | TGGTAAGACAATTCTTCCAG | 57 | 230 |
| 369598 | 1 | 1079 | TTGGTAAGACAATTCTTCCA | 66 | 231 |
| 369599 | 1 | 1080 | CTTGGTAAGACAATTCTTCC | 73 | 232 |
| 369600 | 1 | 1082 | AGCTTGGTAAGACAATTCTT | 66 | 233 |
| 369601 | 1 | 1083 | GAGCTTGGTAAGACAATTCT | 61 | 234 |
| 369602 | 1 | 1085 | AAGAGCTTGGTAAGACAATT | 64 | 235 |
| 369603 | 1 | 1087 | GCAAGAGCTTGGTAAGACAA | 64 | 236 |
| 369604 | 1 | 1088 | GGCAAGAGCTTGGTAAGACA | 76 | 237 |
| 369605 | 1 | 1090 | AGGGCAAGAGCTTGGTAAGA | 44 | 238 |
| 369606 | 1 | 1092 | ACAGGGCAAGAGCTTGGTAA | 64 | 239 |
| 369607 | 1 | 1093 | AACAGGGCAAGAGCTTGGTA | 69 | 240 |
| 369608 | 1 | 1094 | AAACAGGGCAAGAGCTTGGT | 77 | 241 |
| 369609 | 1 | 1095 | AAAACAGGGCAAGAGCTTGG | 62 | 242 |
| 369610 | 1 | 1096 | GAAAACAGGGCAAGAGCTTG | 54 | 243 |
| 369611 | 1 | 1098 | CAGAAAACAGGGCAAGAGCT | 62 | 244 |
| 369612 | 1 | 1100 | TCCAGAAAACAGGGCAAGAG | 72 | 245 |
| 369613 | 1 | 1184 | GGGCACCATGCTGATTTTCC | 71 | 246 |
| 369614 | 1 | 1221 | GCTCTGTGGCCAGAGGACTG | 80 | 247 |
| 369615 | 1 | 1223 | ATGCTCTCTGGCCAGAGGAC | 68 | 248 |
| 369616 | 1 | 1224 | GATGCTCTCTGGCCAGAGGA | 58 | 249 |
| 369617 | 1 | 1227 | GCTGATGCTCTCTGGCCAGA | 64 | 250 |
| 369618 | 1 | 1395 | GTCCAGGAACAGGCTCTCTG | 76 | 251 |
| 369619 | 1 | 1397 | AGGTCCAGGAACAGGCTCTC | 68 | 252 |
| 369620 | 1 | 1398 | CAGGTCCAGGAACAGGCTCT | 43 | 253 |
| 369621 | 1 | 1399 | GCAGGTCCAGGAACAGGCTC | 59 | 254 |
| 369622 | 1 | 1400 | AGCAGGTCCAGGAACAGGCT | 45 | 255 |
| 364961 | 1 | 1401 | GAGCAGGTCCAGGAACAGGC | 54 | 256 |
| 369623 | 1 | 1506 | ACTTGGGAACTCATCCCAGG | 58 | 257 |
| 369624 | 1 | 1507 | CACTTGGGAACTCATCCCAG | 58 | 258 |
| 369625 | 1 | 1508 | GCACTTGGGAACTCATCCCA | 66 | 259 |
| 369626 | 1 | 1670 | CTCAGGGAGTTGCTGAAGCT | 63 | 260 |
| 369627 | 1 | 1671 | GCTCAGGGAGTTGCTGAAGC | 62 | 261 |
| 369628 | 1 | 1673 | TGGCTCAGGGAGTTGCTGAA | 28 | 262 |
| 369629 | 1 | 1674 | CTGGCTCAGGGAGTTGCTGA | 47 | 263 |
| 369630 | 1 | 1676 | GACTGGCTCAGGGAGTTGCT | 65 | 264 |
| 369631 | 1 | 1700 | GGACCCAGCTCTCTGGGACA | 57 | 265 |
| 369632 | 1 | 1701 | TGGACCCAGCTCTCTGGGAC | 61 | 266 |
| 369633 | 1 | 1703 | TCTGGACCCAGCTCTCTGGG | 46 | 267 |
| 369634 | 1 | 1705 | GGTCTGGACCCAGCTCTCTG | 70 | 268 |
| 369635 | 1 | 1706 | GGGTCTGGACCCAGCTCTCT | 65 | 269 |
| 369636 | 1 | 1777 | TGGTTGGCTCAGAGAGCTGG | 63 | 270 |
| 369637 | 1 | 1779 | AGTGGTTGGCTCAGAGAGCT | 51 | 271 |
| 369638 | 1 | 1780 | CAGTGGTTGGCTCAGAGAGC | 64 | 272 |
| 369639 | 1 | 1781 | ACAGTGGTTGGCTCAGAGAG | 57 | 273 |
| 369640 | 1 | 1782 | CACAGTGGTTGGCTCAGAGA | 71 | 274 |
| 369641 | 1 | 1997 | GCACTGCTGGCAAGCAGGCT | 52 | 275 |
| 369642 | 1 | 2056 | AAGGCTTATACCCCTCTTCC | 81 | 276 |
| 369643 | 1 | 2057 | AAAGGCTTATACCCCTCTTC | 82 | 277 |

TABLE 5-continued

Inhibition of human IL 4R-α mRNA levels by chimeric oligonucleotides having 2'-MOE wings and deoxy gap

| ISIS # | Target SEQ ID NO | Target Site | Sequence (5' to 3') | % Inhib | SEQ ID NO |
|---|---|---|---|---|---|
| 364973 | 1 | 2058 | GAAAGGCTTATACCCCTCTT | 60 | 112 |
| 369644 | 1 | 2059 | GGAAAGGCTTATACCCCTCT | 80 | 279 |
| 369645 | 1 | 2060 | TGGAAAGGCTTATACCCCTC | 84 | 280 |
| 369646 | 1 | 2062 | CTTGGAAAGGCTTATACCCC | 68 | 281 |
| 369647 | 1 | 2064 | GTCTTGGAAAGGCTTATACC | 59 | 282 |
| 369648 | 1 | 2065 | GGTCTTGGAAAGGCTTATAC | 58 | 283 |
| 369649 | 1 | 2066 | AGGTCTTGGAAAGGCTTATA | 77 | 284 |
| 364974 | 1 | 2067 | GAGGTCTTGGAAAGGCTTAT | 60 | 113 |
| 369650 | 1 | 2068 | TGAGGTCTTGGAAAGGGTTA | 59 | 286 |
| 369651 | 1 | 2126 | AGTCCAAAGGTGAACAAGGG | 50 | 287 |
| 369652 | 1 | 2128 | CCAGTCCAAAGGTGAACAAG | 55 | 288 |
| 369653 | 1 | 2130 | GTCCAGTCCAAAGGTGAACA | 50 | 289 |
| 369654 | 1 | 2131 | TGTCCAGTCCAAAGGTGAAC | 52 | 290 |
| 369655 | 1 | 2403 | TCCACAGCAGCAGCCACAGC | 57 | 291 |
| 369656 | 1 | 2524 | TACTCTTCTCTGAGATGCCC | 86 | 292 |
| 369657 | 1 | 2526 | TTTACTCTTCTCTGAGATGC | 71 | 293 |
| 369658 | 1 | 2528 | GATTTACTCTTCTCTGAGAT | 57 | 294 |
| 369659 | 1 | 2529 | GGATTTACTCTTCTCTGAGA | 67 | 295 |
| 364982 | 1 | 2530 | AGGATTTACTCTTCTCTGAG | 68 | 296 |
| 369660 | 1 | 2531 | GAGGATTTACTCTTCTCTGA | 87 | 297 |
| 369661 | 1 | 2532 | TGAGGATTTACTCTTCTCTG | 83 | 298 |
| 369662 | 1 | 2578 | TCTGGCTTGAGCTCTGAGCA | 69 | 299 |
| 369663 | 1 | 2579 | GTCTGGCTTGAGCTCTGAGC | 68 | 300 |
| 364990 | 1 | 2743 | AAGTCTTTTGGAAATCTGCC | 69 | 301 |
| 364992 | 1 | 2763 | CCTTCATACCATGGTTCTTC | 81 | 302 |
| 365003 | 1 | 3168 | GAGCACCTCTAGGCAATGAC | 82 | 303 |

Oligonucleotides targeted to the following nucleotides of SEQ ID NO: 3 were effective at inhibiting the expression of human IL 4R-α at least about 40% as can be determined by the tables above: nucleotides 167-265; 284-303; 353-372; 428-450; 487-525; 530-550; 619-640; 642-668; 735-760; 777-796; 917-950; 998-1025; 1053-1072; 1077-1121; 1160-1203; 1221-1246; 1395-1420; 1492-1528; 1608-1627; 1670-1695; 1700-1735; 1777-1801; 1976-1995; 1997-2016; 2056-2088; 2056-2101; 2126-2150; 2230-2349; 2390-2422; 2524-2598; 2626-2662; 2674-2693; 2731-2791; 2856-2880; 2915-2934; 3053-3072; 3103-3122; 3168-3187; 3198-3217; 3297-3322; and 3420-3451. These are validated target segments. Although some oligonucleotides within each nucleotide region did not inhibit expression at least 40%, they substantially overlapped (i.e., at least 80% overlapped) oligonucleotides effective at inhibiting expression at least 40%. All oligonucleotides targeted to the following regions of SEQ ID NO: 1 were effective at inhibiting expression of IL 4R-α at least 50% as can be determined by the tables above: nucleotides 284-303; 428-450; 494-525; 530-550; 642-668; 1053-1072; 1184-1203; 1221-1246; 1506-1527; 1777-1801; 1976-2016; 2056-2101; 2126-2150; 2230-2349; 2403-2422; 2524-2551; 2578-2598; 2743-2782; 2856-2880; 2915-2934 and 3168-3187. These are validated target segments. All oligonucleotides targeted to the following regions of GenBank nucleotides 18636000-18639000 of NT_010393.14 were effective at inhibiting expression of IL 4R-α at least 40% as can be determined by the table above: nucleotides 8231-8250 and 47104-47123. These are validated target segments.

EXAMPLE 5

Screening of Oligonucleotides Containing Nucleotide Mismatches, Dose Response

Based on the screening above, ISIS 231894 was selected for further study. A series of oligonucleotides were designed based on ISIS 231894 containing 1, 3, 5, and 7 mismatch nucleobases as shown in Table 6 below. It should be noted that the mismatches are interspersed throughout the central portion of the compounds, rather than at the ends. This decreases the affinity of the oligonucleotide for the target mRNA more than mismatch oligonucleotides at the ends. Such concepts are well known and understood by those skilled in the art. The oligonucleotides are 5-10-5 MOE-gapmers, as is ISIS 231894. All cytidine residues are 5-methylcytidines. The mismatch bases are underlined.

TABLE 6

Oligonucleotides targeted to mouse IL 4R-α containing mismatches

| ISIS # | Target SEQ ID NO | # mis-match | Sequence (5' to 3') | SEQ ID NO |
|---|---|---|---|---|
| 231894 | 2 | 0 | CCGCTGTTCTCAGGTGACAT | 53 |
| 352489 | 2 | 1 | CCGCTGTTC_T_CAGGTGACAT | 53 |
| 352490 | 2 | 3 | CCGCTG_A_TC_A_CAG_C_TGACAT | 304 |
| 352491 | 2 | 5 | CCGCT_C_ATC_A_CT_G_CTGACAT | 305 |
| 352492 | 2 | 7 | CC_A_CT_C_ATC_A_CT_G_CTGAC_TT_ | 306 |

The compounds were analyzed for their effect on gene target mRNA levels by quantitative real-time PCR as described in other examples herein using the target specific primers shown in Table 2. Data are averages from two experiments in which b.END cells were treated with the concentrations of the compounds listed.

TABLE 7

Inhibition of mouse IL 4R-α by chimeric, mismatch oligonucleotides

| Isis No | Number mismatch | 1 nM | 5 nM | 10 nM | 25 nM | 50 nM | 100 nM | SEQ ID NO |
|---|---|---|---|---|---|---|---|---|
| 231894 | Parent | 100 | 54 | 43 | 31 | 21 | 21 | 53 |
| 352489 | 1 mm | 74 | 55 | 52 | 51 | 44 | 49 | 53 |
| 352490 | 3 mm | 92 | 106 | 98 | 88 | 89 | 88 | 304 |
| 352491 | 5 mm | 104 | 104 | 97 | 102 | 114 | 90 | 305 |
| 352492 | 7 mm | 109 | 118 | 121 | 104 | 88 | 69 | 306 |

Oligonucleotides having at least three mismatched bases interspersed within the central portion of the compound were not able to reduce the expression of the target RNA by at least 40% even at the highest doses of oligonucleotide tested.

EXAMPLE 6

Mouse Models of Allergic Inflammation

Asthma is a complex disease with variations on disease severity and duration. In view of this, multiple animal models have been designed to reflect various aspects of the disease (see FIG. 1). It is understood that the models have some flexibility in regard to days of sensitization and treatment, and that the timelines provided reflect the days used herein. There are several important features common to human asthma and the mouse model of allergic inflammation. One of these is pulmonary inflammation, in which production of Th2 cytokines, e.g., IL 4, IL 5, IL 9, and IL 13 is dominant. Another is goblet cell metaplasia with increased mucus production. Lastly, airway hyperresponsiveness (AHR) occurs, resulting in increased sensitivity to cholinergic receptor agonists such as acetylcholine or methacholine.

Ovalbumin Induced Allergic Inflammation-Acute Model

The acute model of induced allergic inflammation is a prophylaxis treatment paradigm. Animals are sensitized to allergen by systemic administration (i.e., intraperitoneal injection), and treated with the therapeutic agent prior to administration of the pulmonary allergen challenge (see FIG. 1A). In this model, there is essentially no pulmonary inflammation prior to administration of the therapeutic agent.

Balb/c mice (Charles River Laboratory, Taconic Farms, N.Y.) were maintained in micro-isolator cages housed in a specific pathogen free (SPF) facility. The sentinel cages within the animal colony surveyed negative for viral antibodies and the presence of known mouse pathogens. Mice were sensitized and challenged with aerosolized chicken OVA. Briefly, 20 ug of alum precipitated OVA was injected intraperitoneally on days 0 and 14. On days 24, 25 and 26, the animals were exposed for 20 minutes to 1% OVA (in saline) by ultrasonic nebulization. On days 17, 19, 21, 24 and 26 animals were dosed with 1 ug/kg or 10 ug/kg of ISIS 231894 or the mismatch control oligonucleotide using an aerosol delivery system. Oligonucleotides were suspended in 0.9% sodium chloride and delivered via inhalation using a nose-only exposure system. A Lovelace nebulizer (Model 01-100) was used to deliver the oligonucleotide into an air flow rate of 1.0 liter per minute feeding into a total flow rate of 10 liters per minute. The exposure chamber was equilibrated with an oligonucleotide aerosol solution for 5 minutes before mice were placed in a restraint tubes attached to the chamber. Restrained mice were treated for a total of 10 minutes. Analysis was performed on day 28.

Airway Hyperreponsiveness in Response to Methacholine

Airway responsiveness was assessed by inducing airflow obstruction with a methacholine aerosol using a noninvasive method. This method used unrestrained conscious mice that are placed into a test chamber of a plethsmograph (Buxco Electronics, Inc. Troy, N.Y.). Pressure difference between this chamber and a reference chamber were used extrapolate minute volume, breathing frequency and enhanced pause (Penh). Penh is a dimensionless parameter that is a function of total pulmonary airflow in mice (i.e. the sum of the airflow in the upper and lower respiratory tracts) during the respiratory cycle of the animal. The lower the Penh, the greater the airflow. This parameter is known to closely correlate with lung resistance as measured by traditional, invasive techniques using ventilated animals as shown below (see also Hamelmann et al., 1997).

ISIS 231894, but not the mismatch control oligonucleotide, caused a significant (p 0.05 for both 1 ug/kg and 10 ug/kg vs. vehicle treated controls) dose dependent suppression in methacholine induced AHR in sensitized mice as measured by whole body plethysmography.

Airway hyperresponsiveness to methacholine challenge was also evaluated using an invasive technique designed to monitor changes in airway resistance and pulmonary compliance. Mice were weighed and anesthetized with ketamine (150 mg/kg) mixed with xylazine (10 mg/kg). A trachestomy was performed and the mice were ventilated using the Flexivent system (SCIREQ, Montreal, Canada) using traditional mouse parameters (Adler, A et al. J Appl Physiol 97: 286-292, 2004). Increasing concentrations of methacholine were aerosolized using the Flexivent system with an Aeroneb lab nebulizer system, and resistance (RL) and compliance (CL) were measured.

ISIS 231894, but not the mismatch control oligonucleotide, reduced airway resistance (p<0.05 for 100 ug/kg vs. vehicle treated controls) and increased lung compliance (p<0.05 for 100 ug/kg vs. vehicle treated controls) compared to measurements performed in control animals that inhaled saline only.

Data are presented as group means +/−SEM, N=4-6/group. *p<0.05 vs. vehicle treated controls by Student's T-test.

TABLE 8

Measurement of AHR by Flexivent in response to methacholine in the acute mouse OVA model

| | Resistance (cm H2O-S/mL) | Compliance (mL/cm H2O) |
|---|---|---|
| Naïve | 1.54 +/− 0.21* | 0.029 +/− 0.005* |
| Vehicle | 4.51 +/− 1.12 | 0.010 +/− 0.003 |
| 231894 | 1.70 +/− 0.34* | 0.030 +/− 0.006* |
| 352492 | 3.40 +/− 0.65 | 0.014 +/− 0.004 |

These data confirm that oligonucleotides targeted to IL 4R-α is effective in the treatment of AHR in a prophylaxis paradigm.

Inflammatory Cell Infiltration

The effect of ISIS 231894 on inflammatory cell profiles was analyzed. Cell differentials were performed on bronchial alveolar lavage (BAL) fluid collected from lungs of the treated mice after injection of a lethal dose of ketamine. Treatment with ISIS 231894, but not the mismatch control, resulted in a significant (p 0.05 for both 1 ug/kg and 10 ug/kg vs. vehicle treated controls) decrease in BAL eosinophil infiltration. These results demonstrate that an oligonucleotide targeted to IL4R-α decreased pulmonary inflammation by decreasing eosinophil infiltration.

A second experiment was performed to confirm the efficacy of ISIS 231894 to decrease AHR and eosinophilia in the acute model. Mice were dosed with OVA as described above. On days 17, 19, 21, 24 and 26, mice were dosed with 10 ug/kg ISIS 231894, mismatch control oligonucleotide, or vehicle (i.e. saline). ISIS 231894, but not the mismatch control oligonucleotide significantly reduced AHR and eosinophilia as compared to treatment with mismatch oligonucleotide or vehicle alone.

These data demonstrate that IL 4R-α is a valid target for the prevention of AHR and lung inflammation, and diseases associated therewith.

Mouse Model of Allergic Inflammation-Rechallenge Model

The rechallenge model of induced allergic inflammation allows testing of a pharmacologic approach in mice that have been previously sensitized and then exposed to an aeroallergen. During the first set of local allergen challenges, he mice develop allergen-specific memory T lymphocytes. Subsequent exposure to a second set of inhaled allergen challenges produces an enhanced inflammatory response in the lung, as demonstrated by increased levels of Th2 cytokines in lavage fluid. The rechallenge model of allergic inflammation includes a second series of aerosolized administration of OVA on days 59 and 60 in addition to the two IP OVA administrations on days 0 and 14 and the nebulized OVA administration of days 24, 25 and 26 of the acute model (see FIG. 1B). Using this model, oligonucleotide treatment occurs after the first set of local allergen challenges. This also allows for the evaluation of the target's role in a recall response, as opposed to an initial immune response.

In the rechallenge model, mice were treated with 10, 100 or 500 ug/kg of either ISIS 231894 or a 7 basepair mismatch control oligonucleotide (ISIS 352492) on days 52, 54, 56, 59 and 61 delivered by nose only inhalation. The study endpoints included many of those used in the acute model: Penh response (i.e., AHR reduction), inflammatory cells in BAL, mucus accumulation, and lung histology. IL 4R-α protein reduction in pulmonary structural and inflammatory cells was also evaluated.

Inflammatory IL4R-α Expression Profile

Lungs were harvested 6 hours following the second nebulized OVA re-challenge on Day 67. Lung cells were recovered after collagenase treatment of the tissue and analyzed by flow cytometry. IL 4R-α protein expression was measured on the surface of a mixed population of lung eosinophils and macrophages (CD11b-positive, GR-1 negative or low); CD11c-positive and MHC class II-positive dendritic cells; and E-cadherin-positive epithelial cells. Data are expressed as mean fluorescence intensity +/−SEM, N=4/group. *p<0.05 vs. vehicle treated controls by Student's T-test.

TABLE 9

IL 4Rα Cell Surface Protein Immunostaining (Mean Fluorescence Intensity) on Inflammatory and Epithelial Cells recovered from Lungs of Allergen Re-challenged Mice

| Treatments | | Eos/Macs (MFI) | DC (MFI) | Epithelial Cells (MFI) |
|---|---|---|---|---|
| Naïve | | 142 +/− 27 | 184 +/− 40 | 63 +/− 22 |
| Vehicle | | 181 +/− 26 | 181 +/− 25 | 181 +/− 15 |
| 231894 | 10 ug/kg | 120* +/− 7.8 | 200 +/− 38 | 100 +/− 42 |
| | 100 | 126* +/− 14 | 171 +/− 29 | 96* +/− 18 |
| | 500 | 113* +/− 9.9 | 124* +/− 20 | 120 +/− 64 |
| 352492 | 10 ug/kg | 135 +/− 32 | 206 +/− 26 | 144 +/− 30 |
| | 100 | 172 +/− 23 | 190 +/− 15 | 139 +/− 8.1 |
| | 500 | 186 +/− 32 | 257 +/− 87 | 149 +/− 24 |

These data demonstrate that oligonucleotides targeted to IL 4R-α is effective at reducing cell surface expression of IL 4R-α on multiple populations of cells within the lung.

Airway Hyperreponsiveness in Response to Methacholine as Determined by Penh

On day 60, AHR was analyzed by Penh as described above. A significant reduction in methacholine induced AHR was observed in animals inhaling 1.0 or 10.0 ug/kg ISIS 231894, but not 10 ug/kg of the mismatch control oligonucleotide (ISIS 352492), as compared to vehicle control animals as can be seen in Table 10 below. Data are presented as group means, N=10/group. *p<0.05 vs. vehicle treated controls by Student's T-test.

TABLE 10

Measurement of AHR by Penh in response to methacholine in a rechallenge mouse model

| Treatments | | Baseline | Methacholine dose (mg/kg) | | | | | | |
| | | | 0 | 3 | 6 | 12 | 25 | 50 | 100 |
|---|---|---|---|---|---|---|---|---|---|
| Naïve | | 0.53 | 0.48 | 0.57 | 1.10 | 2.10 | 2.70 | 2.61 | 2.86* |
| Vehicle | | 0.60 | 0.52 | 0.97 | 1.52 | 2.16 | 3.16 | 4.46 | 5.13 |
| 231894 | 10 ug/kg | 0.56 | 0.51 | 0.92 | 1.33 | 1.98 | 2.37 | 2.88 | 3.38* |
| 231894 | 1.0 ug/kg | 0.60 | 0.55 | 0.94 | 1.34 | 1.88 | 2.28 | 3.12 | 3.48* |
| 231894 | 0.1 ug/kg | 0.55 | 0.51 | 0.88 | 1.40 | 2.12 | 2.54 | 3.40 | 4.06 |
| 231894 | 0.01 ug/kg | 0.54 | 0.53 | 0.85 | 1.37 | 2.15 | 3.18 | 4.12 | 4.85 |
| 231894 | 0.001 ug/kg | 0.54 | 0.48 | 0.88 | 1.30 | 2.25 | 3.03 | 4.9 | 5.76 |
| 352492 | 10 ug/kg | 0.57 | 0.52 | 0.93 | 1.36 | 2.24 | 3.17 | 3.75 | 4.14 |

These results demonstrate that oligonucleotides targeted to IL4R-α are effective in the suppression of AHR.

Cytokine and Chemokine Expression in Bronchiolar Lavage Fluid

Pulmonary inflammation was also monitored through quantitation of Th2 cytokines and chemokines, and eosinophils in the airways. The production of Th2 cytokines and chemokines in the lung following aeroallergen exposure is associated with the induction of pulmonary inflammation and airway hyperresponsiveness. BAL fluid was collected, and the level of Th2 cytokines and chemokines were quantitated by ELISA on Day 67, 6 hours after the second nebulized OVA challenge in mice (n=4/group). The level of IL-13 was significantly ($p<0.05$) decreased at all three doses of Isis 231894. KC, the mouse analog of human IL-8, was significantly ($p<0.05$) decreased at the two higher doses of Isis 231894, and IL-5 and MCP-1 were significantly ($p<0.05$ vs. vehicle treated controls) decreased at the 500 ug/kg dose. Cytokine concentrations were determined from linear regression analysis of multi-point standard curves. The mismatch oligonucleotide, Isis 352942, had no effect on Th2 cytokine levels. These data demonstrate that inhibition of IL 4Rα expression is effective in decreasing Th2 cytokine and chemokine expression, specifically Th2 cytokine expression following allergen challenge, which is related to pulmonary inflammation and airway hyperresponsiveness.

Inflammatory Cell Infiltration

Cell differentials were performed on the BALF. The percent of eosinophils in BAL fluid was significantly reduced as compared to BALF from vehicle treated control animals. Results are shown in Table 12. Data are presented as group means, N=10/group. *$p<0.05$ vs. vehicle treated controls by Student's T-test as compared to vehicle control.

TABLE 11

Measurement of Airway Inflammatory Cells in Allergen Re-challenged Mice

| Treatments | | Mac | Lym | Eos | Neu |
|---|---|---|---|---|---|
| Naive | | 97.0 | 0.9 | 0.5* | 1.6 |
| Vehicle | | 31.0 | 5.7 | 59.9 | 3.4 |
| 231894 | 10 ug/kg | 72.1 | 4.2 | 23.0* | 0.7 |
| 231894 | 1.0 ug/kg | 69.8 | 5.1 | 24* | 0.6 |
| 231894 | 0.1 ug/kg | 53.1 | 5.6 | 38* | 3.3 |
| 231894 | 0.01 ug/kg | 47.3 | 4.8 | 44.1* | 3.8 |
| 231894 | 0.001 ug/kg | 38.9 | 4.6 | 53.2 | 3.3 |

These data demonstrate that oligonucleotides targeted to IL4R-α are effective at decreasing eosinophilia in the lung in response to allergen challenge.

Mucus Production

Mucus is an indicator of pulmonary inflammation. Muc5AC gene expression, mucus levels, and goblet cell metaplasia in the airways of OVA re-challenged mice were analyzed. Muc5AC mRNA levels were analyzed by quantitative RT-PCR in extracts from lung tissue harvested on Day 69. Expression levels were normalized to G3PDH expression. Muc 5AC/β-actin mRNA ratio significantly ($p<0.05$ vs. the vehicle treated control group) decreased with 231894 as compared to vehicle treatment. No decrease was observed in 352492 treated animals (n=4). There was also a significant ($p<0.05$ vs. the vehicle treated control group) decrease in mucus as determined by digital imaging of PAS-stained lungs from mice following treatment with IL 4R-α ASO, but not with saline or mismatch control oligonucleotide.

These data further demonstrate that an IL4R-α targeted antisense oligonucleotide approach is efficacious in the presence of established immunological memory, and that IL4R-α is an appropriate target for the amelioration, and/or treatment of AHR and pulmonary inflammation, and diseases associated therewith.

Mouse Model of Allergic Inflammation-Chronic Model

The chronic model of induced allergic inflammation uses a therapeutic treatment regimen, with ASO treatment initiated after the establishment local pulmonary inflammation. The chronic model recapitulates some of the histological features of severe asthma in humans, including collagen deposition and lung tissue remodeling. The chronic OVA model produces a more severe disease than that observed in the acute or rechallenged model.

This model includes intranasal OVA administration on days 27-29, 47, 61, and 73-75, at a higher dose (500 ug) than in the acute and chronic models, in addition to the two OVA IP administrations on days 0 and 14 (see FIG. 1C). Intranasal administration of the allergen results in a higher dose of the allergen delivered to the lungs relative to delivery by nebulizer. The increased number of allergen challenges produces more severe inflammatory events, resulting in increased lung damage and pathology more reflective of clinical asthma than other models, in the absence of therapeutic interventions. Endpoints tested were similar to those in the acute and rechallenge model, including Penh (AHR), BAL inflammatory cells and cytokines and mucus accumulation. This model also allows for the analysis of endpoints typically associated with chronic diseases, such as asthma and COPD, including sub-epithelial fibrosis, collagen deposition, enhanced goblet cell metaplasia, and smooth muscle cell hyperplasia.

Oligonucleotide, either ISIS 231894 or ISIS 352942 was administered by nose-only aerosol at a dose of either 5 ug/kg or 500 ug/kg on days 31, 38, 45, 52, 59, 66 and 73. Analysis of endpoints was performed on day 76, except cytokines which were evaluated on day 62, 6 hours post OVA challenge.

Airway Hyperreponsiveness in Response to Methacholine as Determined by Penh

Treatment of mice with both doses of ISIS 231894 resulted in a significant decrease in methacholine induced AHR as compared to treatment with vehicle (i.e. saline). Data are presented as group means, N=10/group. *$p<0.05$ vs. vehicle treated controls by Student's T-test.

TABLE 12

Measurement of AHR by Penh in response to methacholine in a chronic allergic inflammation model

| Treatment | | Base-line | Methacholine concentration (mg/ml) | | | | | | |
|---|---|---|---|---|---|---|---|---|---|
| | | | 0 | 3 | 6 | 12 | 25 | 50 | 100 |
| Naive | | 0.55 | 0.54 | 0.83 | 1.34 | 1.78 | 2.20 | 2.49 | 2.98* |
| Vehicle | | 0.67 | 0.59 | 1.38 | 2.01 | 2.95 | 5.00 | 5.86 | 6.17 |
| 231894 | 500 ug/kg | 0.68 | 0.66 | 1.48 | 1.77 | 2.29 | 3.03 | 3.79 | 4.50* |
| 231894 | 5 ug/kg | 0.74 | 0.73 | 1.50 | 1.96 | 2.05 | 2.68 | 4.13 | 4.41* |

These data demonstrate that oligonucleotides targeted to IL4R-α delivered using at therapeutic treatment regimen are effective at preventing AHR in response to methacholine challenge.

Inflammatory Cell Infiltration

Treatment of mice with the higher dose of 231894 resulted in a significant decrease in the percent of eosinophils in BAL fluid as compared to vehicle control. Both doses of ISIS 231894 significantly reduced the percent neutrophils in BAL as compared to vehicle control. Data are presented as group means, N=7/group. *p<0.05 vs. vehicle treated controls by Student's T-test as compared to vehicle control.

The most substantial difference in the models is in the endpoints analyzed. Endpoints include, but are not limited to, the amount of sneezing and nasal scratching immediately after administration of allergen challenge (i.e. intranasal OVA), and nasal histology including mucus and eosinophil counts and measurements of cytokines or other inflammatory products in nasal lavage fluid or nasal tissues. Methods for performing such analyses are detailed in the references cited which are incorporated herein by reference. Administration of oligonucleotides targeted to IL-4R alpha decrease nasal inflammation, as evidenced by fewer infiltrating eosinophils

TABLE 13

Measurement of inflammatory cell infiltration in a chronic allergic inflammation mouse model

| Treatments | | Day 62 | | | | Day 76 | | | |
| --- | --- | --- | --- | --- | --- | --- | --- | --- | --- |
| | | Mac | Lym | Eos | Neu | Mac | Lym | Eos | Neu |
| Naïve | | 91.8 | 1.6 | 0.2* | 6.4* | 91.3 | 2.2 | 1.2* | 5.3* |
| Vehicle | | 25.4 | 6.4 | 12.2 | 56.0 | 37.5 | 3.4 | 48.5 | 10.6 |
| 231894 | 500 ug/kg | 58.2 | 2.4 | 4.8* | 34.6* | 61.9 | 4.8 | 29.7* | 3.6* |
| 231894 | 5 ug/kg | 50.7 | 6.8 | 4.5* | 38.0* | 42.8 | 6.4 | 44.5 | 6.3 |

These data demonstrate that oligonucleotides targeted to IL4R-α delivered using a therapeutic treatment regimen are effective at decreasing eosinophilia and neutrophilia in the lung in response to allergen challenge.

Cytokine Expression in Bronchiolar Lavage Fluid

Pulmonary inflammation was also monitored by cytokine and chemokine expression and inflammatory cell infiltration. BALF was collected, and the level of four Th2 cytokines were quantitated by ELISA on day 62, 6 hours post allergen challenge. Analysis of BAL fluid revealed a significant reduction in IL-5 and KC in high dose 231894 treated animals as compared to vehicle treated animals.

These data further confirm the utility of oligonucleotides targeted to IL 4R-α for the amelioration and treatment of AHR and pulmonary inflammation and diseases associated therewith.

EXAMPLE 7

Mouse Model of Allergic Inflammation, Analysis for Nasal Rhinitis Endpoints

Mouse models of allergen-induced acute and chronic nasal inflammation similar to those above have been used to study allergic rhinitis in mice (Hussain et al., Larangyoscope. 112: 1819-1826. 2002; Iwasaki et al., J. Allergy Clin Immunol. 112: 134-140. 2003; Malm-Erjefaelt et al., Am J Respir Cell Mol Biol. 24:352-352.2001; McCusker et al., J Allergy Clin Immunol., 110: 891-898; Saito el., Immunology. 104:226-234. 2001). In all of the models, the mice were sensitized to OVA by injection, as above, followed by intranasal OVA instillation.

quantitated by digital imaging, and fewer nasal rubs and sneezes per unit of time in IL 4R-α ASO treated animals as compared to saline treatment.

EXAMPLE 8

Rodent Model of Smoking Induced Pulmonary Disease

Smoking is known to cause lung irritation and inflammation which can result in a number of diseases in humans including, but not limited to, emphysema and COPD. A number of smoking animal models are well known to those skilled in the art including those utilizing mice (Churg et al., 2002. Am. J. Respir. Cell. Mol. Biol. 27:368-347; Churg et al., 2004. Am. J. Respir. Crit. Care Med. 170:492-498, both incorporated herein by reference), rats (e.g., Sekhon et al., 1994. Am. J. Physiol. 267:L557-L563, incorporated herein by reference), and guinea pigs (Selman et al., 1996. Am J. Physiol. 271:L734-L739, incorporated herein by reference). Animals are exposed to whole smoke using a smoking apparatus (e.g., Sekhon et al., 1994. Am. J. Physiol. 267:L557-L563) well known to those skilled in the art.

Changes in lung physiology are correlated with dose and time of exposure. In short term studies, cell proliferation and inflammation were observed. In one study, exposure of rats to 7 cigarettes for 1, 2, or 7 days resulted in proliferation of pulmonary artery walls at the level of the membranous bronchioles (MB), respiratory bronchioles (RB), and alveolar ducts (AD). Endothelial cell proliferation was only present in vessels associated with AD. In a separate study (Churg et al., 2002. Am. J. Respir. Cell. Mol. Biol. 27:368-347), mice exposed to whole smoke from four cigarettes were shown to have an increase in neutrophils, desmosine (an indicator of elastin breakdown), and hydroxyproline (an indicator of collagen breakdown) after only 24 hours. In a long term study, an emphysema-like state was induced (Churg et al., 2004. Am. J. Respir. Crit. Care Med. 170:492-498). Mice exposed to whole smoke from four cigarettes using a standard smoking apparatus, for five days per week for six months were found to have an increase in neutrophils and macrophages in BALF as compared to control mice. Whole lung matrix metalloproteinases (MMP)-2, -9, -12, and -13, and matrix type-1 (MT-1) proteins were increased. An increase in matrix breakdown products was also observed in BALF. These markers correlate with tissue destruction and are observed in human lungs with emphysema.

These models can be used to determine the efficacy of therapeutic interventions for the prevention, amelioration, and/or treatment of the damage and disease caused by cigarette smoke and/or other insults. Administration of oligonucleotide can be performed prior to, concurrent with, and/or after exposure to smoke to provide a prophylactic or therapeutic model. ISIS 231894 is 100% complimentary to both mouse and rat IL 4R-α; therefore, it can be used in both mouse and rat studies. Dose ranges are determined by the time of oligonucleotide administration relative to smoke inhalation, with lower doses (e.g., 1-100 ug/kg) required for prevention of lung damage. Higher doses (e.g., 100-1000 ug/kg) are required for treatment after, or alternating with, smoke exposure. Positive control (e.g., smoke exposure, no oligonucleotide administration) and negative control (e.g., no smoke exposure, with or without oligonucleotide treatment) animals are also analyzed.

Endpoints for analysis include those discussed in the asthma models above. Functional endpoints include AHR, resistance and compliance. Morphological changes include BAL cell, cytokine levels, histological determinations of alveolar destruction (i.e., increase in alveolar space) and airway mucus accumulation, as well as tissue markers of disease including collagen and elastin. The emphysematous changes specific to this model discussed in this example can also be analyzed to determine the effect of the antisense oligonucleotide.

EXAMPLE 9

Mouse Model of Elastase Induced Emphysema

Elastase is an essential mediator in lung damage and inflammation release by neutrophils recruited following smoke-induced damage. A rat model of emphysema has been developed to analyze the process of elastase mediated lung damage, and possible therapeutic interventions to prevent, ameliorate, and/or treat the pathologies associated with such damage and resulting disease (Kuraki et al., 2002. Am J Respir Crit Care Med., 166:496-500, incorporated herein by reference). Intratracheal application of elastase induced emphysematous changes in all lobes of the lung including severe lung hemorrhage as demonstrated by increased hemoglobin in BALF; neutrophil accumulation in BALF; inhibition of hyperinflation and degradation of elastic recoil. Histopathological changes included elastase-induced airspace enlargement and breakdown of alveoli. These changes are similar to those observed in human emphysema.

In the model, rats are treated with human sputum elastase (SE563, Elastin Products, Owensville, Mo.) without further purification. Rats are treated with a sufficient dose of elastase, about 200 to 400 units, by intratracheal administration using a microsprayer. Alternatively, intratracheal administration can be performed as described above in the mouse models. After sufficient time to allow for damage to occur, about eight weeks, functional and morphological changes are analyzed. A similar model can be performed using mice with a lowered dose of elastase relative to weight and/or lung area (e.g., 0.05 U of porcine pancreatic elastase/g body weight).

Administration of oligonucleotide can be performed prior to, concurrent with, and/or after administration of elastase to provide a prophylactic or therapeutic model. ISIS 231894 is 100% complimentary to both mouse and rat IL 4R-α. Dose ranges are determined by the time of oligonucleotide administration relative to elastase administration with lower doses (e.g., 1-100 ug/kg) required for prevention of lung damage. Higher doses (e.g., 100-1000 ug/kg) are required for treatment after, or alternating with, elastase administration. Positive control (e.g., elastase treatment, no oligonucleotide administration) and negative control (e.g., no elastase, with or without oligonucleotide treatment) animals are also analyzed.

Endpoints for analysis include those discussed in the asthma models above. Functional endpoints include AHR, resistance and compliance. Morphological changes include BAL cell, cytokine levels, and mucus accumulation. The emphysematous changes specific to this model discussed in this example can also be analyzed to determine the effect of the antisense oligonucleotide.

What is claimed is:

1. A single-stranded oligomeric compound 16 to 35 nucleobases in length comprising at least 16 contiguous nucleobases of the nucleobase sequence set forth in SEQ ID NO: 280.

2. The compound of claim 1, comprising at least one modified internucleoside linkage, sugar moiety, or nucleobase.

3. The compound of claim 2, comprising a chimeric oligonucleotide.

4. The compound of claim 2, wherein the modified internucleoside linkage is a phosphorothioate linkage.

5. The compound of claim 2, wherein the modified sugar moiety is a 2'-O-(2-methoxyethyl)(2'-MOE) modification.

6. The compound of claim 2, wherein the modified nucleobase is a 5-methylcytosine.

7. A pharmaceutical composition comprising a compound of claim 1 and a pharmaceutically acceptable penetration enhancer, carrier, or diluent.

8. A single-stranded antisense oligonucleotide with a nucleotide sequence consisting of the sequence set forth in SEQ ID NO: 280.

9. The antisense oligonucleotide of claim 8 comprising a central region of ten 2'-deoxynucleotides flanked on each side by five 2'-MOE nucleotides and phosphorothioate internucleoside linkages at each position.

10. The antisense oligonucleotide of claim 9 wherein each cytidine residue is a 5-methylcytidine.

11. A pharmaceutical composition comprising an antisense oligonucleotide of claim 10 and a pharmaceutically acceptable penetration enhancer, carrier, or diluent.

* * * * *

UNITED STATES PATENT AND TRADEMARK OFFICE
CERTIFICATE OF CORRECTION

PATENT NO.        : 7,507,810 B2
APPLICATION NO.   : 11/548650
DATED             : March 24, 2009
INVENTOR(S)       : James G. Karras et al.

It is certified that error appears in the above-identified patent and that said Letters Patent is hereby corrected as shown below:

Delete Title pg. insert new Title pg. (Attached)

Include Fig. 1 as Sole Drawing (Attached)

At column 39, line 54, delete "3" and insert -- 1 --

Signed and Sealed this

Twenty-ninth Day of December, 2009

David J. Kappos
*Director of the United States Patent and Trademark Office*

(12) United States Patent
Karras et al.

(10) Patent No.: US 7,507,810 B2
(45) Date of Patent: Mar. 24, 2009

(54) COMPOSITIONS AND THEIR USES DIRECTED TO IL-4R ALPHA

(75) Inventors: James G. Karras, San Marcos, CA (US); Susan Gregory, San Diego, CA (US); Susan M. Freier, San Diego, CA (US); William A. Gaarde, Carlsbad, CA (US); Mausumee Guha, Carlsbad, CA (US)

(73) Assignee: ISIS Pharmaceuticals, Inc., Carlsbad, CA (US)

(*) Notice: Subject to any disclaimer, the term of this patent is extended or adjusted under 35 U.S.C. 154(b) by 0 days.

(21) Appl. No.: 11/548,650

(22) Filed: Oct. 11, 2006

(65) Prior Publication Data
US 2007/0161593 A1 Jul. 12, 2007

Related U.S. Application Data

(63) Continuation of application No. PCT/US2006/006645, filed on Feb. 24, 2006.

(60) Provisional application No. 60/656,760, filed on Feb. 25, 2005, provisional application No. 60/688,897, filed on Jun. 9, 2005, provisional application No. 60/700,656, filed on Jul. 19, 2005, provisional application No. 60/709,404, filed on Aug. 18, 2005.

(51) Int. Cl.
C07H 21/04 (2006.01)
C07H 21/02 (2006.01)
A61K 48/00 (2006.01)

(52) U.S. Cl. ............ 536/24.5; 536/23.1; 536/24.3; 514/44

(58) Field of Classification Search ............ None
See application file for complete search history.

(56) References Cited

U.S. PATENT DOCUMENTS

| | | | |
|---|---|---|---|
| 5,489,677 A | 2/1996 | Sanghvi et al. | |
| 5,602,240 A | 2/1997 | De Mesmaeker et al. | |
| 5,625,050 A | 4/1997 | Beaton et al. | |
| 5,677,439 A | 10/1997 | Weis et al. | |
| 5,688,941 A | 11/1997 | Cook et al. | |
| 5,700,922 A | 12/1997 | Cook | |
| 5,719,262 A | 2/1998 | Buchardt et al. | |
| 5,750,692 A | 5/1998 | Cook et al. | |
| 5,789,573 A | 8/1998 | Baker et al. | |
| 5,898,031 A | 4/1999 | Crooke | |
| 6,007,992 A | 12/1999 | Lin et al. | |
| 6,028,183 A | 2/2000 | Lin et al. | |
| 6,107,094 A | 8/2000 | Crooke | |
| 6,147,200 A | 11/2000 | Manoharan et al | |
| 6,210,892 B1 | 4/2001 | Bennett et al. | |
| 6,379,890 B1 | 4/2002 | Hershey | |
| 6,656,695 B2 | 12/2003 | Berg et al. | |
| 6,656,730 B1 | 12/2003 | Manoharan | |
| 6,762,169 B1 | 7/2004 | Manoharan | |
| 6,822,087 B1 | 11/2004 | Renzi | |
| 6,878,751 B1 | 4/2005 | Donnelly et al. | |
| 2002/0049173 A1 | 4/2002 | Bennett et al. | |
| 2003/0078220 A1 | 4/2003 | Chew et al. | |
| 2003/0104410 A1 | 6/2003 | Mittmann | |
| 2003/0158403 A1 | 8/2003 | Manoharan et al. | |
| 2003/0175906 A1 | 9/2003 | Manoharan et al. | |
| 2003/0207804 A1 | 11/2003 | Manoharan et al. | |
| 2004/0040052 A1 | 2/2004 | Radcliffe et al | |
| 2004/0049022 A1 | 3/2004 | Nyce et al. | |
| 2004/0171566 A1 | 9/2004 | Monia et al. | |
| 2004/0235164 A1 | 11/2004 | Bennett et al. | |
| 2005/0143333 A1* | 6/2005 | Richards et al. | 514/44 |
| 2005/0261219 A1 | 11/2005 | Richards et al. | |

FOREIGN PATENT DOCUMENTS

| | | | |
|---|---|---|---|
| WO | WO 94/26764 A1 | 11/1994 | |
| WO | WO 96/40162 | 12/1996 | |
| WO | WO 99/66037 A2 | 12/1999 | |
| WO | WO 00/34789 * | 6/2000 | 536/24.5 |
| WO | WO 00/34789 A2 | 6/2000 | |
| WO | WO 02/085308 A2 | 10/2002 | |
| WO | WO 02/085309 A2 * | 10/2002 | 514/44 |
| WO | WO 02/085309 A2 | 10/2002 | |
| WO | WO 2003/004602 A2 | 1/2003 | |
| WO | WO 2004/011613 A2 | 2/2004 | |
| WO | WO 2004/031237 | 5/2004 | |
| WO | WO 2004/045543 A2 | 6/2004 | |
| WO | WO 2004/108945 A2 | 12/2004 | |

(Continued)

OTHER PUBLICATIONS

Only pp. 1-27 and 693 are included for document WO 02/085309 A2.*

(Continued)

*Primary Examiner*—Amy Bowman
(74) *Attorney, Agent, or Firm*—Swanson & Bratschun, L.L.C.

(57) ABSTRACT

Disclosed herein are compounds, compositions and methods for modulating the expression of IL-4R alpha in a cell, tissue or animal. Also provided are methods of target validation. Also provided are uses of disclosed compounds and compositions in the manufacture of a medicament for treatment of diseases and disorders related to expression of IL-4R-α, airway hyperresponsiveness, and/or pulmonary inflammation.

11 Claims, 1 Drawing